US010226475B2

(12) United States Patent
Arenas et al.

(10) Patent No.: US 10,226,475 B2
(45) Date of Patent: Mar. 12, 2019

(54) COMPOUND AND METHOD FOR THE TREATMENT AND DIAGNOSIS OF NEURODEGENERATIVE CONDITIONS

(71) Applicant: SWANSEA UNIVERSITY, Swansea, South Wales (GB)

(72) Inventors: Ernest Arenas, Swansea (GB); William Griffiths, Swansea (GB); Yuqin Wang, Swansea (GB); Spyridon Theofilopoulos, Swansea (GB)

(73) Assignee: SWANSEA UNIVERSITY, Swansea (GB)

( * ) Notice: Subject to any disclaimer, the term of this patent is extended or adjusted under 35 U.S.C. 154(b) by 0 days.

(21) Appl. No.: 14/770,313

(22) PCT Filed: Feb. 26, 2014

(86) PCT No.: PCT/GB2014/050572
§ 371 (c)(1),
(2) Date: Aug. 25, 2015

(87) PCT Pub. No.: WO2014/132052
PCT Pub. Date: Sep. 4, 2014

(65) Prior Publication Data
US 2016/0000807 A1     Jan. 7, 2016

(30) Foreign Application Priority Data

Feb. 27, 2013 (GB) .................................. 1303589.4

(51) Int. Cl.
*G01N 33/92*     (2006.01)
*A61K 31/575*    (2006.01)

(52) U.S. Cl.
CPC .......... *A61K 31/575* (2013.01); *G01N 33/92* (2013.01); *G01N 2500/04* (2013.01); *G01N 2500/10* (2013.01); *G01N 2560/00* (2013.01); *G01N 2800/28* (2013.01)

(58) Field of Classification Search
USPC ....................................................... 514/128
See application file for complete search history.

(56) References Cited

U.S. PATENT DOCUMENTS 6,379,666 B1 * 4/2002 Tobinick .............. C07K 16/241
424/134.1

FOREIGN PATENT DOCUMENTS

WO    2005/060694 A2    7/2005
WO    2008/071960       * 6/2008
WO    2014/132052 A2    9/2014

OTHER PUBLICATIONS

Ogundare Cerebrospinal Fluid Steriodomics: Are Bioactive Bile Acids Present in Brain, Journal of Biological Chemistry, 2010, 285(7), pp. 4666-4679).*
Bettowski (Statins and ALS: The possible role of impaired LXR signaling, Med Sci Monit, 2010; 16(3): RA73-78).*
Alberti et al., "Hepatic cholesterol metabolism and resistance to dietary cholesterol in LXRβ-deficient mice", The Journal of Clinical Investigation, 2001, pp. 565-573, vol. 107, No. 5.
Arnoldi et al., "Clinical phenotype variability in patients with hereditary spastic paraplegia type 5 associated with CYP7B1 mutations", Clinical Genetics, 2012, pp. 150-157, vol. 81.
Axelson et al., "Occurrence of 3β-hydroxy-5-cholestenoic acid, 3β,7α-dihydroxy-5-cholestenoic acid, and 7α-hydroxy-3-oxo-4-cholestenoic acid as normal constituents in human blood", Journal of Lipid Research, 1988, pp. 629-641, vol. 29.
Bjorkhem et al., "Oxysterols and neurodegenerative diseases", Molecular Aspects of Medicine, 2009, pp. 171-179, vol. 30.
Chong et al., "Annual Symposium of the Society for the Study of Inborn Errors of Metabolism", J. Inherit. Metab. Dis., 2010, 33 (Suppl 1), pp. S1-S197.
Criscuolo et al., "Two novel CYP7B1 mutations in Italian families with SPG5: a clinical and genetic study", Journal of Neurology, 2009, pp. 1252-1257, vol. 256.
Hennebert et al., "Epimerase activity of the human 11β-hydroxysteroid dehydrogenase type 1 on 7-hydroxylated C19-steroids", Journal of Steroid Biochemistry and Molecular Biology, 2009, pp. 57-63, vol. 114.
International Search Report and Written Opinion from related International Application No. PCT/GB2014/050572, dated Sep. 26, 2014; 17 pgs.
Meaney et al., "Novel route for elimination of brain oxysterols across the blood-brain barrier: conversion into 7α-hydroxy-3-oxo-4-cholestenoic acid", Journal of Lipid Research, 2007, pp. 944-951, vol. 48.
Mizuochi et al., "Successful Heterozygous Living Donor Liver Transplantation for an Oxysterol 7α-Hydroxylase Deficiency in a Japanese Patient", Liver Transplantation, 2011, pp. 1059-1065, vol. 17, No. 9.
Ogundare et al., "Cerebrospinal Fluid Steroidomics: Are Bioactive Bile Acids Present in Brain?", The Journal of Biological Chemistry, 2010, pp. 4666-4679, vol. 285, No. 7.
Riddell et al., "The LXR agonist TO901317 selectively lowers hippocampal Aβ42 and improves memory in the Tg2576 mouse model of Alzheimer's disease", Molecular and Cellular Neuroscience, 2007, pp. 621-628, vol. 34.
Schule et al., "Marked accumulation of 27-hydroxycholesterol in SPG5 patients with hereditary spastic paresis", Journal of Lipid Research, 2010, pp. 819-823, vol. 51.
Song et al., "Cholestenoic Acid Is a Naturally Occurring Ligand for Liver X Receptor α*", Endocrinology, 2000, pp. 4180-4184, vol. 141, No. 11.

(Continued)

*Primary Examiner* — Kathrien A Cruz
(74) *Attorney, Agent, or Firm* — Stoel Rives LLP

(57) ABSTRACT

A reagent selected from cholestenoic acid or an inhibitor of an enzyme in the cholestenoic acid biosynthetic or metabolic pathway for use in the treatment of neurodegenerative conditions. In particular, the reagent is a cholestenoic acid of a particular form, such as 3β,7α-dihydroxycholest-5-en-26-oic (3β,7α-diHCA), not previously associated with neural tissue or CSF. Pharmaceutical compositions, methods of treatment or prevention of neurodegenerative conditions as well as diagnostic methods and novel biomarkers form further aspects of the invention.

6 Claims, 25 Drawing Sheets

(56) References Cited

OTHER PUBLICATIONS

Theofilopoulos et al., "Brain endogenous liver X receptor ligands selectively promote midbrain neurogenesis", Nature Chemical Biology, 2012, pp. 126-133, vol. 9.

Theofilopoulos et al., "Brain endogenous Liver X Receptor ligands selectively promote midbrain neurogenesis", 2013 supplement; 14 pgs.

Ueki et al., "Neonatal Cholestatic Liver Disease in an Asian Patient With a Homozygous Mutation in the Oxysterol 7α-hydroxylase Gene", Journal of Pediatric Gastroenterology and Nutrition, 2008, pp. 465-469, vol. 46.

\* cited by examiner

3D

3E

3F

4H

4J

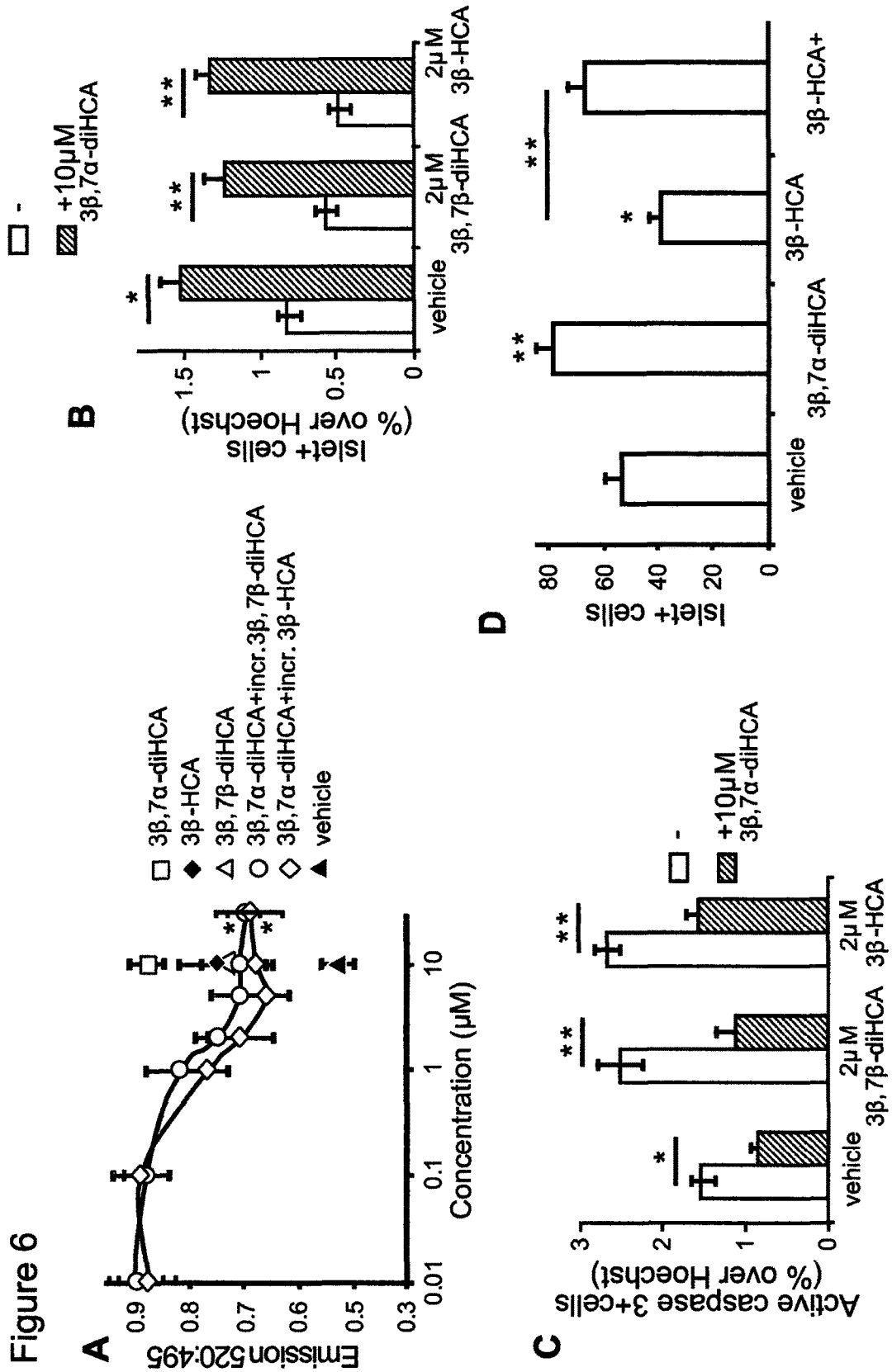

E    vehicle    3β,7α-diHCA

3β-HCA    3β-HCA+ 3β,7α-diHCA

7A

7B

7C

7D

10A

10B

COMPOUND AND METHOD FOR THE TREATMENT AND DIAGNOSIS OF NEURODEGENERATIVE CONDITIONS

FIELD OF THE INVENTION

The present invention relates to compounds, methods for the treatment of neurodegenerative conditions and methods of diagnosis of neurodegenerative conditions and in particular but not exclusively to the use of a cholestenoic acid to treat neurodegenerative conditions such as motor neuron disease.

BACKGROUND OF THE INVENTION

The vertebrate central nervous system (CNS) is composed of a wide variety of neurons that are generated following tightly-regulated developmental programs. Characterization of the function and specificity of molecules and regulatory elements working on distinct neuronal populations is thus essential in order to enhance our understanding of how such complexity is achieved in the developing brain and how it is maintained in the adult brain.

Cholesterol is present at high levels in the CNS of vertebrates and is metabolized in the brain, predominantly to 24S-hydroxycholesterol (24S-HC). Neurodegenerative conditions that occur are as a result of neurons in the brain being lost. In conditions such as Parkinson's disease, which is a common neurodegenerative disease, the condition is linked to the loss of substantial nigra midbrain dopaminergic neurons. The loss of nigrostriatal neurons results in symptoms such as tremors that are a classic symptom of the illness.

Research has worked on the use of cell replacement therapy (CRT) and regenerative medicine to try and combat the disease, which is becoming more prevalent as populations age. However, an alternative means of developmental and adult regulation is via nuclear receptors. It has been found that the liver X receptor (Lxr) ligand is a specific inducer of midbrain dopaminergic neurons both in embryonic stem cells, neural tissues and even in whole animals. In particular, examples of nuclear receptors expressed in embryonic and adult brain having both a developmental role and a function in the adult brain are the liver X receptors (Lxrα and β). The liver X receptors (Lxrα and β), are activated by oxysterols. Analysis of double Lxrα and Lxrβ knockout mice revealed that Lxrs are required for neurogenesis during ventral midbrain (VM) development. Moreover, adult male Lxrβ knockout mice (Lxrβ−/−) show a progressive accumulation of lipids in the brain and loss of spinal cord motor neurons, suggesting a neuroprotective role of Lxrs and their ligands on adult motor neurons. Similarly, the number of Islet1+ oculomotor neurons is lower in the developing midbrain of Lxrα−/−β−/− mice, indicating a role of Lxrs, not only in the maintenance of adult motor neurons, but also in their development. Enzymes involved in the synthesis of cholesterol and oxysterols, such as 2,3-oxidosqualene-lanosterol cyclase, are localized in Islet1+ oculomotor neurons in the mouse ventral midbrain and it has been found that oxysterols and endogenous brain Lxr ligands are sufficient to regulate neurogenesis in the developing ventral midbrain. While endogenous brain Lxr ligands have been identified and found to regulate the development of midbrain dopamine neurons and red nucleus neurons (Theofilopoulos et al. (2012) Nat. Chem. a Biol. 9, 126-133), to date, no endogenous ligand that is capable of regulating the survival of motor neurons in vivo has so far been identified.

It has also been reported that cholesterol metabolites that had the capacity to activate Lxrs can be identified in human cerebrospinal fluid (CSF) (Ogundare M, et al. *J Biol Chem* 2010; 285(7):4666-79.).

In order to identify novel Lxr ligands that regulate motor neuron function the applicants delved deeper into the human CSF sterolome and examined plasma of patients with different human diseases associated with motor neuron degeneration, hereditary spastic paresis (HSP) type 5 (SPG5) and cerebrotendinous xanthomatosis (CTX) as well as infants with oxysterol 7α-hydoxylase deficiency (O7AHD). These diseases result from mutations in the cytochrome P450 CYP7B1 (SPG5 and O7AHD) and CYP27A1 genes (CTX). The enzymes coded by these genes are responsible for 7α-hydroxylation of oxysterols and (25R),26-hydroxylation of sterols, respectively, reactions that generate further oxysterols and ultimately cholestenoic acids (FIG. 1 hereinafter). The applicants found that, surprisingly, specific cholestenoic acids with a 3β-hydroxy-5-ene, but not a 3-oxo-4-ene, structure activate Lxrα and β in neuronal cells, increase expression of Islet-1, a transcription factor required for the development of motor neurons, and promote the survival of Islet1+ oculomotor neurons. Moreover these effects were abolished by knock-down or knock-out of the Lxrs in zebrafish or in rodent models.

In addition, the applicants showed that patients with CTX, SPG5 and O7AHD are unable to synthesize normal amounts of the Lxr ligand 3β,7α-dihydroxycholest-5-en-26-oic acid (3β,7α-diHCA), a cholestenoic acid that the applicants found promotes neuronal survival. This is of interest in relation to the fact that patients with SPG5 present with motor neuron degeneration and spastic paraplegia. Patients with CTX may sometimes also present with spasticity, possibly due to upper motor neuron degeneration. These results have important implications for the treatment neurological diseases leading to motor neuron degeneration. They indicate that cholestenoic acid acting as Lxr ligands, as well as inhibitors of specific biosynthetic enzymes in the cholestenoic acid biosynthetic and metabolic pathways, are useful pharmaceuticals for the treatment of motor neuron disorders.

Furthermore, the applicants showed that whilst patients with CTX had abnormally low levels of all of cholest-(25R)-5-en-3β,26-diol 26-HC (26-HC), 3β-hydroxycholest-5-en-26-oic acid (3β-HCA) and 3β,7β-dihydroxycholest-5-en-26-oic (3β,7β-diHCA), patients with SPG5 and O7AHD had elevated levels of some or all of these (FIG. 1) and that 3β-HCA and 3β,7β-diHCA, in particular, decreased neuronal survival.

All of these results have important implications for the diagnosis of neurological diseases leading to motor neuron degeneration. They indicate that the levels of certain cholestenoic acids (3β-HCA, 3β,7β-diHCA and 3β,7β-diHCA) and a precursor (26-HC) alone or in combination are diagnostic and/or prognostic for motor neuron degenerative disease and/or the level of neurodegeneration.

SUMMARY OF THE INVENTION

According to a first aspect of the invention there is provided a reagent selected from a cholestenoic acid, a cholestenoic acid precursor or an inhibitor of an enzyme in the cholestenoic acid biosynthetic or metabolic pathway or a pharmaceutically acceptable salt thereof for use in the treatment of neurodegenerative conditions.

The applicants have found that cholestenoic acids, and in particular certain forms including some forms not previously identified as being present in the CSF have a direct effect on neuron generation and survival. Some forms of cholestenoic acid appear to show neuroprotective effects, whilst others may be harmful or neurotoxic. As a result, modifying the relative amounts of the specific forms of cholestenoic acid, for example by administering favourable cholestenoic acids or by inhibiting the production of undesirable cholestenoic acids will constitute a useful method for treating or preventing neurodegenerative conditions.

In a particular embodiment of the first aspect of the invention, a cholestenoic acid or a pharmaceutically acceptable salt thereof, used in the treatment of neurodegenerative conditions. In particular the cholestenoic acid is an acid which has a neuroprotective effect, such as 3β,7α-dihydroxycholest-5-en-26-oic (3β,7α-diHCA), or a precursor of this form such as cholest-(25R)-5-en-3β,26-diol 26-HC (26-HC).

Alternatively, inhibition of the production of undesirable cholestenoic acids, such as of 3β,7β-dihydroxycholest-5-en-26-oic (3β,7β-diHCA) or 3β-hydroxycholest-5-en-26-oic (3β-HCA), may be achieved by interfering with the biosynthetic pathway involved in the production of such cholestenoic acids, in particular by administration of an inhibitor of an enzyme that produces such a form of cholestenoic acid. For example, an inhibitor of an epimerase enzyme, that prevents the production of 3β,7β-dihydroxycholest-5-en-26-oic (3β,7β-diHCA), a cholestenoic acid which has been identified by the applicants as having a degree of toxicity to neurons from the desirable epimeric form, 3β,7α-diHCA would provide a beneficial effect. Enzymes that produce this effect and inhibitors therefore may be determined using conventional screening methods. For example, HSD1 enzymes such as 11β-hydroxysteroid dehydrogenase type 1 (11β-HSD1 EC 1.1.1.146) may show epimerase activity (Hennebert O, et al. J Steroid Biochem Mol Biol. 2009 114(1-2) 57-63), The use of inhibitors of HSD1 enzymes has been suggested in the treatment of certain neurological disorders previously (see WO2005/060694), but applications in the control of cholestenoic acid biosynthesis and the effects on conditions such as motor neuron disease has not previously been evaluated.

Methods for screening for compounds useful in the treatment of neurodegenerative conditions, which comprises identifying suitable enzyme inhibitors, in particular, for inhibitors of an epimerase enzyme that converts 3β,7α-diHCA to 3β,7β-diHCA form a further aspect of the invention. The precise form of these methods will be determinable by the skilled person with reference. For instance, these methods may involve incubation of the enzyme with the enzyme substrate (such as 3β,7α-diHCA) and the proposed inhibitor in vitro, after which the presence or amount of the enzymatic reaction product (such as 3β,7β-diHCA) is determined and the results compared with similar results obtained in the absence of the proposed inhibitor. Alternatively, the binding site of the enzyme to the substrate such as 3β,7α-diHCA is identified and isolated peptides or proteins comprising said binding site may be used in binding assays, to detect possible inhibitor compounds that bind specifically to that site.

As used herein, the expression 'pharmaceutically acceptable salt' includes both pharmaceutically acceptable base and acid addition salts. For example a base-addition salt of a cholestenoic acid may be an alkali or alkaline earth metal salt such as a sodium, calcium or magnesium salt, or an ammonium salt, or a salt with an organic base such as methylamine, dimethylamine, trimethylamine, piperidine, morpholine or tris-(2-hydroxyethyl)amine Such salts may be prepared by methods known to those skilled in the art.

According to a second aspect of the invention there is provided the use of a reagent selected from cholestenoic acid, a cholestenoic acid precursor or an inhibitor of an enzyme in the cholestenoic acid biosynthetic or metabolic pathway, or a pharmaceutically acceptable salt in the preparation of an agent for the treatment of neurodegenerative conditions.

In a particular embodiment of the second aspect, a cholestenoic acid such as 3β,7α-dihydroxycholest-5-en-26-oic (3β,7α-diHCA), or a precursor of this form such as cholest-(25R)-5-en-3β,26-diol (26-HC) is used in the preparation.

The cholestenoic acid or inhibitor of an enzyme in the cholestenoic acid biosynthetic or metabolic pathway will generally be administered in the form of a pharmaceutical composition, in which it is combined with a pharmaceutically acceptable carrier.

According to a third aspect of the invention there is provided a pharmaceutical or veterinary composition comprising a cholestenoic acid, a cholestenoic acid precursor or inhibitor of an enzyme in the cholestenoic acid biosynthetic or metabolic pathway, or a pharmaceutically acceptable salt for use in the treatment of neurodegenerative conditions. In particular, the pharmaceutical or veterinary composition will comprise a cholestenoic acid.

Suitable pharmaceutical compositions will be in either solid or liquid form including pharmaceutically acceptable salts, crystalline polymorphs, solvates, hydrates, co-crystals and amorphous forms. They may be adapted for administration by any convenient peripheral route, such as parenteral, oral, vaginal or topical administration or for administration by inhalation or insufflation. The pharmaceutical acceptable carrier may include diluents or excipients which are physiologically tolerable and compatible with the active ingredient. These include those described for example in Remington's Pharmaceutical Sciences, Mack Publishing Co. (A. R. Gennaro edit. 1985).

Parenteral compositions are prepared for injection or infusion, for example either subcutaneously, intramuscularly, intradermally, intravenously, intraspinally, intrathecally, epidurally or via needle-free injection systems. They may be liquid solutions or suspensions, or they may be in the form of a solid that is suitable for solution in, or suspension in, liquid prior to injection. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH-buffering agents, and the like.

Oral formulations will be in the form of solids or liquids, and may be solutions, syrups, suspensions, tablets, pills, capsules, sustained-release formulations, or powders. Oral formulations include such normally employed excipients as, for example, pharmaceutical grades of mannitol, lactose, starch, magnesium stearate, sodium saccharin, cellulose, magnesium carbonate, and the like.

Topical formulations will generally take the form of suppositories, pessaries, intranasals sprays or aerosols, buccal or sublingual tablets or lozenges. For suppositories or pessaries, traditional binders and excipients may include, for example, polyalkylene glycols or triglycerides; such suppositories or pessaries may be formed from mixtures containing the active ingredient. Other topical formulations may take the form of a lotion, solution, cream, ointment or dusting powder, that may optionally be in the form of a skin patch.

According to a fourth aspect of the invention there is provided a process for the preparation of a pharmaceutical composition comprising bringing a cholestenoic acid or an inhibitor of an enzyme in the cholestenoic acid biosynthetic or metabolic pathway, and in particular a cholestenoic acid, in conjunction or association with a pharmaceutically or veterinarily acceptable carrier or vehicle.

According to a fifth aspect of the invention there is provided a method of treatment or prevention of neurodegenerative conditions which method comprises modifying the amount of specific cholestenoic acids in an individual. In particular, the amount of 3β,7α-dihydroxycholest-5-en-26-oic (3β,7α-diHCA) is increased, and/or the amount of 3β,7β-dihydroxycholest-5-en-26-oic (3β,7β-diHCA) or 3β-hydroxycholest-5-en-26-oic (3β-HCA) is reduced.

In a particular embodiment, of the fifth aspect, a cholestenoic acid, a cholestenoic acid precursor or an inhibitor of an enzyme in the cholestenoic acid biosynthetic or metabolic pathway, or a pharmaceutically acceptable salt thereof, is administered to an individual in need thereof.

In particular, the method is for treating a neurodegenerative condition. In particular a cholestenoic acid is administered to an individual in need thereof.

Suitable neurodegenerative conditions that may be treated in this way include Parkinson's disease, Alzheimer's disease, mild cognitive impairment (MCI), frontotemporal dementia, dementia, multiple sclerosis, motor neuron disease, Huntingdon's disease, epilepsy, anxiety disorders (including panic disorders and post-traumatic stress disorder (PTSD)), depression, alcohol disorder, drug abuse, growth retardation and cachexia.

In particular, the method of the invention may be used to treat a motor neuron disease. Without being bound by or limited to any classification system, suitable motor neuron diseases treated in this way include but are not limited to amyotrophic lateral sclerosis (ALS), primary lateral sclerosis (PLS), progressive muscular atrophy (PMA), progressive bulbar palsy (PBP), Pseudobulbar palsy (BP), spinal muscular atrophy (SMA), hereditary spastic paresis (HSP) and cerebrotendinous xanthomatosis (CTX). In particular, the method of the invention may be used to treat ALS.

Similarly, the cholestenoic acid or enzyme inhibitor is suitably administered in the form of a pharmaceutical composition as described above.

The amount of cholestenoic acid or enzyme inhibitor administered will vary depending upon factors such as the specific nature of the cholestenoic acid used, the size and health of the patient, the nature of the condition being treated etc. in accordance with normal clinical practice. Typically, a dosage in the range of from 0.01-1000 mg/Kg, for instance from 0.1-10 mg/Kg, would produce a suitable therapeutic effect.

Dosages may be given by constant infusion, in single dose regimens, split dose regimens and/or in multiple dose regimens lasting over several days. Effective daily doses will, however vary depending upon the inherent activity of the active ingredient, such variations being within the skill and judgment of the physician.

The cholestenoic acid or enzyme inhibitor may be used in combination with or alternating with one or more other active agents, such as one or more pharmaceutically active agents or may be integrated into courses of physical treatment modality, such as surgery or physiotherapy In each of the first to fifth aspects of the invention the reagent is preferably the cholestenoic acid, 3β,7α-dihydroxycholest-5-en-26-oic (3β,7α-diHCA).

It is further envisaged that the cholestenoic acid is 3β,7α-dihydroxycholest-5-en-26-oic (3β,7α-diHCA) alone or in combination with 25-hydroxycholesterol (25-HC).

The applicants discovery of the importance of various forms of cholestenoic acid in neurodegenerative conditions also allows for diagnosis of such conditions to be made. Thus, in a sixth aspect of the invention there is provided method for diagnosing or predicting a predisposition towards a neurological disorder, which method comprises determining the absolute or relative amounts of specific forms of cholestenoic acid and/or a cholestenoic acid precursor present in a biological sample, and relating the result to the presence or absence of or a predisposition towards development of a neurological disorder. In particular, the presence or amount of cholestenoic acid selected from 3β,7α-diHCA, 3β,7β-diHCA, 7α,26-diHCO, 7α,26-diHC and 3β-HCA is determined as a basis of the diagnostic method. In accordance with the work reported here, it is assumed that a lack of or reduction in the levels of any of these or elevated levels of 3β-HCA or 3β,7β-diHCA, may be indicative of a neurodegenerative condition.

In a seventh aspect, the invention provides the use of a cholestenoic acid and/or a cholestenoic acid precursor as a diagnostic biomarker for the degree of or progression of CNS disease or a predisposition to CNS disease including but not limited to a neurodegenerative condition as described above. In accordance with normal practice, the level of the specific cholestenoic acid used as such a biomarker may be compared to levels found in samples from normal individuals either once or repeatedly and variance of this amount may be interpreted as being an indicator of the presence of or likelihood of or progression of disease or as an index of therapeutic response or for the stratification of patients in clinical trials. In particular, the cholestenoic acid is selected from those listed above.

BRIEF DESCRIPTION OF THE FIGURES

An embodiment of the invention will now be described by way of example only with reference to the accompanying figures and Tables in which.

The firefly luciferase activity was normalized to *Renilla luciferase* activity, and the values are expressed as fold activation over the normalized basal Lxr or Fxr response element-luciferase activity set to 1. Data are means±SE (n=3), *, p<0.05; **, p<0.01 compared with vehicle treatment. Additional analysis was performed on the compounds 5α-cholestan-3β-ol, 5α-cholestan-3-one, cholest-4-en-3-one, cholesta-4,6-dien-3-one, 7α-hydroxycholesterol, 7α-hydroxycholest-4-en-3-one, 7β-hydroxycholesterol, and 7α,12α-dihydroxycholest-4-en-3-one which are found at elevated levels in plasma of CTX patients. None of these compounds showed significant activity in the luciferase assay. Panel D shows a time-resolved (TR)-FRET Lxrβ coactivator assay used to determine the binding affinity of cholestenoic acids towards the Lxrβ-LBD. Data are means±SEM (n=3) and * represents significant difference (p<0.05) compared with vehicle treatment for cholestenoic acid concentrations of 10 μM and higher. Concentration is plotted on a log scale. Panel E illustrates that 3β,7α-diHCA, 3β,7β-diHCA and 3β-HCA induce significant increases in Abca1, Abcg1, and Srebf1 in SN4741 cells. Data are means±SE (n=3), *, p<0.05; **, p<0.01 compared to vehicle treatment.

Figure 3:
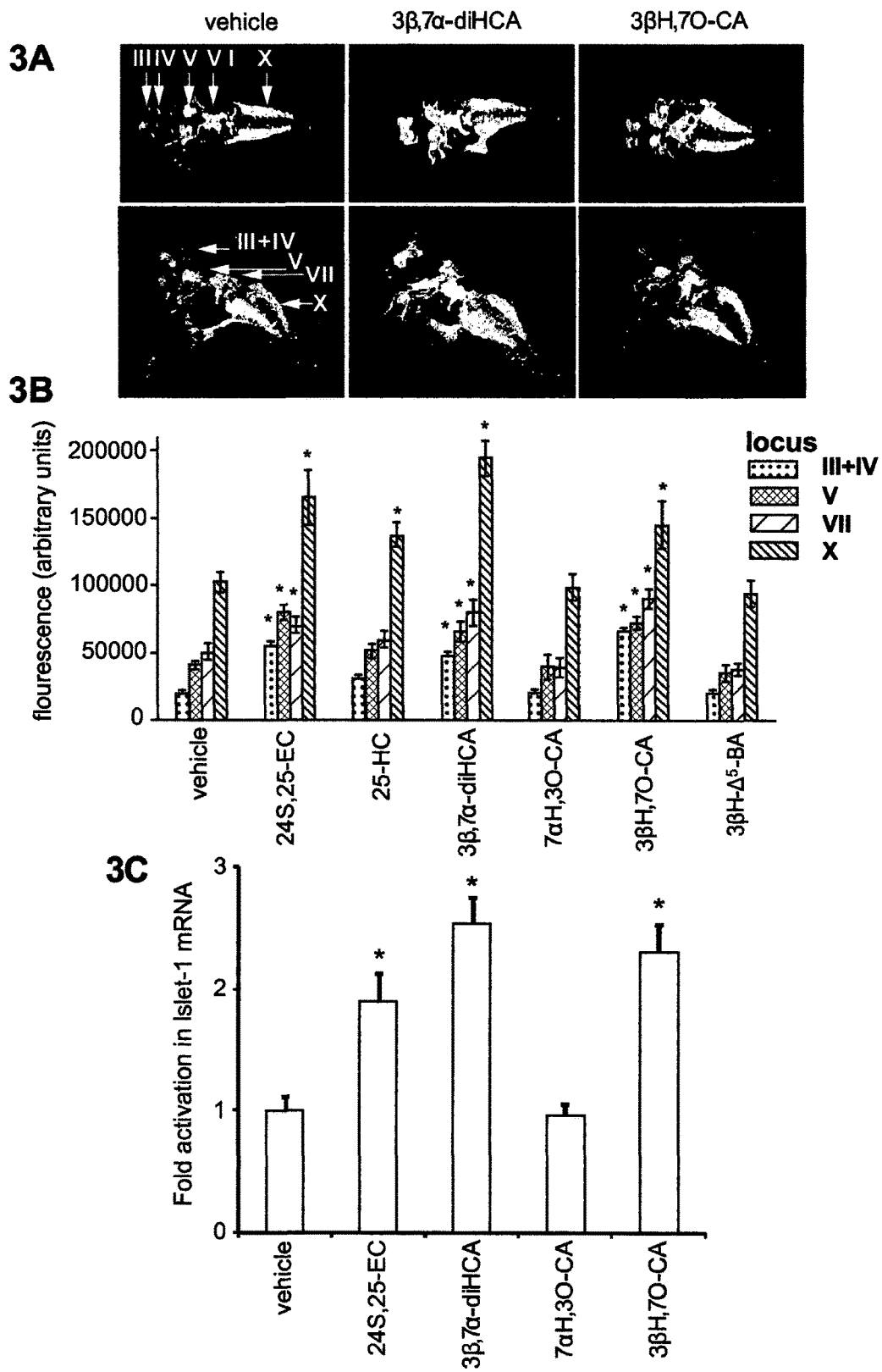
Figure 3:
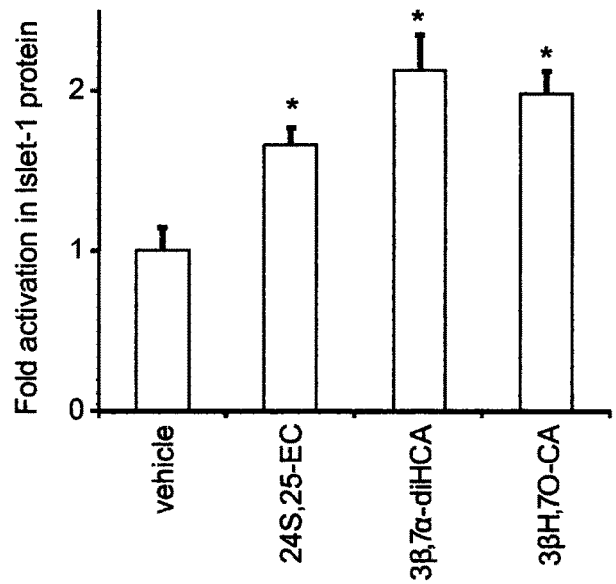
Figure 3:
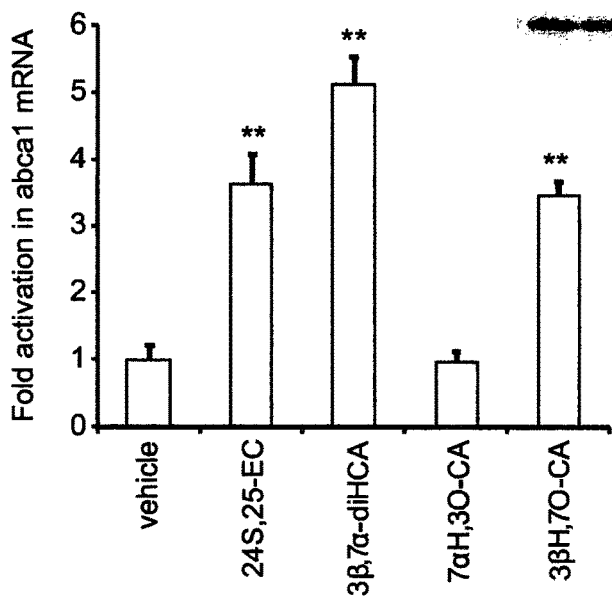

FIG. 3 shows: Green fluorescent protein (GFP) and abca1 expression in motor neurons in Tg[Isl1:GFP] embryos 48 h post fertilization (hpf). Embryos were incubated with 10 μM test compound or vehicle added to medium, and the medium was replaced every 12 h with fresh solution (containing test compound or vehicle) Immunocytochemistry was performed using an anti-GFP antibody. In panel 3A one sees dorsal (upper panel) and dorsolateral (lower panel) views of the head/upper back region of embryos treated with vehicle, 3β,7α-dihydroxycholest-5-en-26-oic (3β,7α-diHCA) or 3β-hydroxy-7-oxocholest-5-en-26-oic (3βH,7O-CA) acid. Arrows indicate loci III, IV, V, VII and X. In panel 3B there is quantification of Islet-GFP signal intensity in the different cranial nerves/loci. 24S,25-Epoxycholesterol (3β-hydroxycholest-5-en-24S,25-epoxide, 24S,25-EC) was used as a positive control. Data are means±SE (n=4), *, p<0.05 compared to each respective locus of vehicle-treated zebrafish.

In panel 3C one sees Islet-1 mRNA levels, in panels 3D and 3E Islet-1 one sees protein levels (quantification and representative blot) and in panel 3F one sees abca1 mRNA levels, after treatment of zebrafish with the compounds indicated. Data are means ±SE (n=3), *, p<0.05; **, p<0.01 compared to vehicle-treated zebrafish. Other test compounds: 25-hydroxycholesterol (25-HC); 7α-hydroxy-3-oxocholest-4-en-26-oic acid (7αH,3O-CA); 3β-hydroxychol-5-en-24-oic acid (3βH-Δ$^5$-BA). The cranial nerves (III, IV, V, VII, X) in the zebrafish are evolutionarily homologous to those in humans. Locus III contains the oculomotor neurons, IV contains trochlear neurons, V the trigeminal motor neurons, VII the facial motor neurons and X the cell bodies of the vagus nerve.

Figure 4:
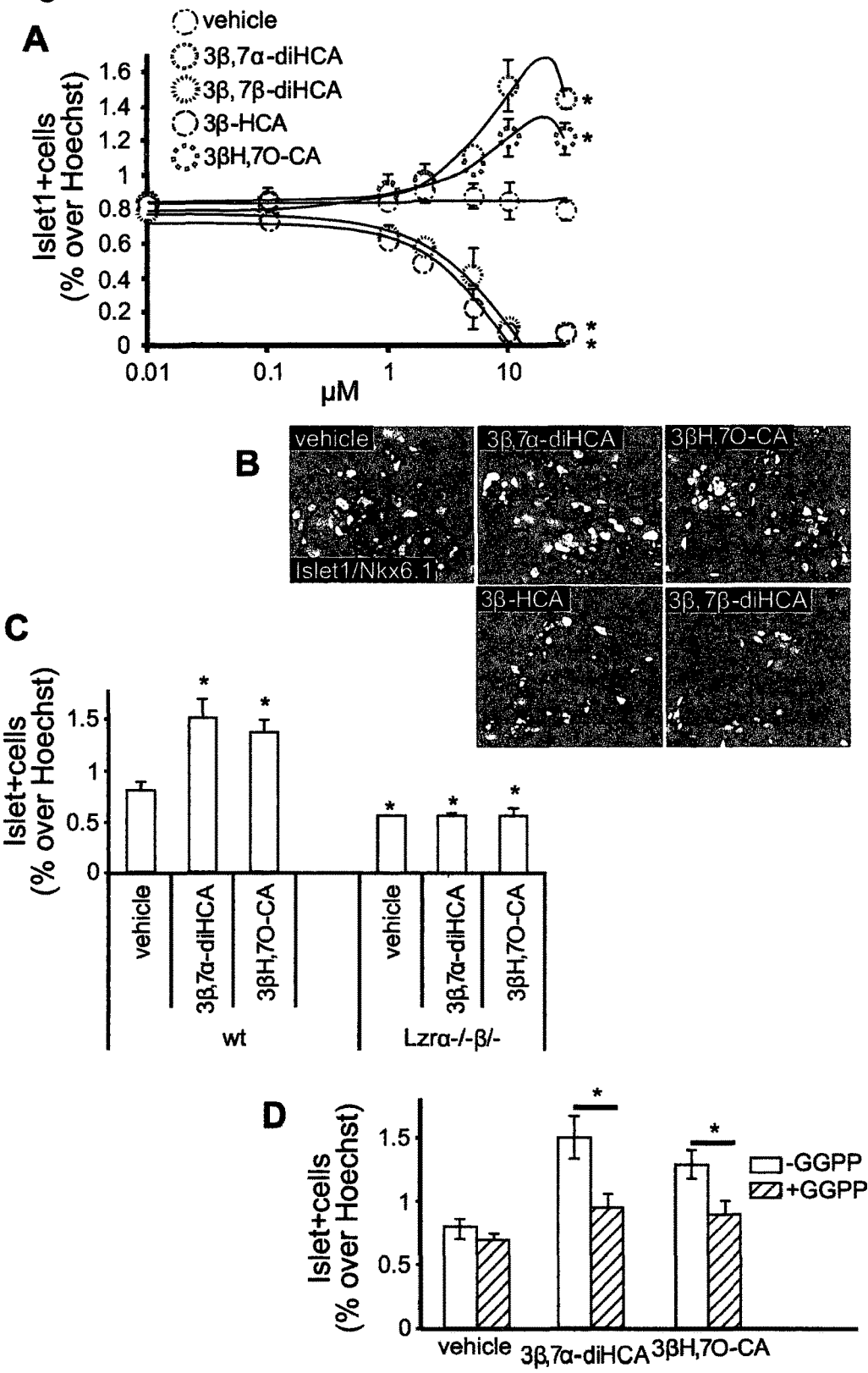
Figure 4:
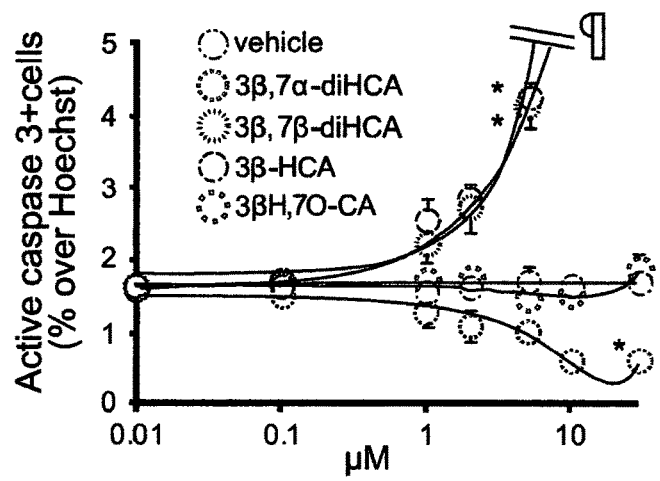
Figure 4:
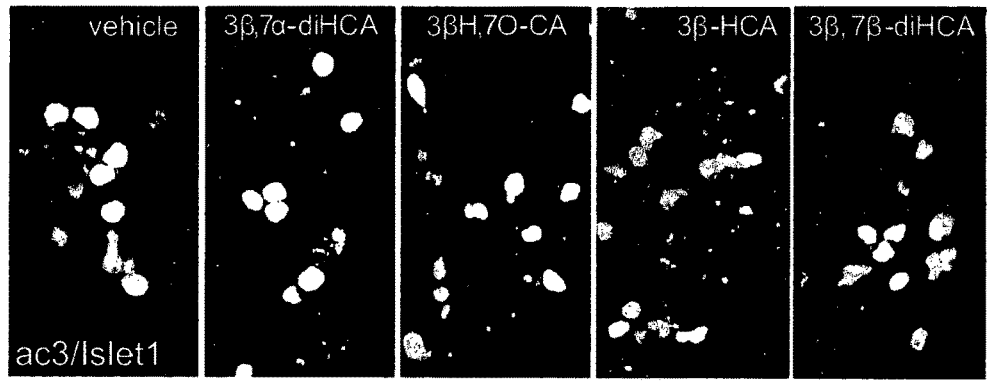
Figure 4:
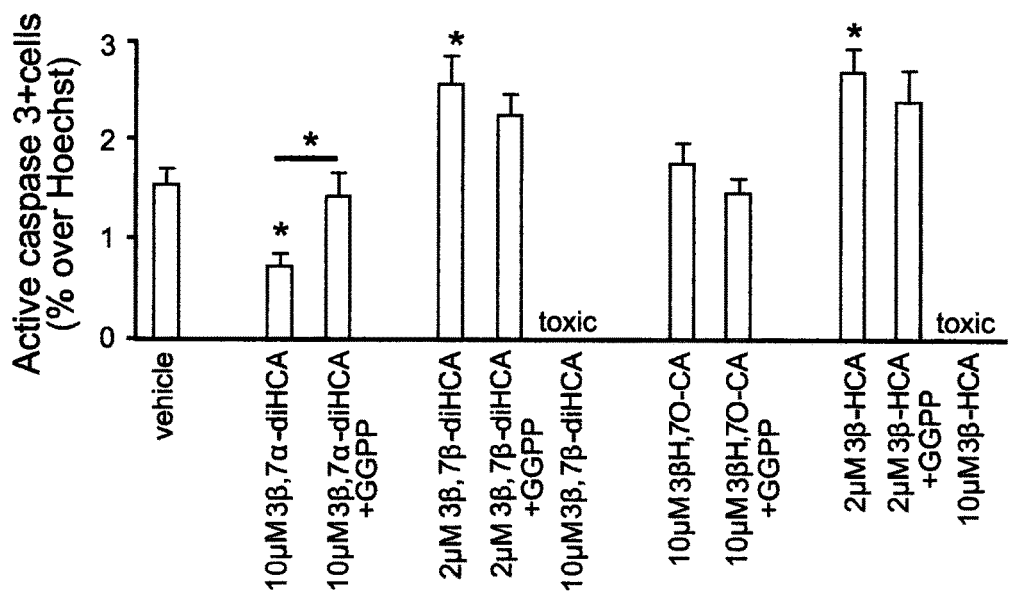
Figure 4:
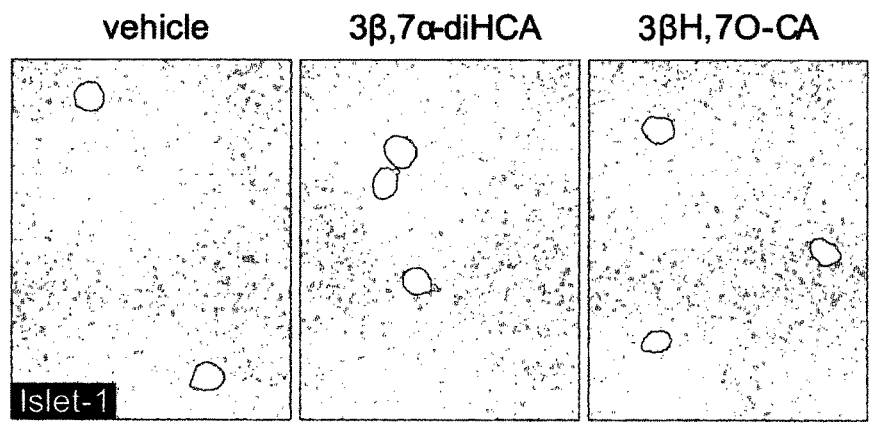
Figure 4:
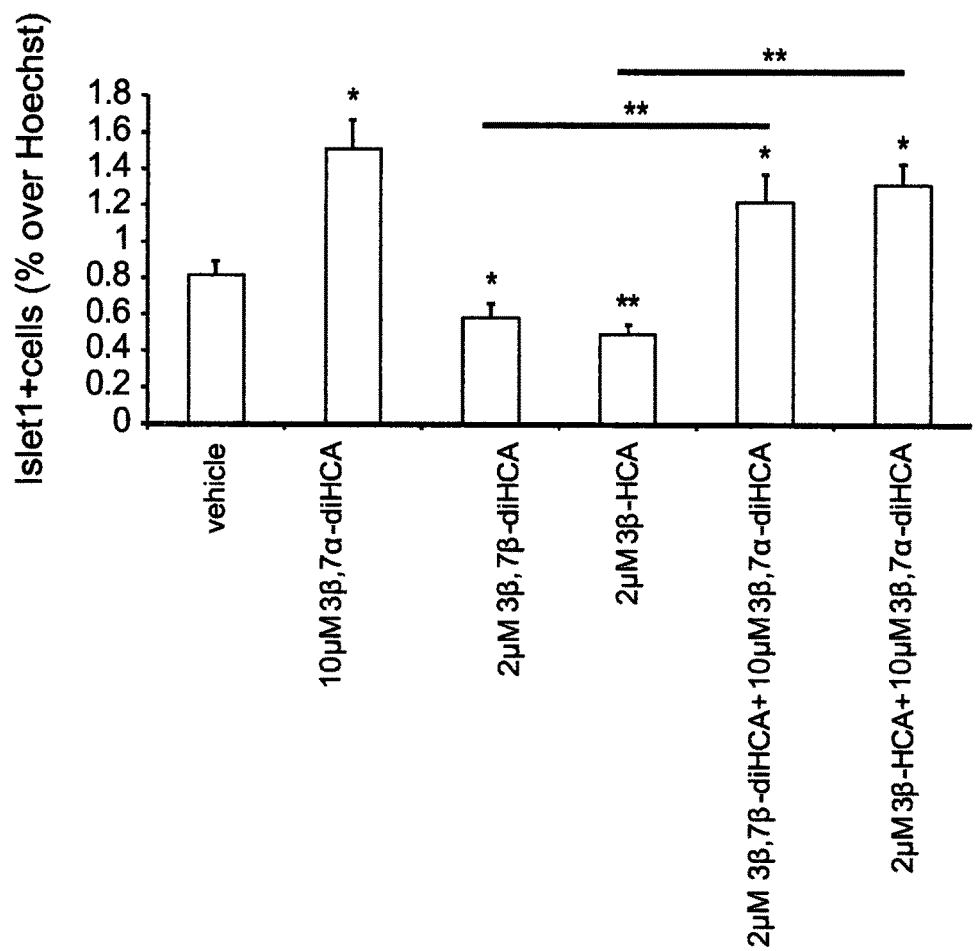

FIG. 4 shows: specific cholestenoic acids increase the number of Islet1+ oculomotor neurons, have a neuronal survival effect, or are toxic in mouse E11.5 brain primary cultures. Panel A shows dose-response curves for the quantification of Islet1+ cells in mouse E11.5 brain primary cultures from wild type (wt) embryos treated with 3β,7α-dihydroxycholest-5-en-26-oic (3β,7α-diHCA), 3β,7β-dihydroxycholest-5-en-26-oic (3β,7β-diHCA), 3β-hydroxycholest-5-en-26-oic (3β-HCA) or 3β-hydroxy-7-oxocholest-5-en-26-oic (3βH,7β-CA) acids. Concentration is plotted on a log scale. Data are means±SEM (n=3). * represents significant difference (p<0.05) compared with vehicle treatment for concentrations of 5 μM and higher of 3β,7α-diHCA, 10 μM and higher of 3βH,7O-CA, 2 μM and higher of 3β,7β-diHCA, and 2 μM and higher of 3β-HCA. Panel B shows representative images of Islet-1 and Nloc6.1 stained cell nuclei; 3β,7α-diHCA and 3(3H,7O-CA were at 10 μM, 3β,7β-diHCA and 3β-HCA were at 2 μM. In panel C there is quantification of Islet1+ cells in mouse E11.5 brain primary cultures from wild type (wt) or Lxrα-/-β-/- embryos treated with 3β,7α-dihydroxycholest-5-en-26-oic acid (3β,7α-diHCA) or 3β-hydroxy-7-oxocholest-5-en-26-oic acid (3βH,7β-CA). Data are means±SE (n=3), *, p<0.05 compared to vehicle wt group. Panel D shows the effect of the Lxr antagonist geranylgeranyl pyrophosphate (GGPP, 10 μM) on the treatments in the wt group. Data are means±SE (n=3), *, p<0.05 compared to '-GGPP' group as indicated. Panel E shows dose-response curves for the quantification of active caspase 3+ cells in mouse E11.5 brain primary cultures (wt group). Concentration is plotted on a log scale. The symbol ¶ indicates very high cell death in the cultures. Data are means±SEM (n=3). * represents significant difference (p<0.05) compared with vehicle treatment for concentrations of 10 μM and higher of 3β,7α-diHCA, 2 μM and higher of 3β,7β-diHCA, and 2 μM and higher of 3β-HCA. Panel F shows representative images of active caspase 3 and Islet-1 stained cell nuclei. 3β,7α-diHCA and 3βH,3β-CA were at 10 μM, 3β,7β-diHCA and 3β-HCA were at 2 μM. In panel G one sees quantification of active caspase 3+ cells in mouse E11.5 brain primary cultures (wt group) treated with 2 or 10 μM of the acids as indicated, with or without 10 μM GGPP. Data are means±SE (n=3), *, p<0.05 compared to vehicle treatment or compared to '-GGPP' group as indicated. In panel 4J 3β,7α-diHCA reduces the toxic effect of 3β,7β-diHCA or 3β-HCA on Islet1+ cells in mouse E11.5 brain primary cultures (wt group). 10 μM 3β,7α-diHCA reverses the loss of Islet1+ cells in the cultures treated with either 2 μM 3β,7O-diHCA or 3β-HCA. Data represent mean±SE (n=3), *, p<0.05; **, p<0.01 compared to vehicle treatment, or as indicated. Panel 4H also shows representative images of Islet-1 stained cell nuclei.

Figure 5:
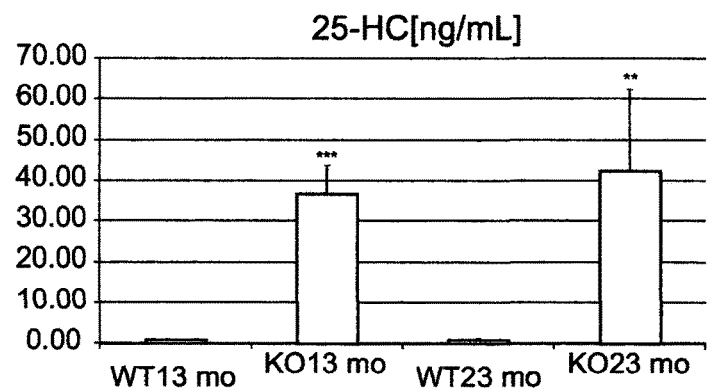
Figure 5:
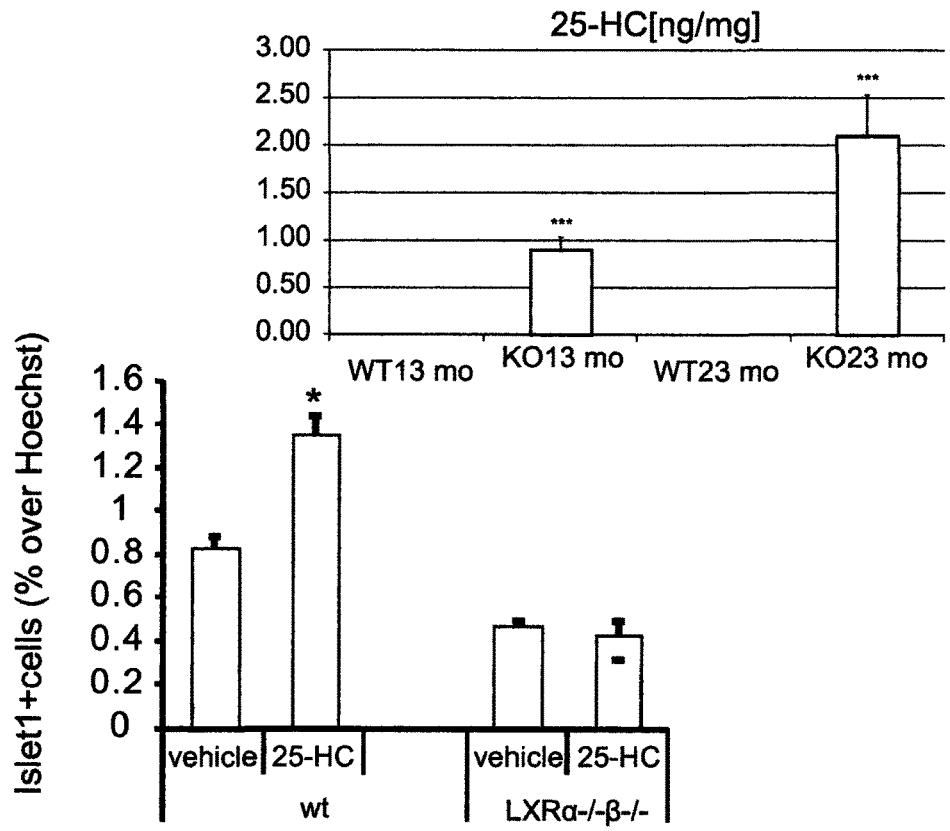
Figure 5:
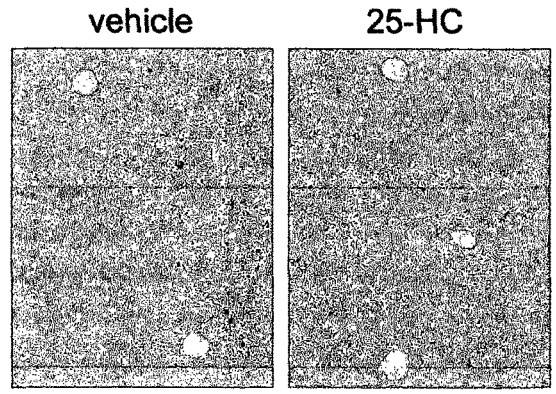
Figure 5:
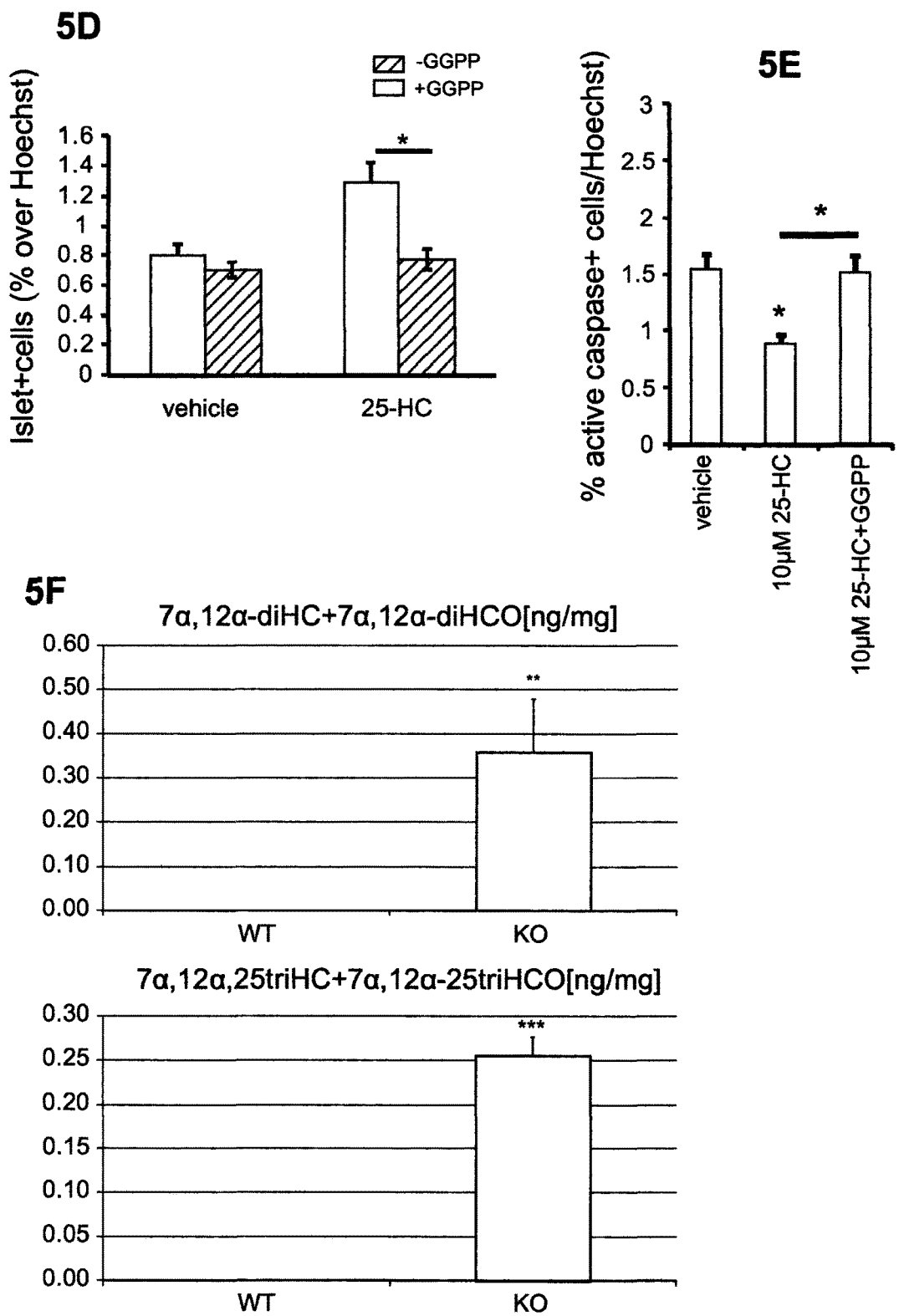

FIG. 5 shows: 25-Hydroxycholesterol is increased in Cyp7b1−/− mouse brain and plasma, increases the number of Islet+ oculomotor neurons and has a neuronal survival effect in mouse E11.5 brain primary cultures. Panel 5A: Levels of 25-hydroxycholesterol (25-HC) in plasma (ng/mL, upper panel) and whole brain (ng/mg, lower panel) from 13 month and 23 month male mice. For plasma analysis n=5 for both wild type (WT) and Cyp7b1 knockout (KO) 13 month mice and n=4 for the 23 month mice. For brain analysis n=3 for WT and KO 13 month mice and n=4 for 23 month mice. Panel 5B: Quantification of Islet1+ cells in mouse E11.5 brain primary cultures from wild type (wt) or Lxrα−/−β−/− embryos treated with 25-HC. Data are means±SE (n=3), *, p<0.05 compared to vehicle wt group. Panel 5C: Representative images of Islet-1 stained cell nuclei, and panel 5D the effect of the Lxr antagonist geranylgeranyl pyrophosphate (GGPP, 10 μM) on the treatments in the wt group. Panel 5E: Quantification of active caspase 3+ cells in mouse E11.5 brain primary cultures (wt group) treated with 10 μM of 25-HC with or without 10 μM GGPP. Data are means±SE (n=3), *, p<0.05 compared to vehicle treatment or compared to "-GGPP" group as indicated. Panel 5F: Levels of (upper plot) 7α,12α-dihydroxycholesterol (7α,12α-diHC) plus 7α,12α-dihydroxycholest-4-en-3-one (7α,12α-diHCO) and (lower plot) cholest-5-ene-3β,7α,12α,25-tetrol (7α,12α,25-triHC) plus 7α,12α,25-trihydroxycholest-4-en-3-one (7α,12α,25-triHCO) in whole brain (ng/mg) from 3 month male mice (n=3). In panels 5A and 5F 25-HC, 7α,12α-diHC, 7α,12α-diHCO, 7α,12α,25-triHC and 7α,12α,25-triHCO were identified and quantified by LC-ESI-MS' following charge-tagging with GP-hydrazine. In the absence of authentic standards 7α,12α,25-triHC and 7α,12α,25-triHCO were presumptively identified by exact mass, retention time and $MS^3$ spectra. Data are means±SD, , p<0.01; *, p<0.001 compared to WT.

Figure 6:
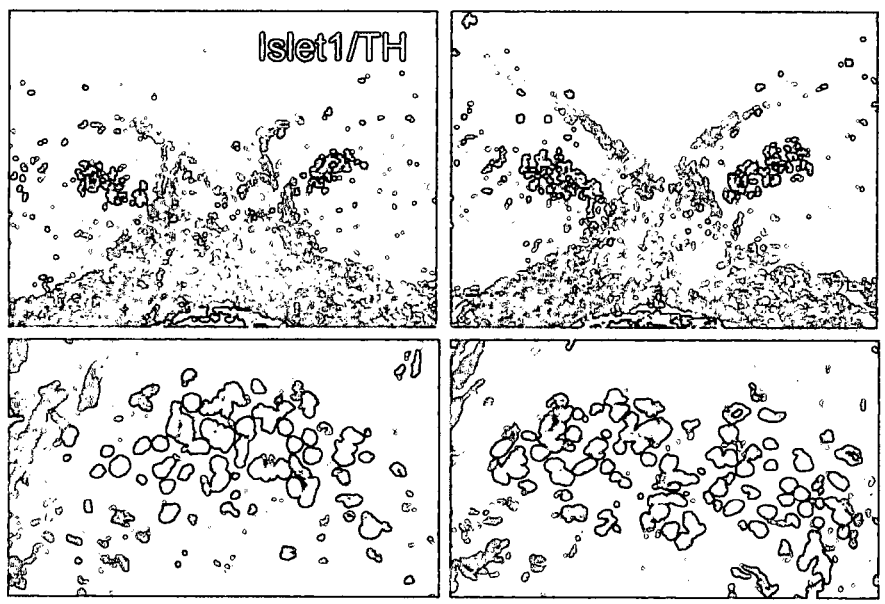
Figure 6:
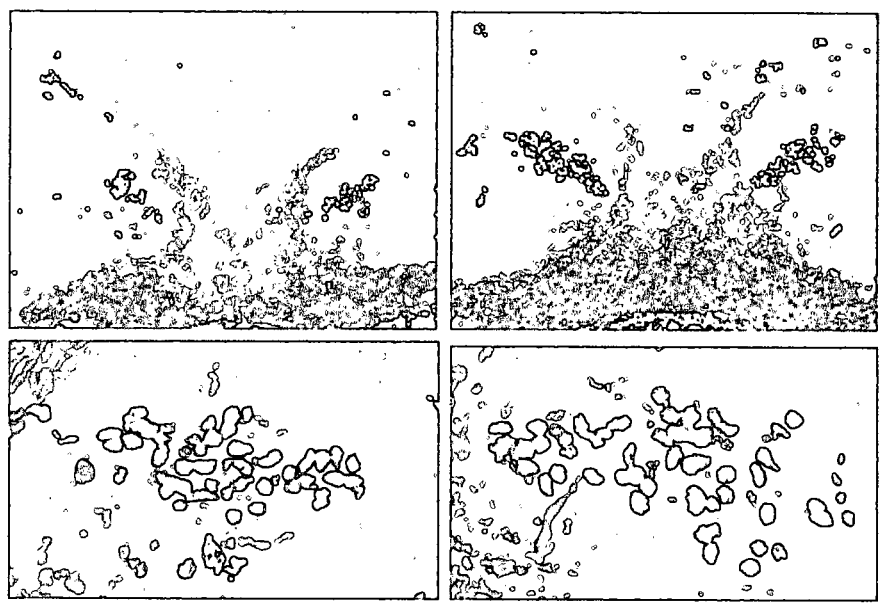

FIG. 6 illustrates the competition between the effects of the different cholestenoic acids and demonstration that 3β,7α-diHCA promotes motor neuron survival in vivo. Panel A shows the results of a time-resolved (TR) FRET Lxr coactivator assay. The effect of 3β,7α-dihydroxycholest-5-en-26-oic acid (3β,7α-diHCA) (at 10 μM) was dose dependently competed by 3β,7β-dihydroxycholest-5-en-26-oic acid (3β,7β-diHCA) and 3β-hydroxycholest-5-en-26-oic (3β-HCA). Data are means±SEM (n=3). * represents significant difference (p<0.05) compared with 10 μM 3β,7α-diHCA treatment for concentrations of 2 μM and higher of '3β,7α-diHCA+3β,7β-diHCA' and 5 μM and higher of '3β,7α-diHCA+3β-HCA'. Concentration is plotted on a log scale. Panels B and C show how 10 μM 3β,7α-diHCA rescues the toxic effect of 2 μM 3β,7β-diHCA or 3β-HCA on Islet+ cells and reduces neuronal cell death induced by these acids as indicated by the number of active caspase 3+ cells in mouse E11.5 brain primary cultures. Data represent mean±SEM (n=3), *, p<0.05; **, p<0.01 as indicated. Panel D shows the results of an experiment in which the cholestenoic acids 3β,7α-diHCA, 3β-HCA, or 3β-HCA and 3β,7α-diHCA were injected into the cerebral aqueduct of E11.5 mice in utero and coronal brain sections were analyzed at E13.5 for Islet1+ cell numbers. Data are means±SE (n=3), *, p<0.05; **, p<0.01 as indicated. Panel E shows representative images of coronal sections of E13.5 mouse embryo brains (upper images) after in utero injections. Higher magnification images (lower images) of the oculomotor nuclei for each of the treatment groups.

Figure 7:
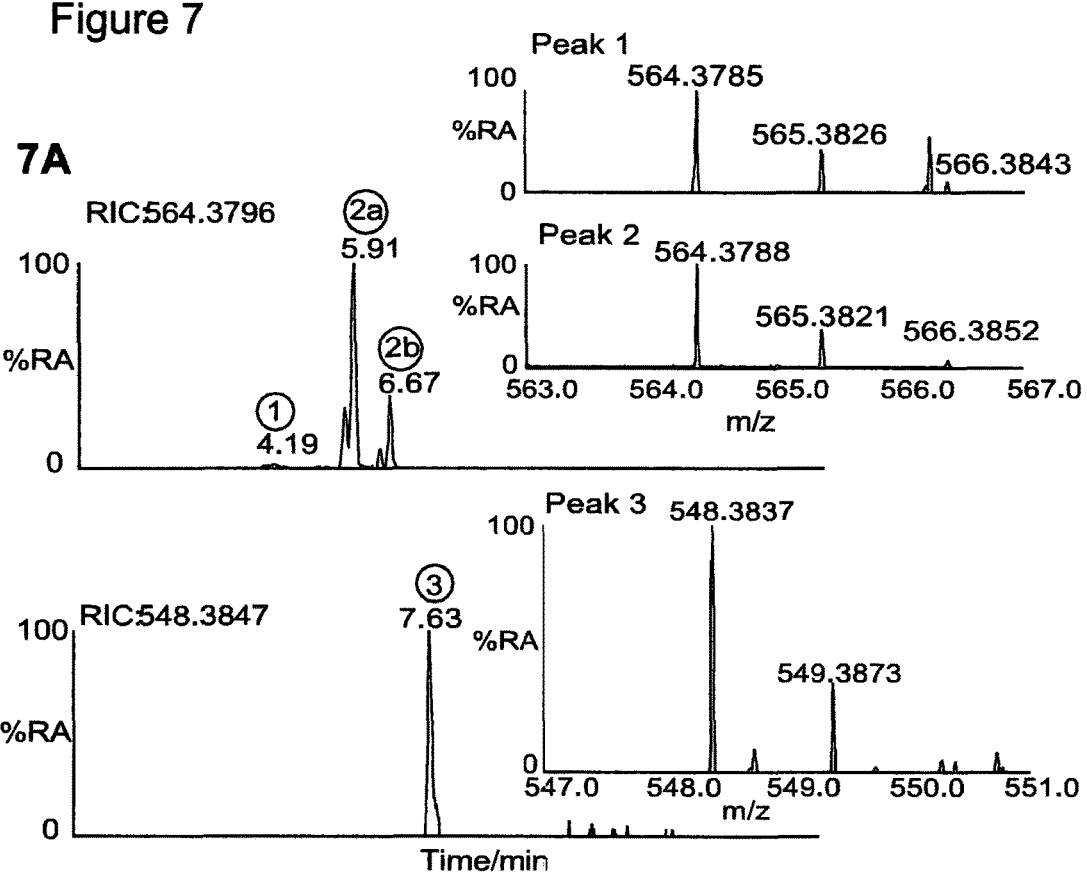
Figure 7:
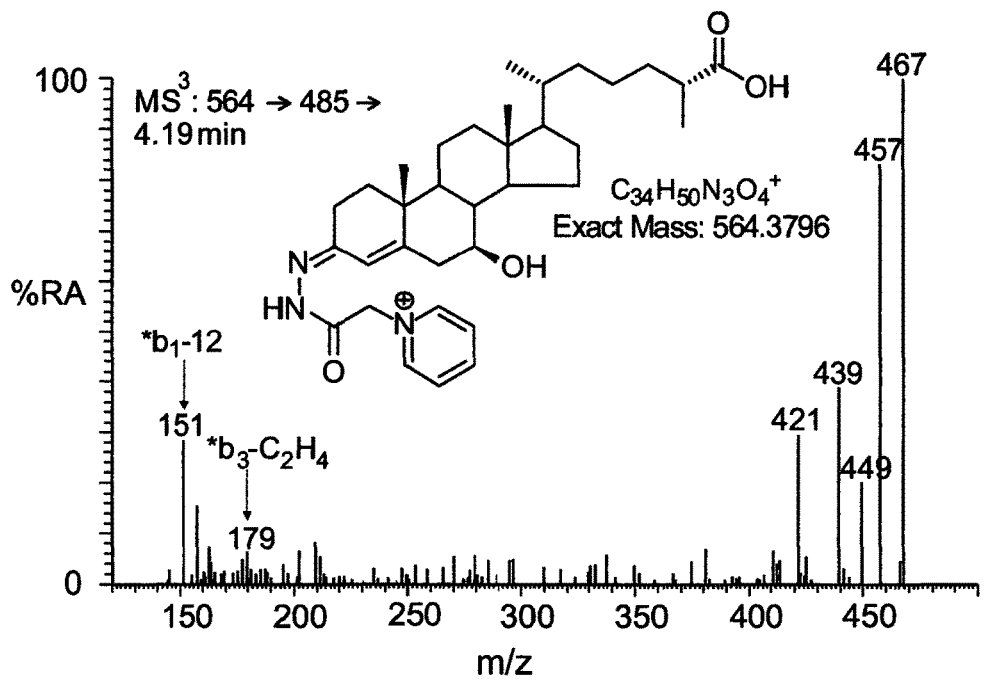
Figure 7:
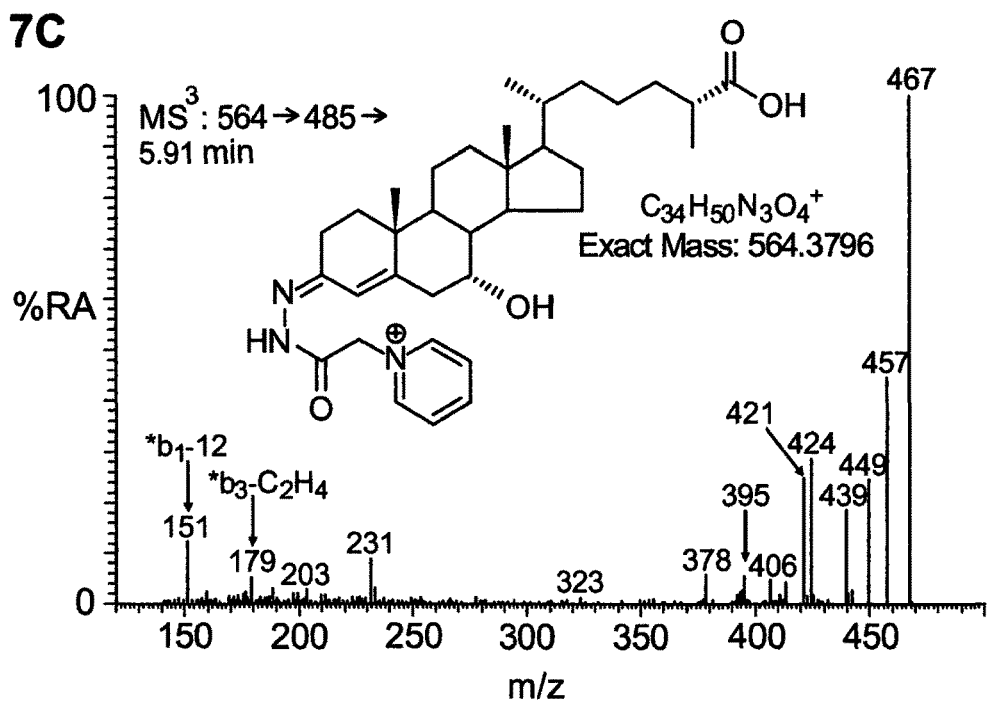
Figure 7:
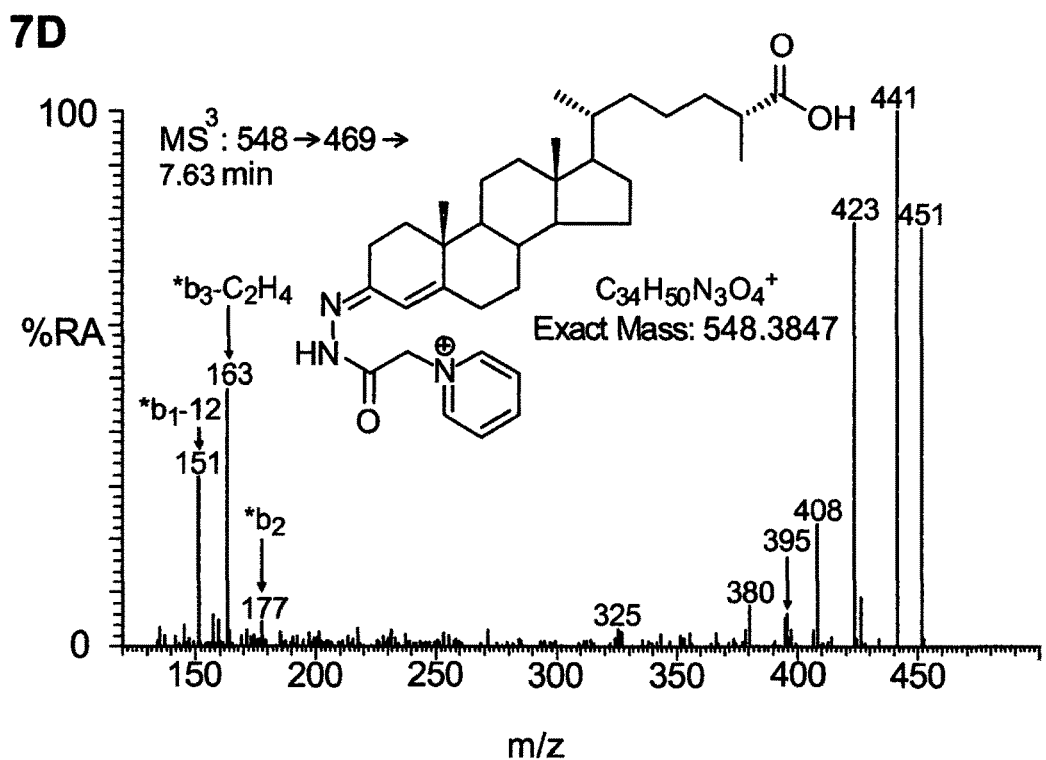

FIG. 7: Panel 7A shows LC-ESI-MS reconstructed ion chromatograms (RICs±5 ppm) of the cholestenoic acids: 3β,7β-dihydroxycholest-5-en-26-oic (3β,7β-diHCA, peak 1), 7α-hydroxy-3-oxocholest-4-en-26-oic/3β,7α-dihydroxycholest-5-en-26-oic (7αH,3O-CA/3β,7α-diHCA peaks 2) and 3β-hydroxycholest-5-en-26-oic (3β-HCA, peak 3) acid. The insets show the molecular ions corresponding to the peaks 1, 2a and 3. Sterols were extracted from CSF in ethanol, fractionated according to hydrophobicity by SPE and "charge-tagged" with the GP reagent to give maximum sensitivity upon LC-ESI-MS analysis. The first step of the charge-tagging process involves oxidation of 3β-hydroxy-5-ene groups to 3-oxo-4-enes by cholesterol oxidase from Streptomyces sp. Endogenous 3-oxo-4-ene containing compound are differentiated from those derived from 3β-hydroxy-5-enes by repeating the charge tagging reactions, but in the absence of oxidizing enzyme. The charge-tagging process introduces syn and anti conformers (peaks a and b) which may or may not be resolved. Panels 7B, 7C, and 7D present LC-ESI-$MS^3$ spectra of the three acids in panel 7A. Structures of the ions fragmented by $MS^3$ ([M]$^+$→[M-79]$^+$→) are shown. Fragmentation nomenclature has been described previously. The retention times and $MS^3$ spectra are identical to those of authentic standards. Spectra were recorded on the LTQ-Orbitrap. In this work the applicants have adopted the sterol nomenclature recommended by the lipid maps consortium, where 26-hydroxycholesterol refers to cholest-(25R)-5-en-33,26-diol, and similarly, carboxylic acids which introduce 25R stereochemistry to the side-chain are at C-26.

Figure 8:
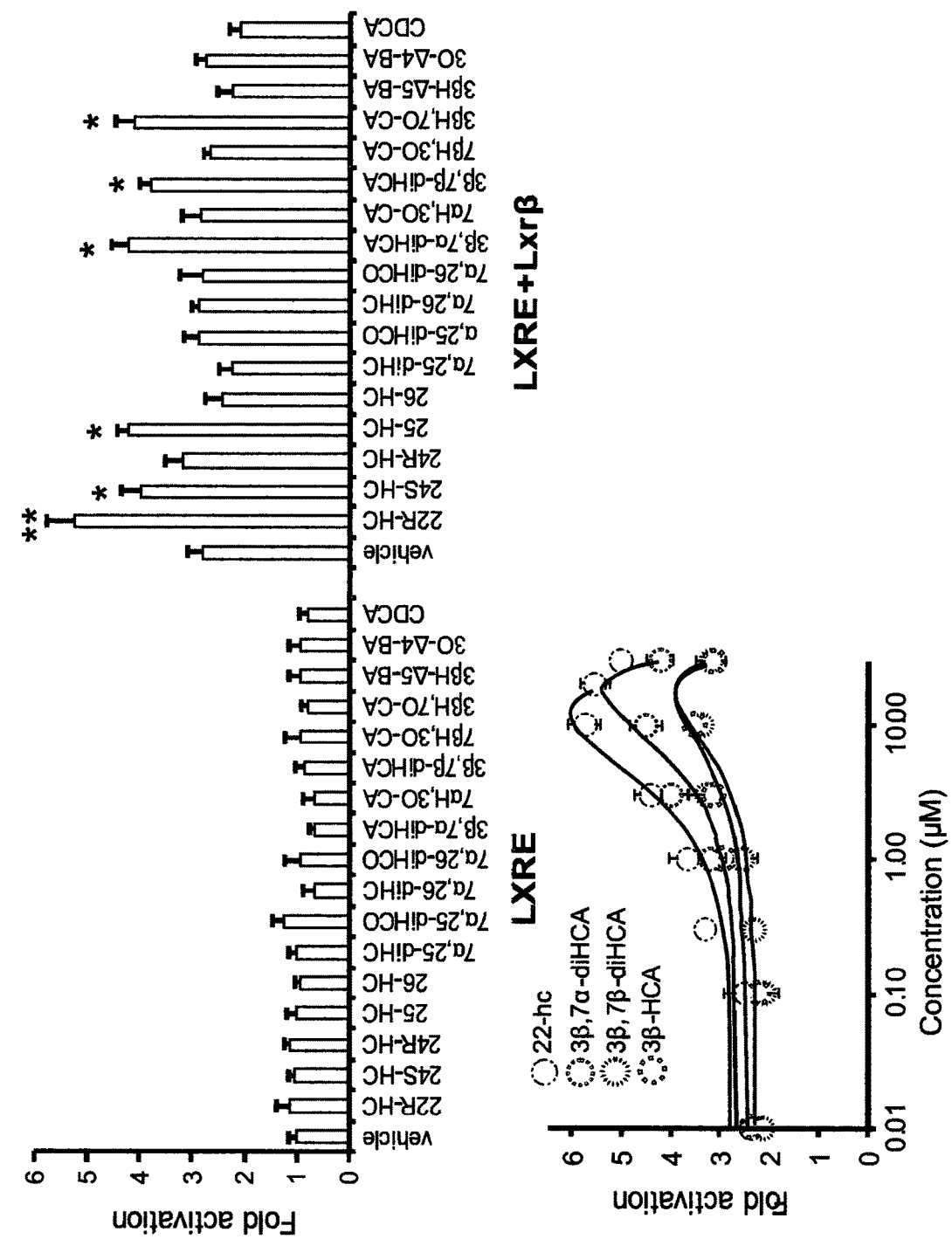
Figure 8:
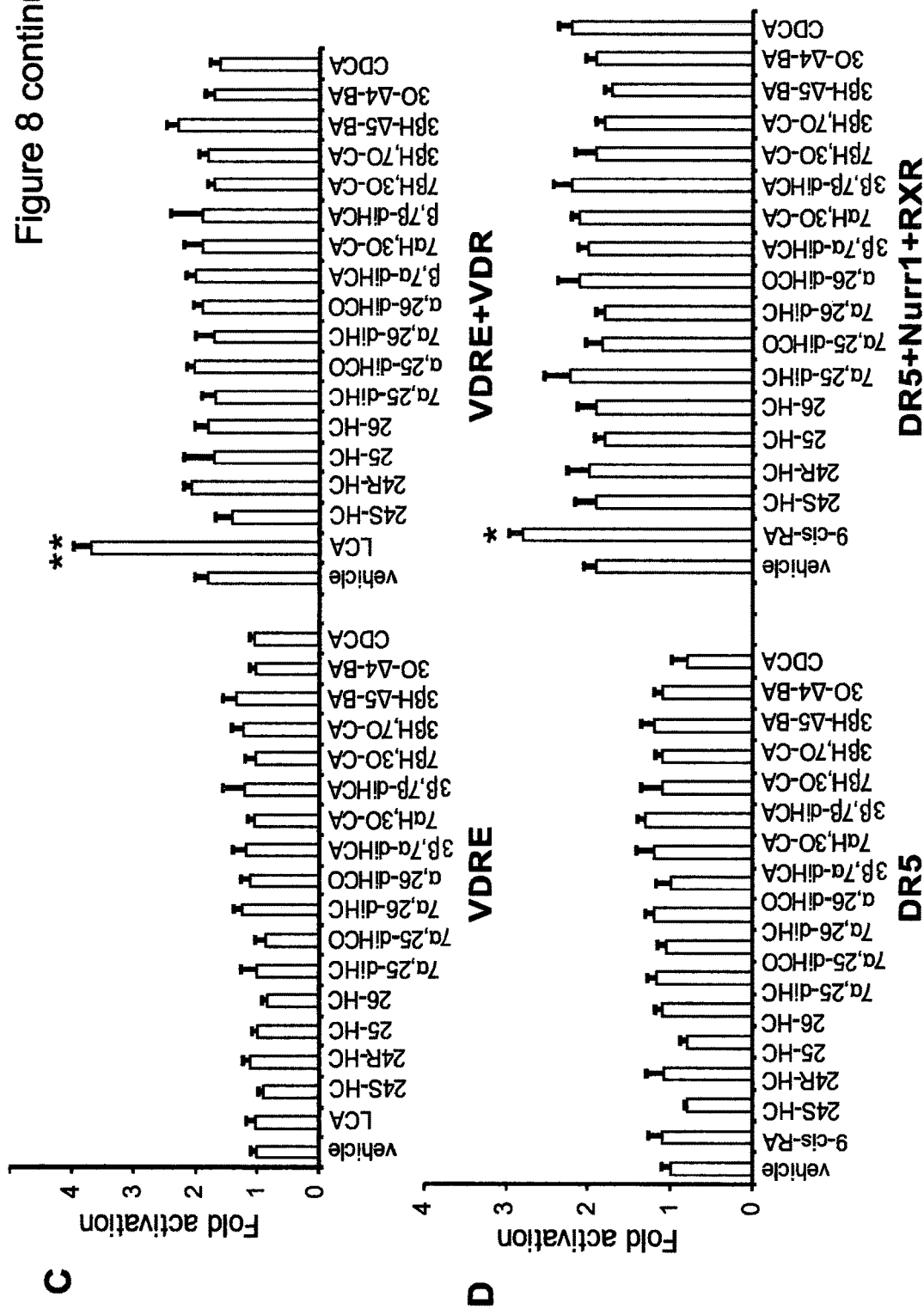

FIG. 8: shows an analysis of the nuclear receptor activational capacity of oxysterols and cholestenoic acids (10 μM). Panel A: Analysis of luciferase activity in SN4741 cells transfected with an Lxr responsive luciferase reporter construct (Lxre) and Lxrβ and stimulated for 24 h with 22R-hydroxycholesterol (22R-HC), a known Lxrβ ligand, or the compounds indicated. Panel B shows dose response curves for the activational capacity of cholestenoic acids on Lxrβ. Concentration is plotted on a log scale. Similar experiments were performed with cells transfected with Vdre and Vdr (see panel C); and DR5 and Nurr1 (see panel D). Lithocholic acid (LCA) is a known Vdr ligand. 9-Cis-retinoic acid (9-cis-RA) is a known Rxr ligand. Rxr is the heterodimer partner of Nurr1. Other compounds tested were 24S-hydroxycholesterol (24S-HC); 24R-hydroxycholesterol (24R-HC); 25-hydroxycholesterol (25-HC); 26-hydroxycholesterol (26-HC); 7α,25-dihydroxycholesterol (7α,25-diHC); 7α,25-dihydroxycholest-4-en-3-one (7α,25-diHCO); 7α,26-dihydroxycholesterol (7α,26-diHC); 7α,26-dihydroxycholest-4-en-3-one (7α,26-diHCO); 3β,7α-dihydroxycholest-5-en-26-oic acid (3β,7α-diHCA); 7α-hydroxy-3-oxocholest-4-en-26-oic acid (7αH,3O-CA); 3β,7β-dihydroxycholest-5-en-26-oic acid (3β,7β-diHCA); 7β-hydroxy-3-oxocholest-4-en-26-oic acid (7βH,3O-CA); 3β-hydroxy-7-oxocholest-5-en-26-oic acid (3βH,7O-CA); 3β-hydroxychol-5-en-24-oic acid (3βH-Δ$^5$-BA), 3-oxochol-4-en-24-oic acid (3O-Δ$^4$-BA); chenodeoxycholic acid (CDCA). The firefly luciferase activity was normalized to Renilla luciferase activity, and the values are expressed as fold activation over the normalized basal Lxr response element-luciferase activity set to 1. Data are means±SE. (n=3), *, p<0.05; **, p<0.01 compared with vehicle treatment.

Figure 9:
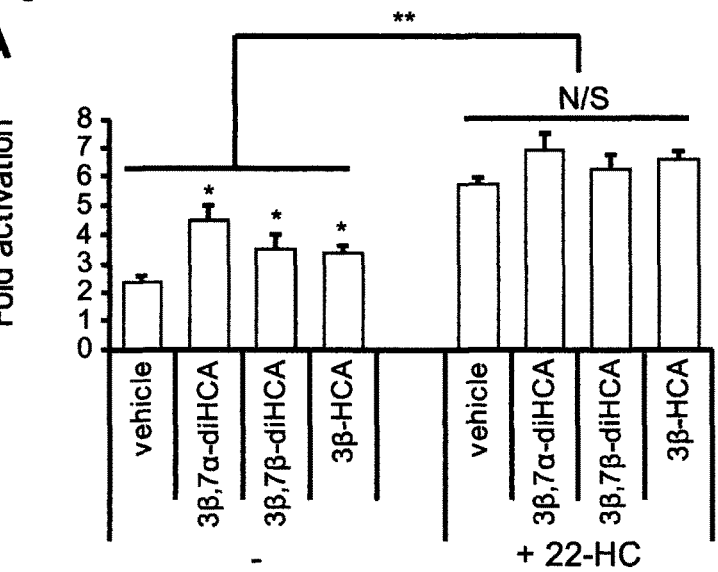
Figure 9:
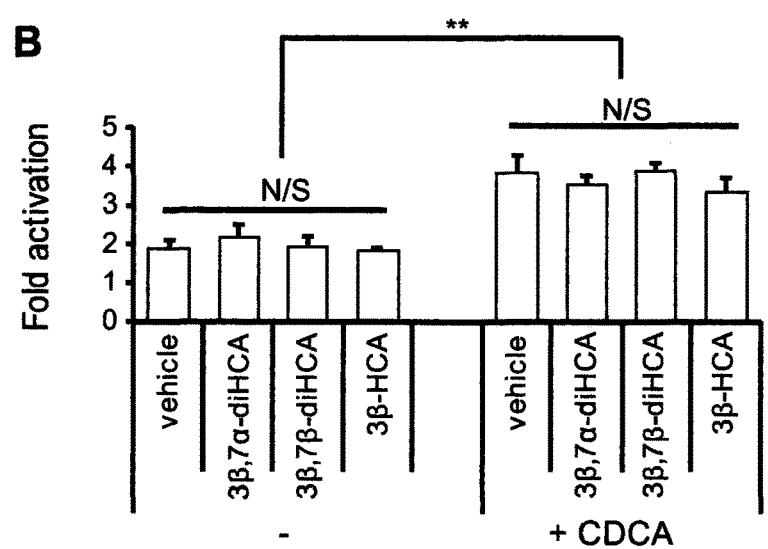
Figure 9:
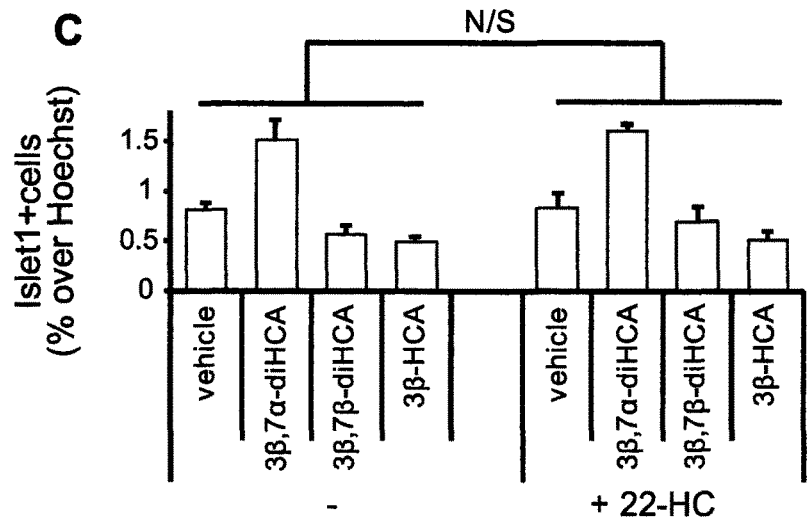

FIG. 9 shows the effects of cholestenoic acids in combination with other nuclear receptor agonists. Panel A Lxrβ activational capacity of 3β,7α-dihydroxycholest-5-en-26-oic (3β,7α-diHCA), 3β,7β-dihydroxycholest-5-en-26-oic (3β,7β-diHCA) and 3β-hydroxycholest-5-en-26-oic (3β-HCA) acids (10 μM) in combination with 22R-hydroxycholesterol (22-HC, 10 μM). In panel B similar experiments performed with Fxr, the three cholestenoic acids and chenodeoxycholic acid (CDCA, 10 μM). The experiments in panels A and B were performed otherwise as in FIG. 8. In panel C, quantification of Islet1+ cells in mouse E11.5 brain primary cultures treated with 10 μM 3β,7α-diHCA, 2 μM 3β,7β-diHCA or 2 μM3β-HCA in combination with 22-HC. Data are means±SE (n=3), *, p<0.05; **, p<0.01 as indicated.

Figure 10:
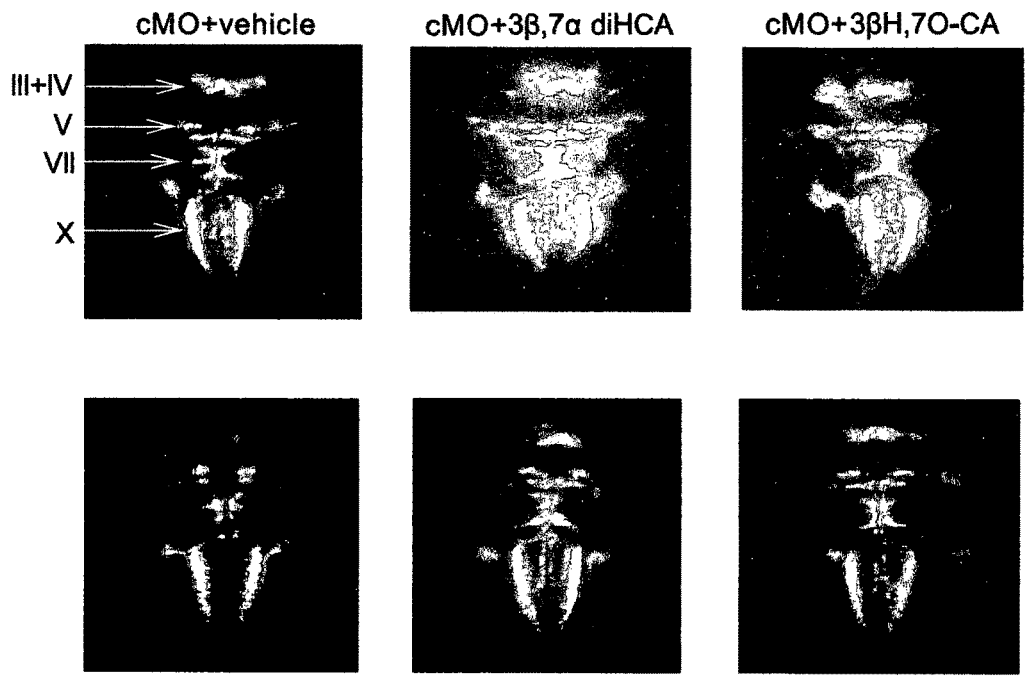
Figure 10:
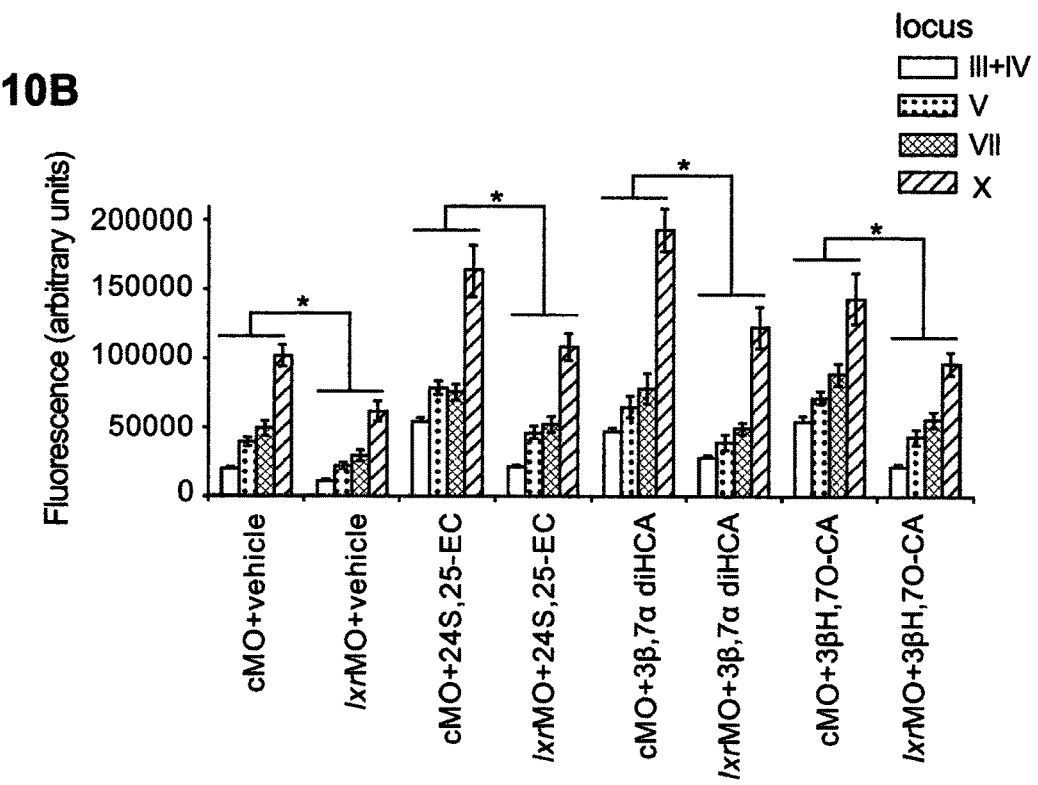

FIG. 10 shows 3β,7α-diHCA and 3βH,7O-CA require lxr for expression of motor neuron markers in zebrafish. Panel 10A: lxr morpholinos (lxr MO) abolished the effects of the two acids on Islet-1 expression. Control scrambled MO (cMO, upper panel) or lxr MO (lower panel) injected Tg[Isl1:GFP] embryos were incubated with 10 μM test compound or vehicle added to medium, and the medium was replaced every 12 h with fresh solution (containing test compound or vehicle) Immunocytochemistry was performed using an anti-GFP antibody. Dorsal views of the head/upper back region of embryos treated with vehicle, 3β,7α-dihydroxycholest-5-en-26-oic (3β,7α-diHCA) or 3β-hydroxy-7-oxocholest-5-en-26-oic (3βH,7O-CA) are shown. Arrows indicate loci III, IV, V, VII and X. Panel 10B: Quantification of Islet-GFP signal intensity in the different cranial nerves/loci. 24S,25-Epoxycholesterol (24S,25-EC) was used as a positive control. Data are means±SE (n=4), *, p<0.05; compared to each respective cMO group.

Figure 11:
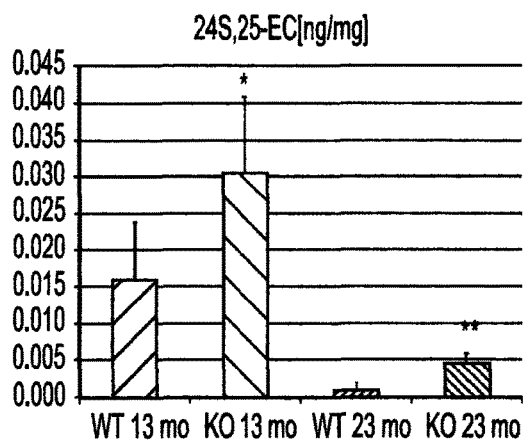
Figure 11:
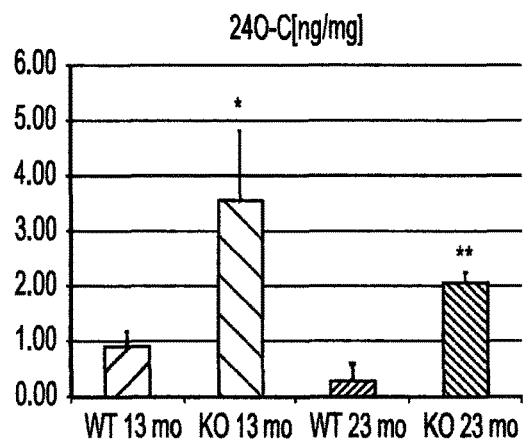
Figure 11:
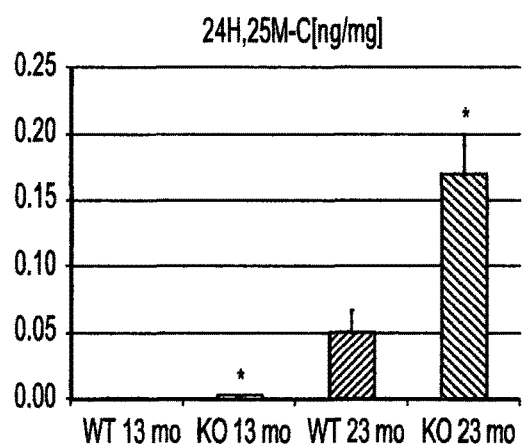
Figure 11:
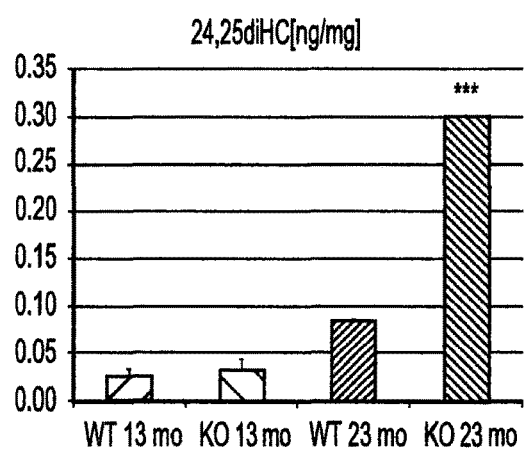
Figure 11:
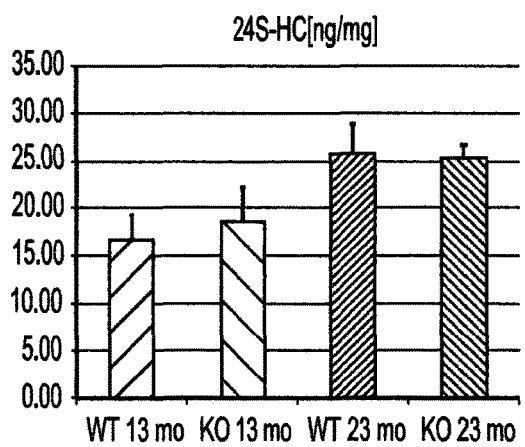
Figure 11:
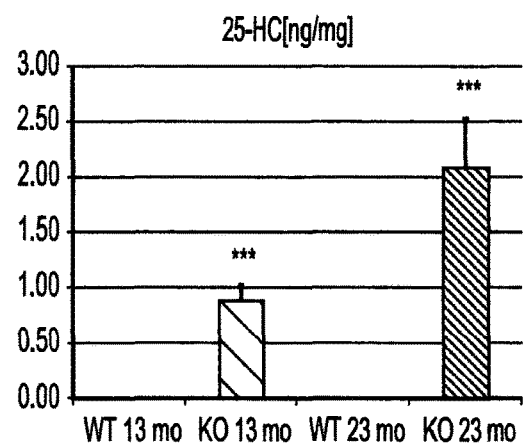
Figure 11:
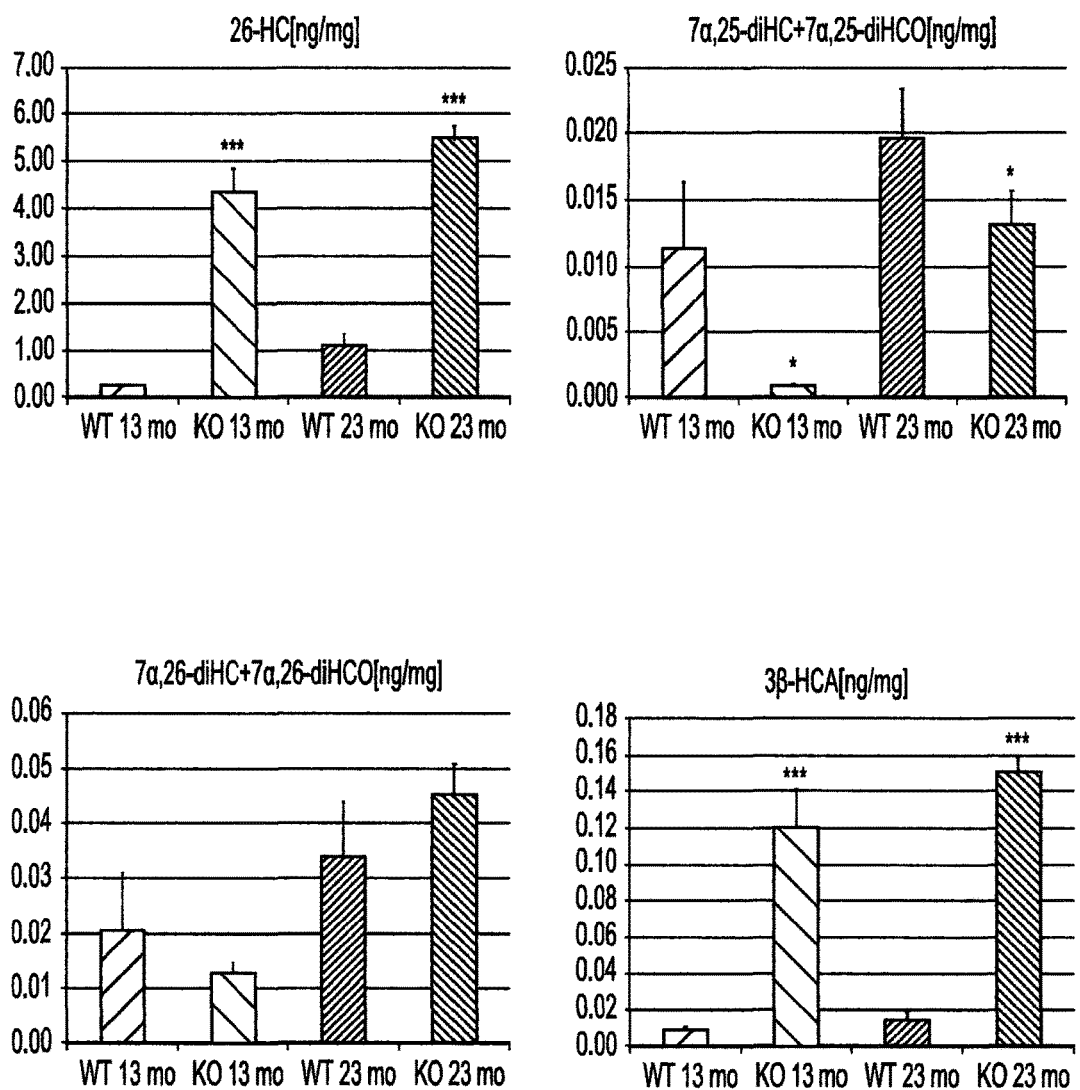

FIG. 11 shows: quantitative analysis of oxysterols and cholestenoic acids in male Cyp7b1−/− mouse plasma and brain. Major cholesterol metabolites identified in mouse plasma (WT 13 mo and KO 13 mo, n=5; WT 23 mo and KO 23 mo, n=4), and brain (WT 13 mo and KO 13 mo, n=3; WT 23 mo and KO 23 mo, n=4) by LC-ESI-MS" following SPE and charge-tagging with GP-hydrazine. Samples were from wild type (WT) and Cyp7b1−/− (KO) animals at 13 and 23 months (mo). Data are means±SD, *, p<0.05; , p<0.01; *, p<0.001 compared to WT. 24S,25-Epoxycholesterol (24S,25-EC) isomerizes to 24-oxocholesterol (24O-C), undergoes hydrolysis to 24,25-dihydroxycholesterol (cholest-5-ene-3β,24,25-triol, 24,25-diHC) and methanolysis to 24-hydroxy-25-methoxycholesterol (3β,24-dihydroxycholest-5-ene-25-methoxide, 24H,25M-C) during derivatisation. Quantification was by stable isotope dilution mass spectrometry using deuterated 24(R/S)-hydroxycholesterol as the internal standard.

Figure 12:
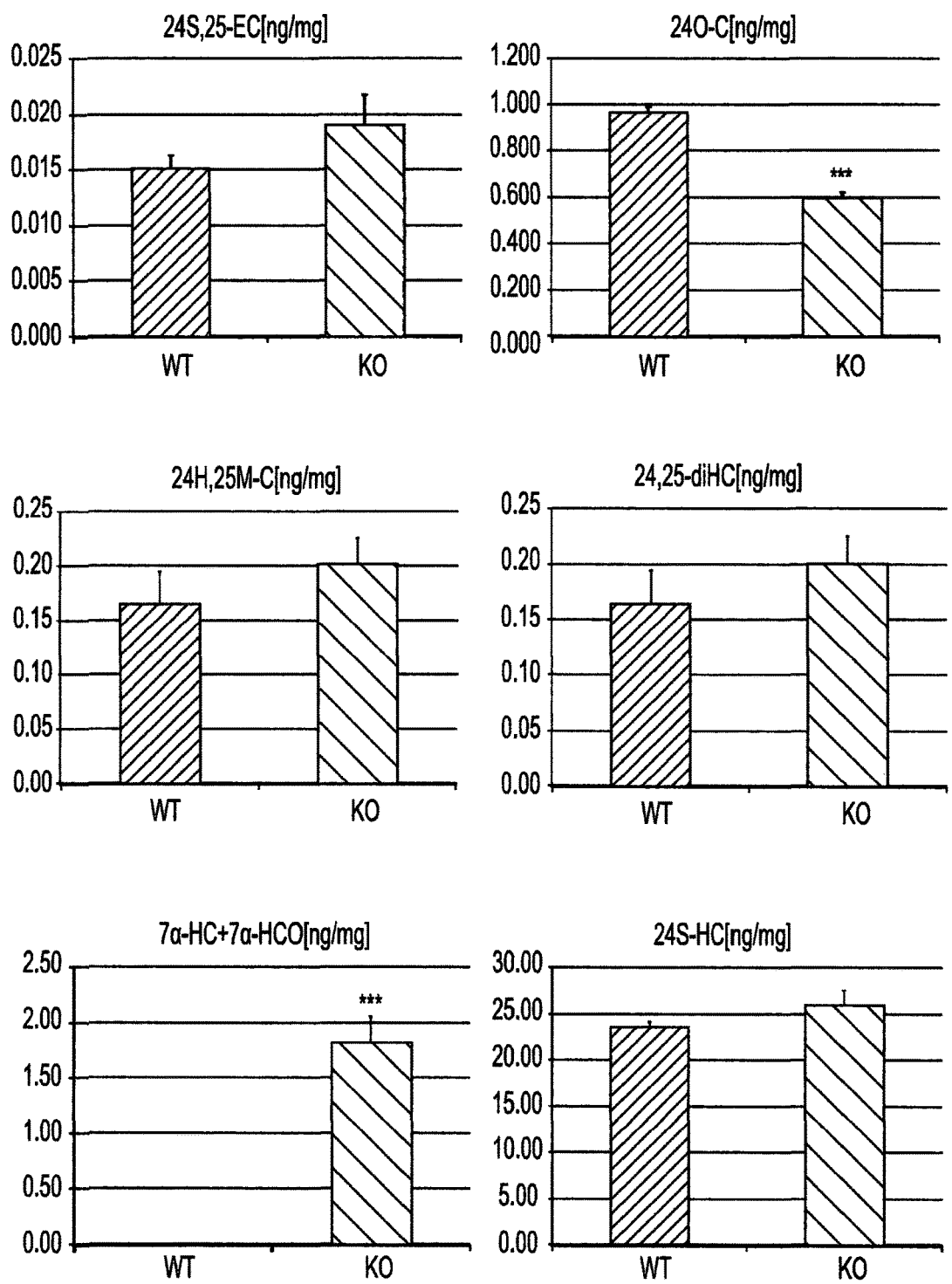
Figure 12:
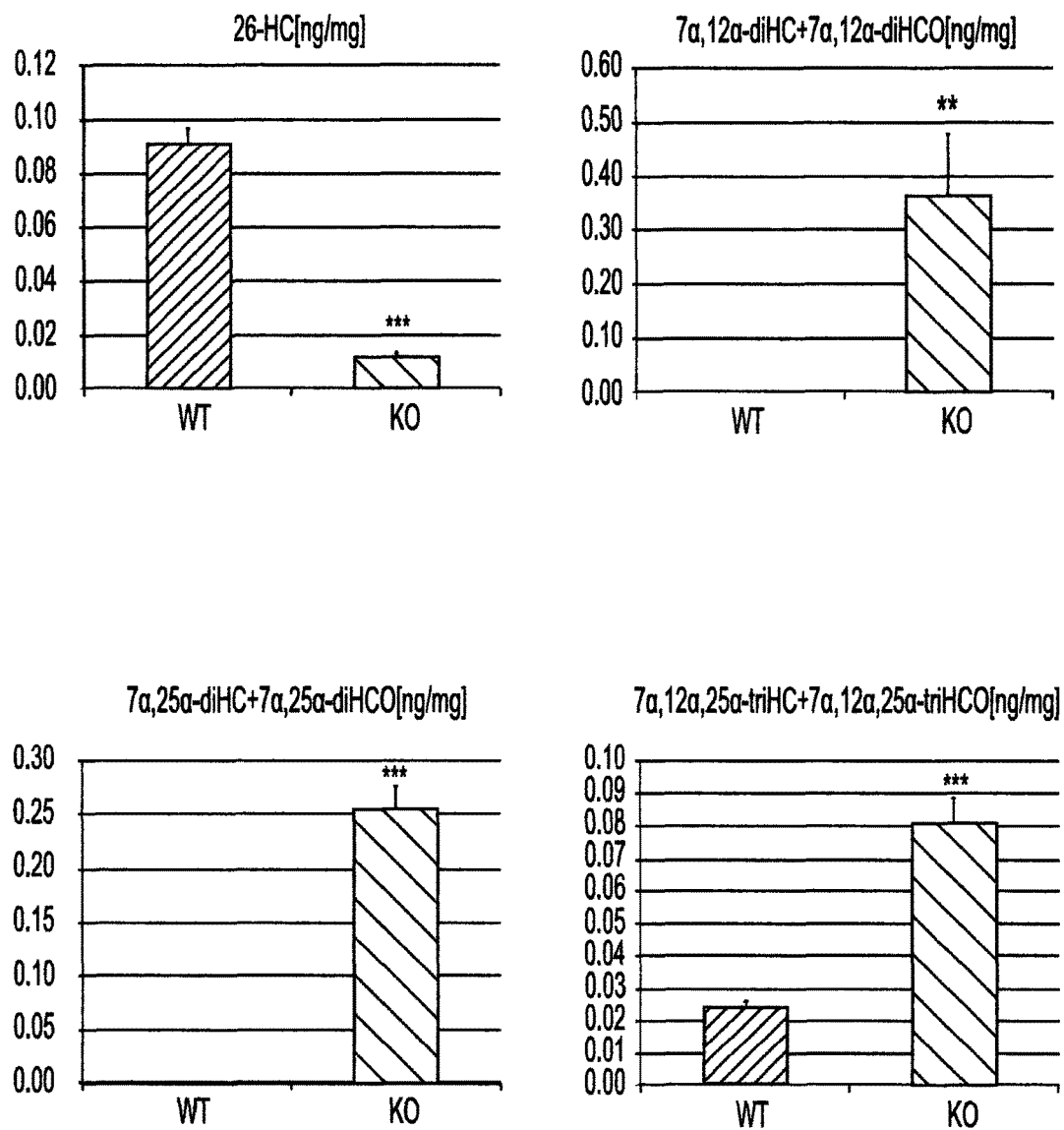

FIG. 12 shows: quantitative analysis of oxysterols and cholestenoic acids in male Cyp27a1−/− mouse brain. Major cholesterol metabolites identified in mouse brain (n=3) by LC-ESI-MS" following SPE and charge-tagging with GP-hydrazine. Samples were from wild type (WT) and Cyp27a1−/− (KO) animals at 3 months. Data are means± SD, *, p<0.05; , p<0.01; *, p<0.001 compared to WT In the absence of authentic standards cholest-5-ene-3β,7α,12α,25-tetrol (7α,12α,25-triHC) and 7α,12α,25-trihydroxycholest-4-en-3-one (7α,12α,25-triHCO) were presumptively identified by exact mass, retention time and MS³ spectra. Quantification was by stable isotope dilution mass spectrometry using deuterated 24(R/S)-hydroxycholesterol as the internal standard.

Figure 13:
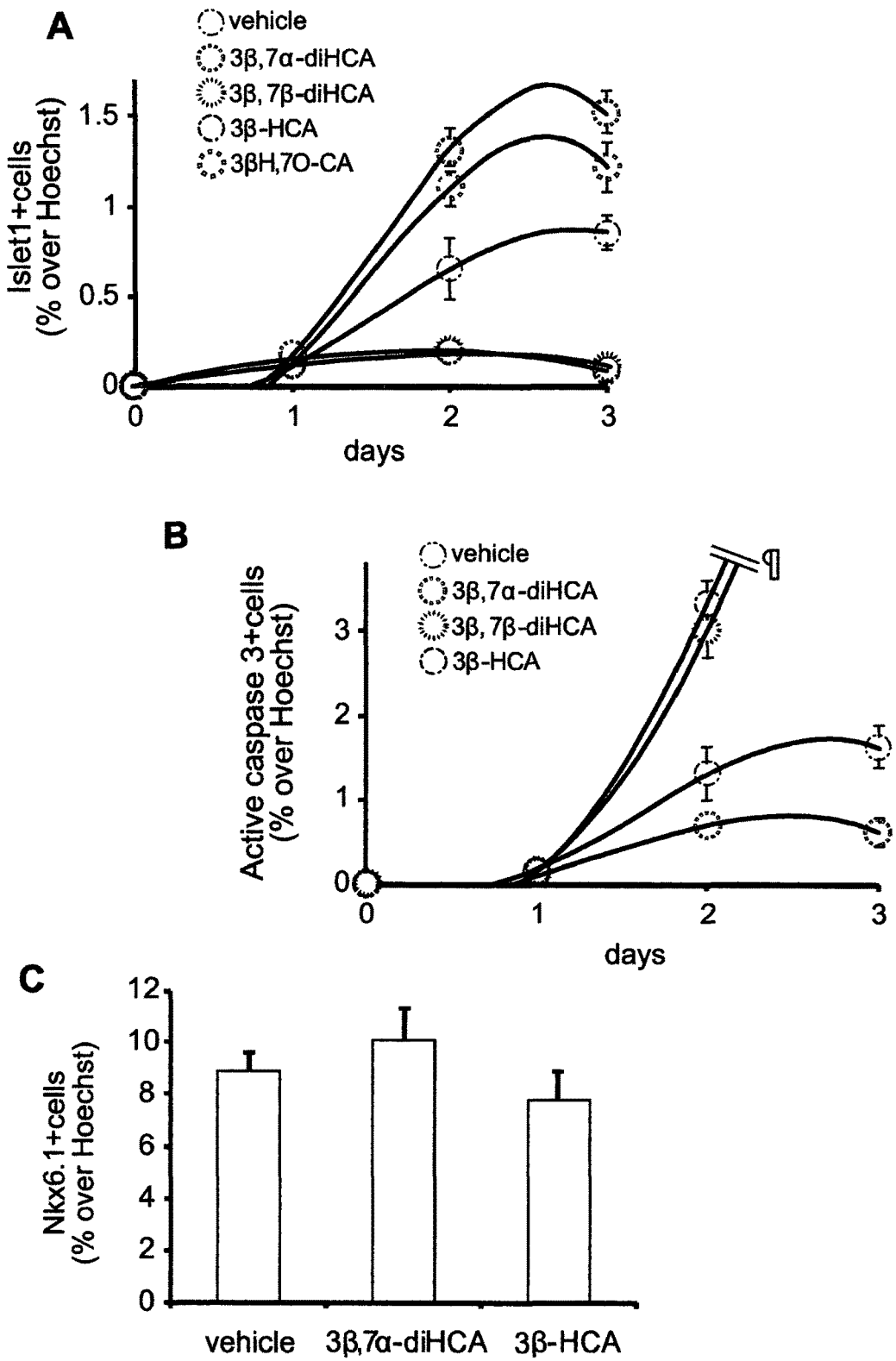

FIG. 13 illustrates a time course analysis and quantification of the number of Islet1+, active caspase 3+ and Nkx6.1+ cells in mouse E11.5 brain primary cultures. Time course analysis for the quantification of (panel A) Islet1+ cells and (panel B) active caspase 3+ cells in mouse E11.5 brain primary cultures treated with 3β,7α-dihydroxycholest-5-en-26-oic (3β,7α-diHCA), 3β,7β-dihydroxycholest-5-en-26-oic (3β,7β-diHCA), 3β-hydroxycholest-5-en-26-oic (3β-HCA) or 3β-hydroxy-7-oxocholest-5-en-26-oic (3βH,7O-CA) acids. The symbol ¶ indicates very high cell death in the cultures. Data are means±SEM (n=3). Panel C: Quantification of Nkx6.1+ progenitor cells in the cultures.

Figure 14:
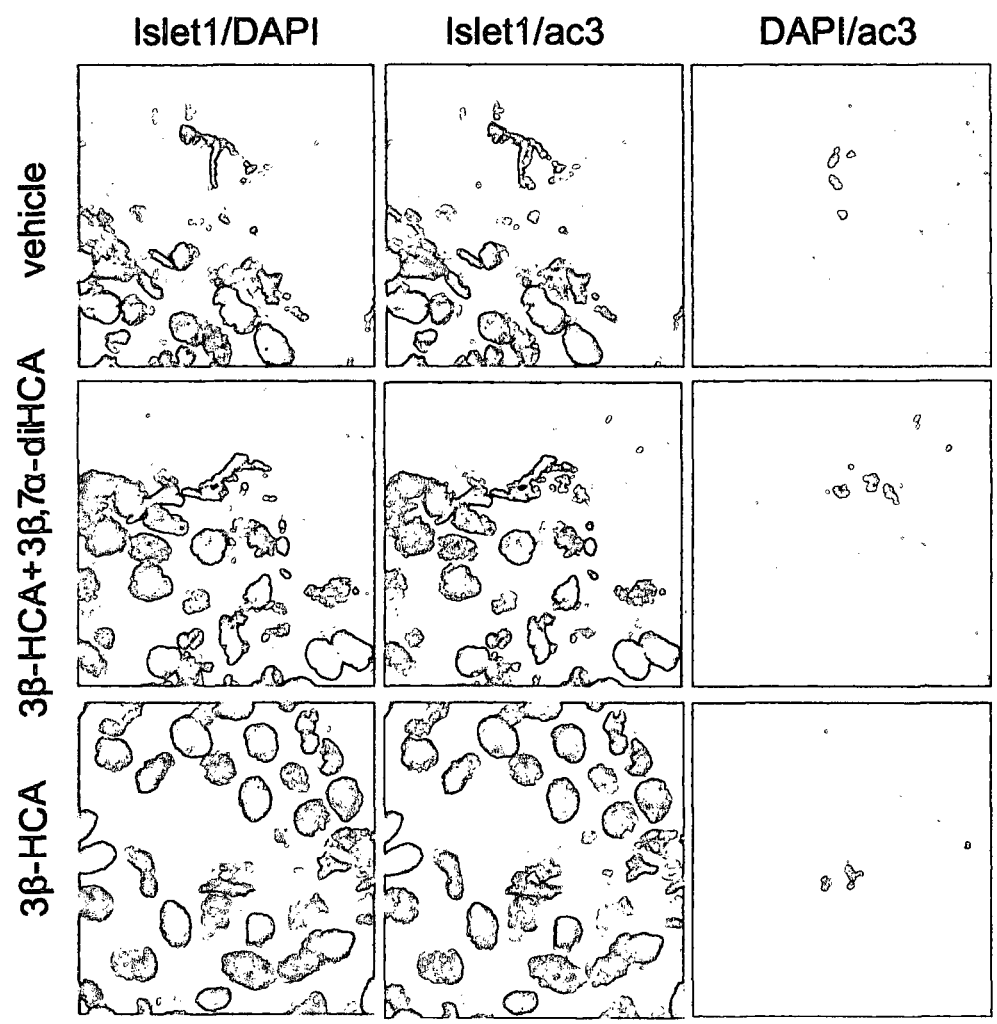

FIG. 14 illustrates the morphological appearance of cells identified as double-positive Islet1+; ac3+ cells in vivo. The cholestenoic acids 3β,7α-dihydroxycholest-5-en-26-oic (3β,7α-diHCA) and 3β-hydroxycholest-5-en-26-oic (3β-HCA), or 3β-HCA were injected into the cerebral aqueduct of E11.5 mice in utero and coronal brain sections were analyzed at E13.5 for double-positive Islet1+; ac3+ cells. A very limited number of oculomotor neurons was undergoing apoptosis in vivo. Representative images of Islet1+/DAPI, Islet1+/ac3+, and DAPI/ac3+ stained cells are shown.

Table 1 shows: oxysterols and Cholestenoic Acids in Human CSF Oxysterols and cholestenoic acids identified by LC-ESI-MS" in CSF following SPE and charge-tagging with GP-hydrazine. In the absence of authentic standards presumptive identifications based on exact mass, MS" spectra and retention time are given. Samples from 12 individual subjects (blue †) and a pool of fifteen subjects (black ‡) were analysed.

Table 2 shows oxysterols and Cholestenoic Acids in Human Plasma (Serum) Oxysterols and cholestenoic acids identified by LC-ESI-MS" in plasma (serum) following SPE and charge-tagging with GP-hydrazine. In the absence of authentic standards presumptive identifications based on exact mass, MS" spectra and retention time are given. Control samples from 56 adults (blue †) and 3 children (black ‡) were analysed. Data for six adults showing clinically pure HSP SPG5 plus one adult with complicated HSP SPG5 (purple*), three infants suffering from O7AHD (gold §), and four patients suffering from CTX (brown ¶) are given. Clinical data is given in Table3.

Table 3 shows: mutations in SPG5, O7AHD and CTX patients studied.

Table 4 shows cholestenoic Acids in Cyp7b1−/− and Cyp27a1−/− Mouse Brain and Plasma Cholestenoic acids identified by LC-ESI-MS" following SPE and charge-tagging with GP-hydrazine.

EXAMPLES

Materials and Methods

Reagents. HPLC grade water and solvents were from Fisher Scientific (UK) or Sigma Aldrich (UK). Authentic sterols, steroids, cholestenoic acids, bile acids and their precursors were from Avanti Polar Lipids (Alabama, USA), Steraloids Inc (Rhode Island, USA), Sigma Aldrich (UK), or from previous studies in our laboratories. Girard P (GP) reagent [1-(carboxymethyl)pyridinium chloride hydrazide] was from TCI Europe (UK) or synthesized in earlier studies, and cholesterol oxidase from *Streptomyces* sp was from Sigma-Aldrich. Certified Sep-Pak $C_{18}$ 200 mg solid phase extraction (SPE) cartridges were from Waters (UK). Leurlock syringes were from BD Biosiences (UK).

Patient Samples. Adult CSF and plasma samples were part of a GlaxoSmithKline study. Plasma/serum from CTX, SPG5 and O7AHD patients were from Barts and the London NHS Trust; St Mary's Hospital, Manchester; Institute of Child Health, London; Conegliano Research Center, Conegliano; University degli Studi di Napoli Federico II, Naples; and Kurume University School of Medicine, Kurume, Japan.

Animals. Lxrα−/−β−/− mouse cell cultures were from the colony at the Department of Biosciences and Nutrition at Novum, Karolinska Institutet. Male and female wild-type and Lxrα−/−β−/− mice were generated as previously described (Alberti et al. J. Clin. Invest 2001:107(5), 565-73). Mice were back crossed onto a C57BL/6 background for 10 generations. Male Cyp7b1−/− mouse brain and plasma were from animals generated at the University of Edinburgh. Male mice homozygous for targeted disruption of the Cyp7b1 gene congenic on the C57BL/6 genetic background (>15 generations backcrossed to C57BL/6) and wild-type littermate controls were generated from Cyp7b1−/+ crosses. Male Cyp27a1−/− mouse tissue and plasma was purchased from The Jackson Laboratory (ME, USA) strain B6.129-Cyp27a1$^{tm1Elt}$/J. The Cyp27a1−/− colony was backcrossed to C57BL/6J inbred mice for approximately 12 generations by the donating investigator prior to sending to The Jackson Laboratory Repository. Upon arrival, mice were bred to C57BL/6J inbred mice for at least one generation to establish the colony. Wild type animals from the colony were used as controls.

Extraction of Sterols. Sterols were extracted from CSF, plasma or mouse brain into ethanol and fractionated by reversed phase SPE to give a cholestenoic acid and oxysterol rich fraction devoid of cholesterol.

Charge Tagging of Sterols. The sterols were charge-tagged with the GP-hydrazine to enhance their response when analysed by LC-ESI-MS and tandem mass spectrometry ($MS^n$).

LC-ESI-MS on the LTQ-Orbitrap LC-ESI-MS and LC-ESI-$MS^n$ was performed using an Ultimate 3000 HPLC system (Dionex, Surrey, UK) linked to the ESI source of a LTQ-Orbitrap XL or LTQ-Orbitrap Velos (Thermo Fisher, San Jose, Calif.) mass spectrometer.

Luciferase Reporter Assay. The ability of oxysterols and their acidic metabolites to activate several nuclear receptors i.e. Lxrα and β, Fxr, Vdr, Nurr1 was tested in luciferase assays. Transient transfection studies were performed in the mouse neuronal cell line SN4741. This cell line was selected as the oxysterols and acidic metabolites tested were initially identified in CSF. Cells were plated in 24-well plates ($5\times10^5$ cells/well) 24 hr before transfection and transfected with 1 µg of plasmid DNA/well complexed with 2 µL of Lipofectamine 2000 (Invitrogen). Cells were transfected with 400 ng of a Lxr-, Fxr-, Vdr- or Nurr1-responsive luciferase reporter construct, and 200 ng of Lxrα, Lx43, Fxr, Vdr or Nurr1. A reporter gene expressing the *Renilla luciferase* (pRL-TK, Promega) was co-transfected in all experiments as an internal control for normalization of transfection efficiency. After a 12 h incubation, the lipid/DNA mix was replaced with fresh 2.5% serum medium containing vehicle or appropriate ligand (10 µM), as specified in each experiment. The ability of cholestenoic acids to activate Lxr was confirmed in experiments with or without the Lxr inhibitor GGPP (10 µM) also added to the medium. Luciferase activities were assayed 24 h later using the Dual-Luciferase Reporter Assay System (Promega), following the manufacturer's protocol.

Lxrβ Ligand Binding Assay. For Lxrβ ligand binding activity measurement, the applicants used the Lanthascreen™ TR-FRET Lxrβ Coactivator Assay (Invitrogen). The assay uses a terbium (Tb)-labeled anti-GST antibody, a fluorescein-labeled coactivator peptide and the Lxrβ-LBD tagged with glutathione-S-transferase (GST). Binding of the agonist/ligand to Lxrβ-LBD causes a conformational change that result in an increase in the affinity of the Lxrβ for the coactivator peptide. The close proximity of the fluorescently labeled coactivator peptide to the Tb-labeled antibody causes an increase in the TR-FRET signal intensity. The TR-FRET ratio of 520/495 was calculated using a Victor multi label reader with an excitation wavelength of 340 nm and emission wavelengths of 520 nm and 495 nm. The activational capacity of potential ligands was tested in a 382-well polypropylene plate, following the manufacturer's protocol.

Quantitative PCR. Total RNA was extracted from SN4741 cells and zebrafish treated with the compounds of interest using the RNeasy Mini Kit (Qiagen), 1 µg was treated with RQ1 RNase-free DNase (Promega) and reverse transcribed using SuperScript II Reverse Transcriptase (Invitrogen) and random primers (Invitrogen) (RT+ reaction). Parallel reactions without reverse transcriptase enzyme were done as a control (RT− reaction), and Sybergreen real-time quantitative PCR assays were performed. Expression levels were obtained by normalization with the value of the housekeeping gene encoding actin obtained for every sample in parallel assays.

Primary Brain Cultures. Brains from E11.5 mice were manually dissected, plated on poly-D-lysine (150,000 cells/$cm^2$) and grown in serum-free N2 media consisting of 1:1 mixture of F12 and DMEM with 10 ng/mL insulin, 100 µg/mL apo-transferrin, 100 µM putrescine, 20 nM progesterone, 30 nM selenium, 6 mg/mL glucose, and 1 mg/mL BSA. Cells were treated for 3 days in vitro (DIV) with the compounds of interest, fixed with 4% PFA and processed for staining using appropriate antibodies.

For BrdU analysis, cells were treated with BrdU one hour after plating and media was replaced with fresh medium after 16 h. After a further 2 days in culture, cells were treated for 30 min with 2N HCl and then immunocytochemistry was performed to evaluate the number of double BrdU+; Islet1+ cells (a measure of motor neuron neurogenesis). Hoechst staining was performed by permeabilizing cells with a 0.3% Triton-X 100/PBS solution for 5 min followed by incubation with Hoechst 33258 (Sigma) for 10 min.

Antibodies and Detection Procedures. Cells were fixed in 4% PFA, washed in PBS and blocked in 5% normal goat serum/PBS for 1 h at room temperature. Primary antibodies were diluted in PBS (pH 7.4), 0.3% Triton X-100, 1% BSA and incubations were carried out overnight at +4° C. or at room temperature for 2 h. The antibodies used were anti-: BrdU (1:400; Abcam), Islet-1 (1:100; Developmental Studies Hybridoma Bank), cleaved caspase-3 (Asp175) (1:100; Cell Signaling Technology), tyrosine hydroxylase (TH; 1:1000; Pel-Freeze) GABA (1:1,000; Sigma), Brn3a (1:250; Millipore), Nkx6.1 (1:200; Novus Biologicals), choline acetyltransferase (ChAT; 1:500; Millipore) and appropriate secondary antibodies (Jackson ImmunoResearch or Alexa). Cells positive for the corresponding marker were counted directly at the microscope at a magnification of 20×. Cells were counted in every well, in eight consecutive fields (going from one side of the well to the other, passing through the center), in three different wells per experiment and in three different experiments per condition. Random pictures of the wells were taken for every condition to document the result, and representative pictures were subsequently selected to represent the quantitative data. Photos were acquired with a Zeiss Axioplan microscope and a Hamamatsu camera C4742-95 using the Openlab software.

Animals for in-Utero Injections and Tissue Preparation. Female wild-type CD-1 mice (25-35 g; Charles River Breeding Laboratories) were housed, bred, and treated according to the guidelines of the European Communities Council (directive 86/609/EEC) and the Society for Neuroscience (www.sfr.org/handbook), and all experiments were approved by the local ethical committee. Ethical approval for CD-1 mice experimentation was granted by Stockholm Norra Djurförsöksetisks Namnd number N154/06, N273/11 and N370/09. For embryo analyses, wild type CD-1 mice were mated overnight, and noon of the day the plug was considered E0.5. Embryos were dissected out of the uterine horns in ice-cold PBS, fixed in 4% paraformaldehyde (PFA) for 4 h to overnight, cryoprotected in 15-30% sucrose, frozen in Tissue-Tek Optimum Cutting Temperature (OCT) compound (Sakura Fine-Tek) on dry ice, and stored at $-80°$ C. until use. Serial coronal 14-µm sections of the brain were obtained on a cryostat.

Immunohistochemical Analysis of Sections. Ten sets of 14 µm serial coronal sections were cut on a cryostat. No. 1 and 6 sets were subjected to immunohistochemistry. Sections were pre-incubated for 1 h in blocking solution followed by incubation at 4° C. overnight with following primary antibodies: anti-TH (1:750, Pel-Freeze), anti-Islet-1 (1:100; Developmental Studies Hybridoma Bank), anti-cleaved caspase-3 (Asp175) (1:100; Cell Signaling Technology). After washing, slides were incubated for 1-2 h at room temperature with the appropriate fluorophore-conjugated (Cy2-, Cy3- and Cy5-, 1:300, Jackson Laboratories; Alexa488-, 555-, and 647-, 1:1000, Invitrogen) secondary antibodies. Confocal pictures were taken with a Zeiss LSMS Exciter or LSM700 microscope.

In Utero Intraventricular Injections. E11.5 pregnant females were deeply anesthetized using Isofluorane (Iso-Flo®, Abbott Labs) and the uterine horns were accessed through an abdominal incision. 1 µL of the different cholestenoic acids studied (5 mM) or vehicle solution (isopropanol, 50% v/v) was injected into the cerebral aqueduct. The uterine horns were replaced into the abdominal cavity, which was then closed with sutures. Embryos were analyzed 48 h later.

Zebrafish Strain and Mainrenance Zebrafish were raised on a 14/10 h day/night cycle and were kept at 28.5° C. Islet-1:GFP transgenic embryos were obtained via natural spawning and staged in hours or days post fertilization (hpf and dpf) according to Kimmel et al). Embryos older than 24 hpf were treated with 0.03% phenylthiourea (PTU) to inhibit pigmentation. MO injections were performed using splice site specific zebrafish lxr MO. MO injected embryos were immediately dechorionated and transferred to a 96 well plate and exposed to dimethyl sulfoxide (DMSO) treated or ligand treated medium.

Compound Exposure. Islet-1:GFP embryos were collected by natural mating and immediately (at 1 cell stage) dechorionated and transferred to a 96 well plate. Each of the compounds tested were obtained as 10 mM stock and diluted in embryo medium to a final concentration of 10 µM, and 200 µL was added to each well. DMSO or propan-2-ol treated embryo medium was taken as control. Ligand solutions were replaced every 12 h with fresh ligand solution prepared in PTU treated embryo medium. Embryos were collected at 48 hpf, fixed for 4 h at room temperature with 4% paraformaldehyde and then washed and kept in PBST Immunocytochemistry was performed using an anti-GFP antibody and fluorescence was viewed and photographed using a Zeiss Axioplan compound microscope and a Zeiss Axiocam digital camera.

Statistical Analysis

Statistical analysis was performed by Student's t-test and Mann-Whitney test using Prism4 (Graphpad Software, La Jolla, Calif.; http://www.graphpad.com). $p<0.05$ was considered a statistically significant difference (*), $p<0.01$ (**). Data represent mean±SE.

A Detailed Description Of An Embodiment Of The Invention

Figure 1:
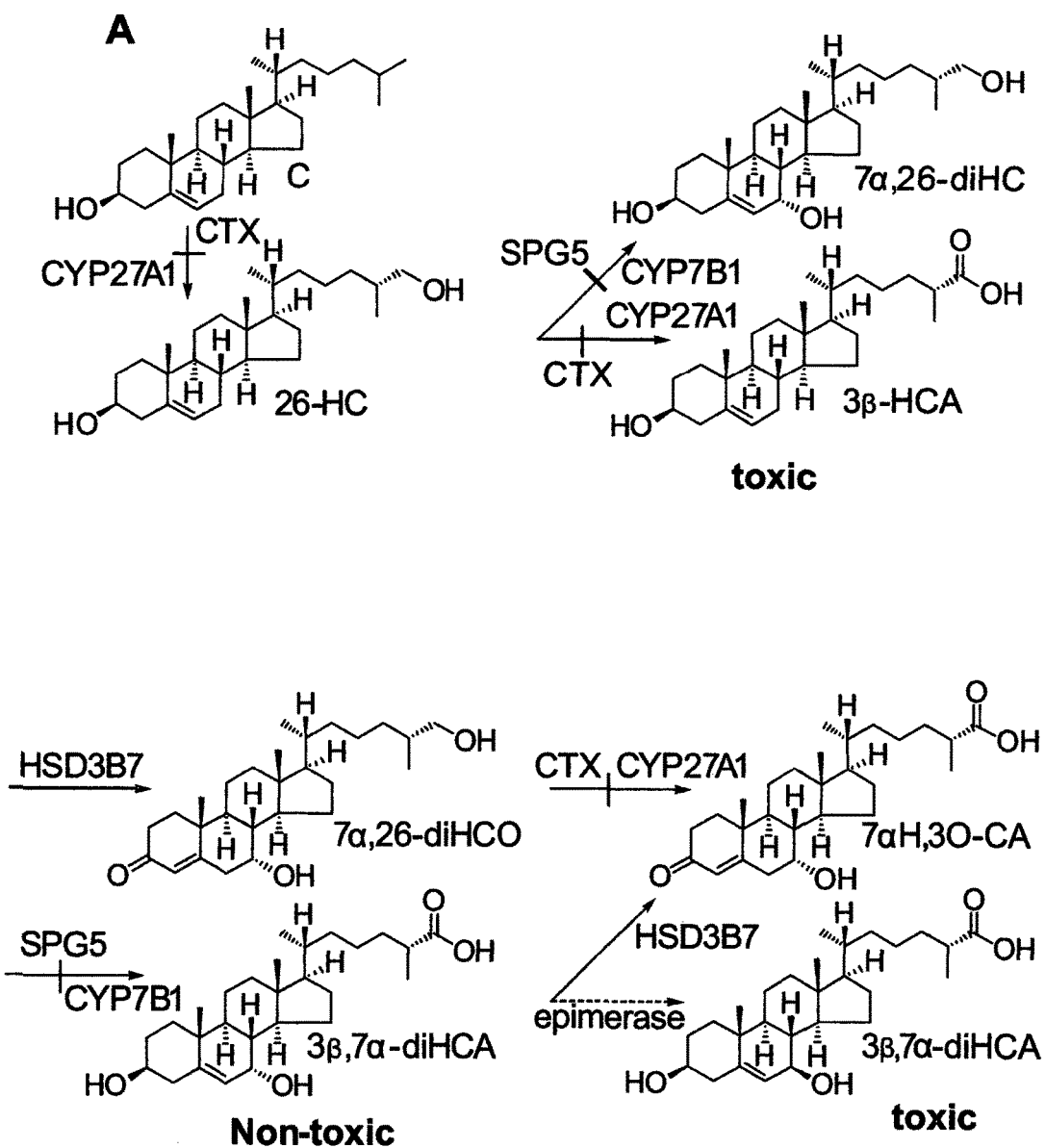
FIG. 1: shows a schematic of the biosynthesis of cholestenoic acids in brain and levels of cholestenoic acids in the circulation. Panel A shows the suggested metabolic pathway for the biosynthesis of 3β-hydroxycholest-5-en-26-oic (3β-HCA), 3β,7α-dihydroxycholest-5-en-26-oic (3β,7α-diHCA), 3β,7β-dihydroxycholest-5-en-26-oic (3β,7β-diHCA) and 7α-hydroxy-3-oxocholest-4-en-26-oic (7αH,3O-CA) acids. The pathway may start with cholesterol (C) which is synthesised in brain or 26-hydroxycholesterol (26-HC) which may be formed from cholesterol in brain or imported from the circulation. With the exception of the epimerase, each enzyme is known to be expressed in the brain. Enzyme defects in CTX and SPG5 are depicted by solid bars across arrows. Metabolites toxic towards neurons are shown in as having the exact mass 416.3290 (3β-HCA) and 432.3240 (3β,7β-diHCA) and that which is neuroprotective in shown with mass 432.3240 (3β,7α-diHCA). Panel B shows the levels of 26-HC (ng/mL, mean±SE) in plasma/serum from healthy adults (n=56), children (n=3), adult SPG5 patients (n=9), infants suffering from O7AHD (n=3) and CTX patients (n=4, indicated by an arrow). Panel C shows the levels of 3β-HCA in plasma/serum from the indicated subjects. Panel D shows the levels of 3β,7α-diHCA in plasma/serum from the indicted subjects. Panel E shows the levels of 3β,7β-diHCA in plasma/serum from the indicated subjects. Measurements were made by LC-ESI-MS (see Table 2 below). For sterols the applicants use the abbreviation C for the cholesterol, CO for the cholest-4-en-3-one and CA for the cholesten-26-oic acid structures; while numbers (with Greek letters) indicate the location of hydroxy (H) and oxo (O) groups. In this work the applicants have adopted the sterol nomenclature recommended by the lipid maps consortium, where 26-HC refers to cholest-(25R)-5-en-3β,26-diol.
Figure 1:
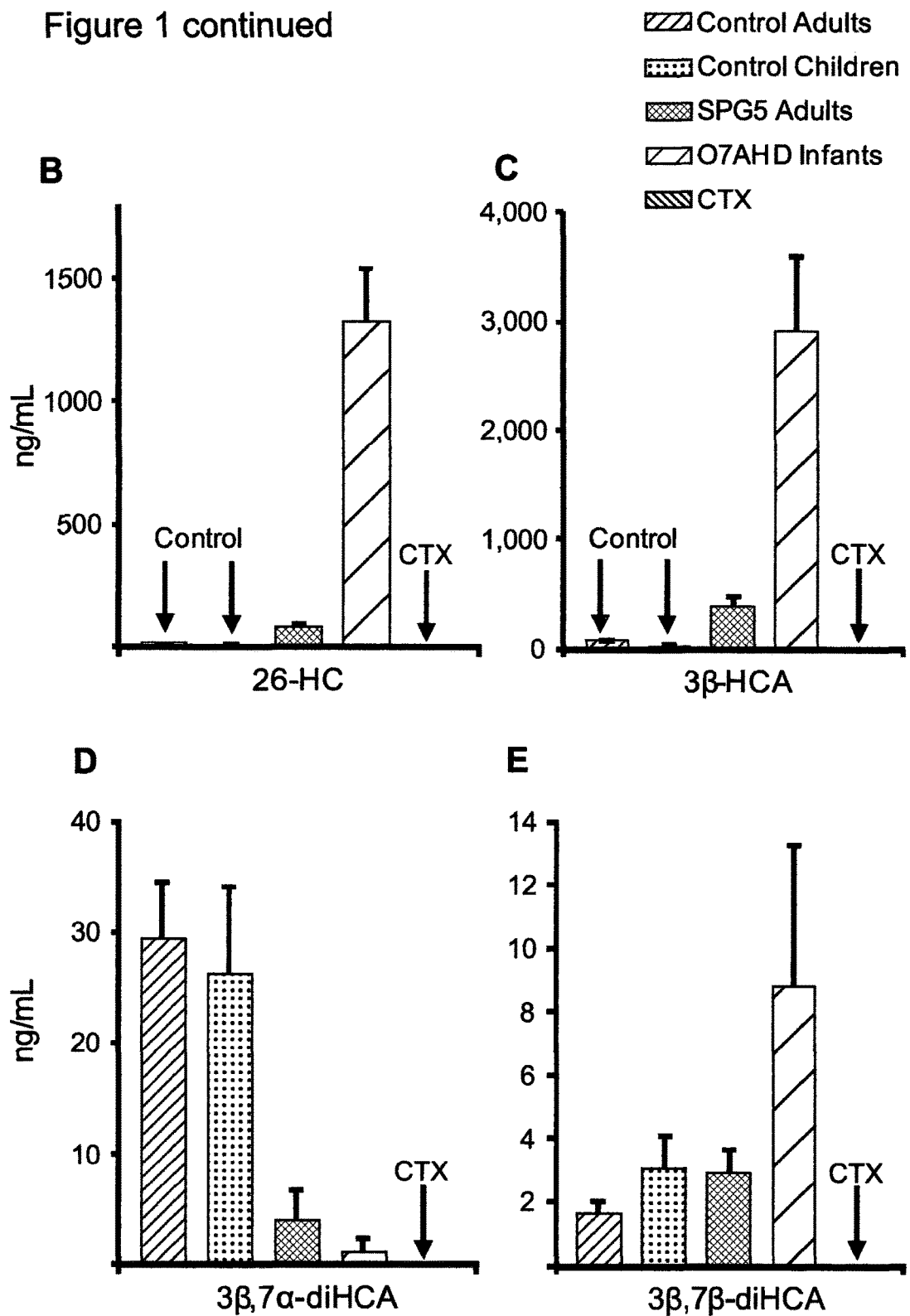

As discussed previously, cholesterol metabolites have the capacity to activate Lxrs but the applicants set out to to identify what these metabolites are and how they act in plasma and cerebrospinal fluid (CSF) of patients with human diseases associated with motor dysfunction, cerebrotendinous xanthomatosis (CTX) and hereditary spastic paresis (HSP) type 5 (SPG5) and patients with oxysterol 7α-hydoxylase deficiency (O7AHD). These diseases result from mutations in the cytochrome P450 (CYP27A1, CYP7B1 and CYP7B1) genes, respectively. The enzymes coded by these genes are responsible for (25R),26-hydroxylation of cholesterol and 7α-hydroxylation of oxysterols, respectively, reactions that generate further oxysterols and ultimately cholestenoic acids (FIG. 1). It has been found that specific cholestenoic acids with a 3β-hydroxy-5-ene, but not a 3-oxo-4-ene, structure activate Lxrα and Lxrβ in neuronal cells, increase expression of Islet-1, a transcription factor required for the development of motor neurons, and promote the survival of Islet1+ oculomotor neurons. Moreover these effects were abolished by knock-down or knock-out of the Lxr receptors in zebrafish or in rodent models. In addition, patients with CTX and SPG5, diseases characterized by ataxia, pyramidal signs, motor dysfunction and spastic paraplegia, are unable to synthesize normal amounts of the Lxr ligand 3β,7α-dihydroxycholest-5-en-26-oic acid (3β, 7α-diHCA), a cholestenoic acid that the applicants found promotes neuronal survival. Additionally, SPG5 patients exhibit a build-up of 3β-hydroxycholest-5-en-26-oic acid (3β-HCA), an Lxr ligand that is toxic to mouse motor neurons in vitro and to zebrafish in vivo. These results indicate that specific Lxr ligands regulate the balance between motor neuron survival and death. These findings have important implications for neurological diseases leading to motor dysfunction such as CTX and SPG5, since Lxr ligands, as well as inhibitors of specific biosynthetic enzymes in the cholestenoic acid biosynthetic/metabolic pathway, may be useful pharmaceuticals for the treatment of motor neuron disorders.

Cholestenoic acids are abundant in human plasma and human CSF (cerebralspinal fluid) also contains cholestenoic acids. Surprisingly, in CSF the levels of cholestenoic acids were higher than those of oxysterols. The exact identity of 16 oxysterols and down-stream metabolites, including cholestenoic acids in human CSF are shown in Table 1. The most abundant of these metabolites were 7α-hydroxy-3-oxocholest-4-en-26-oic acid (7αH,3O-CA) 3β-hydroxycholest-5-en-26-oic acid (3β-HCA) and newly identified in CSF 3β,7α-diHCA and 3β,7β-dihydroxycholest-5-en-26-oic acid (3β,7β-diHCA) (19.48-0.25 ng/mL, FIG. 7). Precursors of these acids, including 26-hydroxycholesterol (cholest-(25R)-5-ene-3β,26-diol, 26-HC) and newly identified 7α,26-dihydroxycholesterol (cholest-5-ene-3β,7α,26-triol, 7α,26-diHC) and 7α,26-dihydroxycholest-4-en-3-one (7α,26-diHCO), were also found, but at lower levels (0.15-0.02 ng/mL). These results identify four novel oxysterols metabolites in human CSF (FIG. 1) which are downstream of 26-HC. 26-HC is metabolized via 7α,26-diHC and 7α,26-diHCO or via 3β-HCA and 3β,7α-diHCA to 7αH,30-CA. While 26-HC can cross the blood brain barrier (BBB) and enter brain from the circulation, 7αH,3O-CA traverses the BBB and is exported from brain. The applicants went on to measure the level of cholestenoic acids and oxysterols in human plasma to examine the likelihood that cholestenoic acids enter or exit the CSF from or to the circulation (Table 2). The CSF to plasma ratio for 7αH,3O-CA is >1:6 while for 26-HC it is <1:130. These ratios are consistent with the concept that while 26-HC in CSF is likely, at least in-part, to be derived by diffusion from blood, this is much less likely to be the situation for 7αH,3O-CA and other acids where the concentration gradient is far less steep. Very low levels of 24S-hydroxycholesterol (cholest-5-ene-3β,24S-diol, 24S-HC), 25-hydroxycholesterol (cholest-5-ene-3β,25-diol, 25-HC), and newly identified 7α,25-dihydroxycholesterol (cholest-5-ene-3β,7α,25-triol, 7α,25-diHC) and 7a 25-dihydroxycholest-4-en-3-one (7α,25-diHCO) were also found in CSF (0.08 0.01 ng/mL).

Low levels of 26-HC have been found in human and mouse brain and in human CSF conversely, 7αH,3O-CA, a metabolic product of 26-HC, is exported from brain to blood in human. The CSF to plasma ratios for 7αH,3O-CA and 26-HC has been found to be >1:6 and <1:130, respectively. These ratios are consistent with the hypothesis that while 26-HC is imported into the CNS, 7αH,3O-CA, the most abundant sterol metabolite found in CSF, is synthesized in the CNS.

Reduced Levels of 7α-Hydroxylated Cholestenoic Acids in Plasma/Serum of Human Patients with CTX Cerebrotendinous-Xanthomatosis and SPG5 Hereditary Spastic Paraplegia Two human diseases that can present with upper motor neuron signs, CTX and SPG5, result from mutations in CYP27A1 and CYP7B1, respectively, two of the genes encoding enzymes required for extrahepatic synthesis of 7αH,3O-CA and its precursor 3β,7α-diHCA (FIG. 1, panel A). In order to examine the pathogenic role of such mutations the applicants decided to first identify the alterations in oxysterol and cholestenoic acid profiles in plasma from these patients and then examine their biological activities. We found that the plasma of patients with CTX was essentially devoid of 26-HC and the down-stream cholestenoic acids (FIG. 1B-1E, Table 2). There were elevated levels of 7α-hydroxycholesterol (cholest-5-ene-3β,7α-diol, 7α-HC) plus 7α-hydroxycholest-4-en-3-one (7α-HCO) and/or 7α,12α-dihydroxycholesterol (cholest-5-ene-3β,7α,12α-triol, 7α,12α-diHC) plus 7α,12α-dihydroxycholest-4-en-3-one (7α,12α-diHCO) (see Table 2). The absence of cholestenoic acids in plasma indicates an inability to biosynthesize $C_{27}$ acids in extrahepatic steroidogenic tissue of the central nervous system (CNS).

The applicants also examined patients with SPG5, a disease resulting from mutations in the CYP7B1 gene encoding the oxysterol 7α-hydroxylase responsible for the extrahepatic 7α-hydroxylation of side-chain oxidised sterols. In agreement with this, a 6-9 fold increase in 26-HC was been described in plasma of SPG5 patients. Here the applicants studied six patients showing pure SPG5 and one adult showing complex SPG5. In all cases elevated levels of the CYP7B1 substrates 25-HC, 26-HC and 3β-HCA (FIG. 1, panel A), as well as reduced levels of its product 3β,7α-diHCA were found, compared to control subjects (FIG. 1, panels B & C, Table 2). While 3β,7α-diHCA in the CNS is normally derived from 26-HC, that found in the circulation can be derived via either the 26-HC (acidic) or the 7α-HC (neutral) pathway of bile acid biosynthesis. Thus, in SPG5 patients (mutation of CYP7B1) the liver specific 7α-hydroxylase, CYP7A1, (neutral pathway) accounts for the residual content of 3β,7α-diHCA found in the circulation.

The applicants were also able to analyse CSF from three patients with SPG5 and two health carriers, heterozygotes, with a single mutation in CYP7B1 (Table 3). As observed in plasma, levels of 25-HC, 26-HC and 3β-HCA were elevated in the patient CSF while 3β,7α-diHCA was reduced. This indicates that, for these metabolites, plasma represents a good surrogate for CSF.

The applicants also investigated the plasma oxysterol and cholestenoic acid profile of three infants with mutations in CYP7B1 (Table 2) resulting in oxysterol 7α-hydroxylase deficiency (O7AHD) and neonatal liver disease), as well as SPG5 in adults. The first identification of CYP7B1 mutations were found in a child with severe cholestasis, defining an inborn error of bile acid biosynthesis. As expected by the absence of functional CYP7B1 in these patients, the applicants found very low plasma levels of 3β,7α-diHCA and elevated levels of 3β-HCA, as described above for SPG5 (FIG. 1, panels C & D, Table 2). These patients also had considerably elevated plasma levels of 24S-, 25- and 26-HC and high levels of hepatotoxic 3β-hydroxychol-5-en-24-oic acid (3βH-Δ$^5$-BA) compared to SPG5 patients and controls. These findings suggest that additional factors, including increased levels of toxic 3β-hydroxy-5-ene acids, may contribute to the progressive liver disease at an early age in these patients. The research shows specific changes in 7α-hydroxylated cholestenoic acids in plasma/serum of CTX and SPG5 patients so the applicants thus decided to examine their impact on neural function.

Cholestenoic Acids and action as Lxr Ligands

Figure 2:
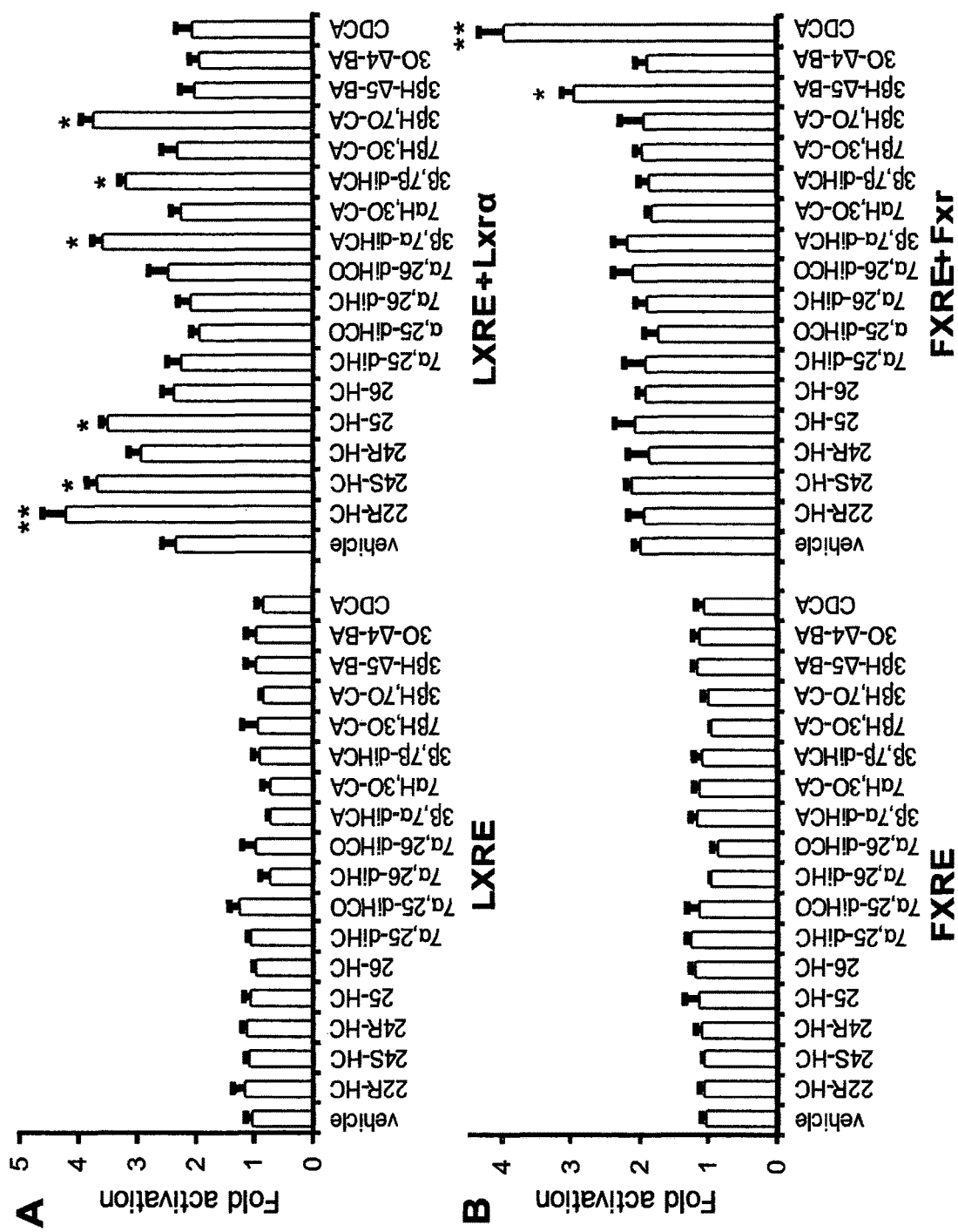
FIG. 2 shows: an analysis of the nuclear receptor activational capacity of oxysterols and cholestenoic acids. Panel A shows an analysis of luciferase activity in SN4741 neural cells transfected with an Lxr-responsive luciferase reporter construct (Lxre) and Lxrα, as indicated, and stimulated for 24 h with 22R-hydroxycholesterol (22R-HC; 10 μm), a known Lxrα ligand, or the compounds indicated. In panel B one sees a similar assay performed with cells transfected with an Fxr-responsive luciferase reporter construct (Fxre) and Fxr and stimulated for 24 h with chenodeoxycholic acid (CDCA), a known Fxr ligand, or the compounds indicated. In panel C additional luciferase assays are performed as in panel A with or without the addition of the Lxr antagonist geranylgeranyl pyrophosphate (GGPP, 10 μM) along with the cholesterol metabolite indicated (10 μM). Other compounds: 24S-hydroxycholesterol (24S-HC); 24R-hydroxycholesterol (24R-HC); 25-hydroxycholesterol (25-HC); 26-hydroxycholesterol (26-HC); 7α,25-dihydroxycholesterol (7α,25-diHC); 7α,25-dihydroxycholest-4-en-3-one (7α,25-diHCO); 7α,26-dihydroxycholesterol (7α,26-diHC); 7α,26-dihydroxycholest-4-en-3-one (7α,26-diHCO); 3β,7α-dihydroxycholest-5-en-26-oic acid (3β,7α-diHCA); 7α-hydroxy-3-oxocholest-4-en-26-oic acid (7αH,3O-CA); 3β,7β-dihydroxycholest-5-en-26-oic acid (3β,7β-diHCA); 7β-hydroxy-3-oxocholest-4-en-26-oic acid (7βH,3O-CA); 3β-hydroxy-7-oxocholest-5-en-26-oic acid (3βH,7β-CA); 3β-hydroxychol-5-en-24-oic acid (3βH-Δ$^5$-BA); and 3-oxo-chol-4-en-24-oic acid (3O-Δ$^4$-BA) may be relevant.
Figure 2:
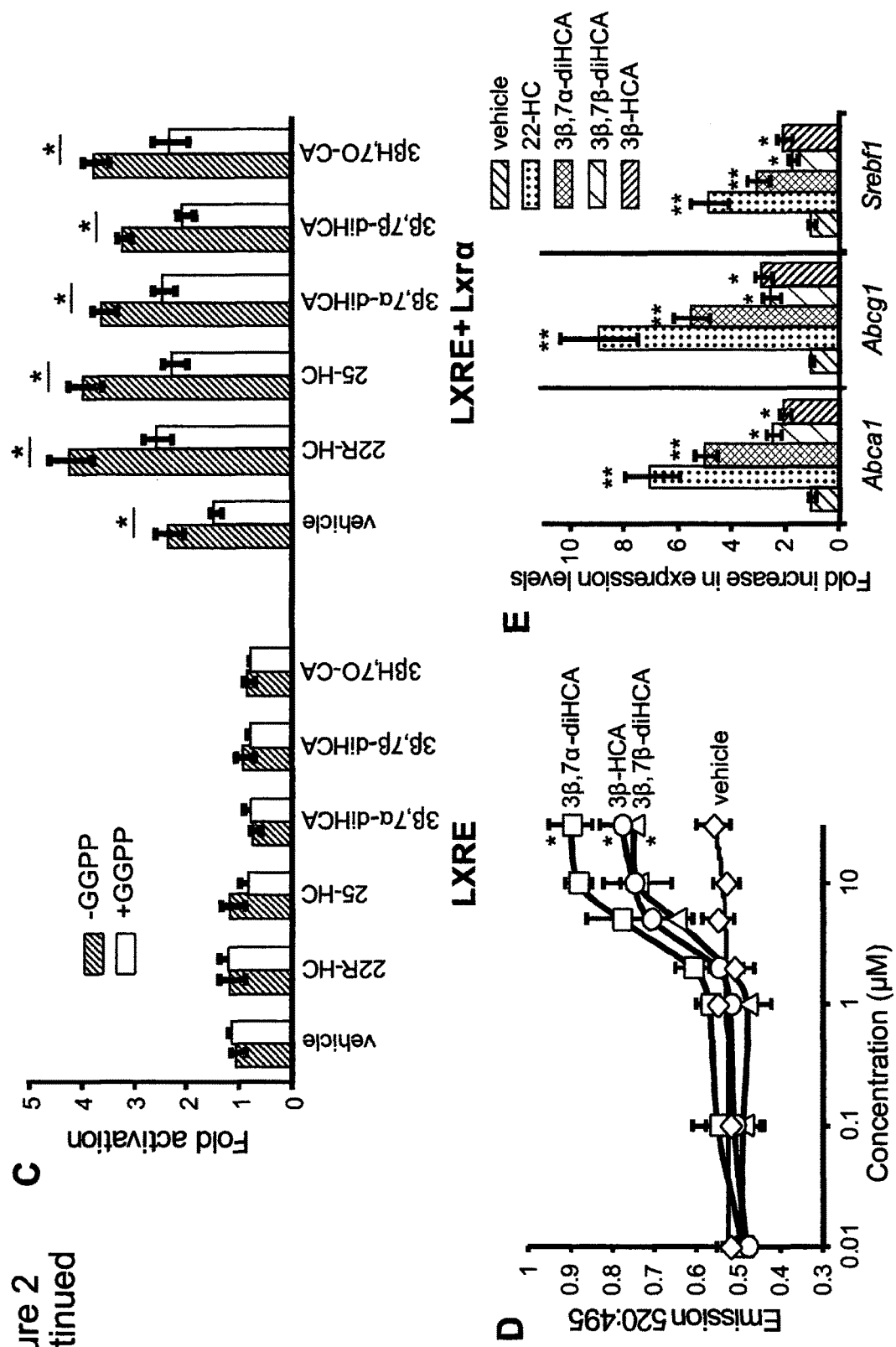

In order to gain insights into the mechanism by which alterations in cholesterol metabolism causes neurological disease, the applicants studied whether any of the cholestenoic acids present at high levels in control human CSF and deregulated in CSF or plasma of SPG5 or CTX patients work as Lxr ligands. The applicants thus focused on 3β-HCA, 3β,7α-diHCA its isomer 3β,7β-diHCA and 7αH,3O-CA (FIG. 1, panel A), and tested their capacity to activate Lxrα and β in a neuronal cell line (SN4741). The applicants previously found that 3β-HCA activates Lxr and the applicants now show that 3β,7α-diHCA, its isomer 3β,7β-diHCA and the necessary intermediate for the interconversion of the isomers, 3β-hydroxy-7-oxocholest-5-en-26-oic acid (3βH,7O-CA), have the ability to activate both Lxrs and therefore act as Lxr ligands in neural cells (FIG. 2, panel A and FIG. 8, panel A). In addition, the applicants confirmed in our system the capacity of 24S-HC and 25-HC to activate Lxr and the applicants observed that 26-HC had no a significant effect. The applicants also tested the activational capacity of 7αH,3O-CA and its 7β-isomer (7β-hydroxy-3-oxocholest-4-en-26-oic acid, 7βH,3O-CA), and the precursors 7α,26-diHC and 7α,26-diHCO, none of which was found to show significant activity (FIG. 2, panel A and FIG. 8, panel A). Moreover, in order to examine if the identified acidic ligands exert their effect by binding to Lxr, the applicants used the Lxr antagonist geranylgeranyl pyrophosphate (GGPP) which blocked their activity, indicating that the acids are indeed Lxr ligands (FIG. 2, panel C). The activity of the known Lxr ligands 22R-hydroxycholesterol (22R-HC) and 25-HC was similarly blocked.

In order to confirm that the cholestenoic acids are indeed agonists to Lxr the applicants tested the Lxrβ activational capacity of either 3β,7α-diHCA, 3β,7β-diHCA or 3β-HCA in combination with 22R-HC. No additive effect was observed, indicating that the acid molecules work via the same mechanism as 22R-HC (FIG. 9, panel A). To further examine the specificity of the cholestenoic acids described above, farnesoid X receptor (Fxr) luciferase reporter assays were performed (FIG. 2, panel B). Chenodeoxycholic acid (3α,7α-dihydroxy-5β-cholan-24-oic acid, CDCA) activated Fxr. Interestingly 3βH-Δ⁵-BA (, a cholesterol metabolite identified in plasma (Table 2) also activated Fxr, but was less potent than CDCA. However, none of the other compounds tested activated the Fxr luciferase reporter in the neural cells (FIG. 2, panel B), or modulated the activity of CDCA in neural cells (FIG. 9, panel B). Thus, the cholestenoic acids do not exert their effect via modulating the activity of the Fxr nuclear receptor or its ligands. Similarly, cholestenoic acids did not activate luciferase reporter assays under the control of a DR5 element (activated by Nur-related factor 1 (Nurr1)/retinoid X receptor (Rxr) heterodimers) while 9-cis-retinoic acid (9-cis-RA) activated this reporter (FIG. 8, panel C). Furthermore, while lithocholic acid (3β-hydroxy-5β-cholan-24-oic acid, LCA) activated a vitamin D receptor (Vdr) luciferase reporter, none of the cholestenoic acids tested showed any significant effect on Vdr activation in neural cells (FIG. 8, panel B). Thus, our results indicate that 3β-HCA, 3β,7α-diHCA, 3β,7β-diHCA, and 3βH,7O-CA are specific Lxr ligands in neural cells.

Cholestenoic Acids Bind and Activate Lxr

In order to show that specific cholestenoic acids directly interact with Lxr the applicants performed a binding and activation fluorescence resonance energy transfer (FRET) assay in which ligand binding to the ligand binding domain (LBD) of Lx43 recruits a fluorescent coactivator. The applicants found that 3β,7α-diHCA induced FRET in a dose dependent manner to a higher degree than the other acids (FIG. 2, panel D). To provide further evidence that cholestenoic acids are Lxr ligands in neural cells, the applicants treated neural cells with the individual acids for 3 h and measured Abca1, Abcg1 and Srebf1 transcript levels. 3β,7α-diHCA increased transcripts levels to a similar degree as 22R-HC, while 3β,7O-diHCA and 3β-HCA induced transcription, but to a lesser extent (FIG. 2, panel E). These results provide further proof that 3β-HCA, 3β,7α-diHCA and 3β,7β-diHCA are specific Lxr ligands in neural cells.

Cholestenoic Acids Increase Expression of Islet-1 Protein in Islet-1 GFP Zebrafish Embryos Having established that cholestenoic acids that are altered in CTX or SPG5 can activate Lxrs in vitro, the applicants next sought to identify their effect in vivo. In particular, the applicants focused on the expression of Islet-1, a transcription factor expressed in all postmitotic motor neurons and required for multiple aspects of motor neuron development, including motor neuron specification, motor column formation, axonal growth and maintenance of spinal motor neuron identity. The applicants used transgenic zebrafish embryos expressing green fluorescent protein (GFP) driven by the Isl1 gene promoter/enhancer sequences (Tg[Isl1:GFP]) to screen for biologically active compounds in vivo. Previous studies have indicated that Islet-1 protein is required for the formation of zebrafish primary motor neurons and is conserved throughout vertebrate evolution. Treatment of transgenic zebrafish embryos with 3β-HCA and 3β,7β-diHCA, two weak Lxr ligands, as well as CDCA, the most potent Fxr ligand, had a deleterious toxic effect which impaired the survival of the fish and precluded further in vivo analysis. The applicants also found that the Lxr agonists 3β,7α-diHCA and 3βH,7O-CA increased Islet-GFP expression (FIG. 3, panels 3A & 3B), but had no significant effect on the number of Islet1+ cells in the different cranial nerves examined (III, IV, V, VII, X). These effects were specific as 7αH,3O-CA, which is not an Lxr ligand, failed to regulate Islet-GFP expression (FIG. 3, panel 3B). Interestingly, the increase in Islet-GFP expression, observed in response to the specific acidic compounds, was evident in all cranial nerves studied (FIG. 3, panel 3B). Moreover the increase in Islet-GFP expression by 3β,7α-diHCA and 3βH,7O-CA was also accompanied by an increase in the level of Islet-1 mRNA and protein, as assessed by qPCR and western blot (FIG. 3, panels 3C-3E). To further verify our results, the applicants examined whether these cholestenoic acids regulated the in vivo expression of endogenous Lxr target genes such as abca1. Our results show enhanced expression of abca1 by both 3β,7α-diHCA and 3βH,7O-CA but not 7αH-3O-CA (FIG. 3, panel 3F). Finally, in order to determine whether these effects are actually mediated by Lxrs the applicants performed lxr morpholino (MO) injections in Islet-GFP transgenic fish. Interestingly, the applicants found that lxr MO injections abolished the in vivo increase in Islet-GFP levels by 3β,7α-diHCA and 3βH,7O-CA, compared to control scrambled MO (FIG. 10). Thus, our data show that cholestenoic acids are capable of activating endogenous Lxr target genes in vivo and regulate the in vivo expression of Islet-1 in brain motor neurons via Lxr.

3β,7α-diHCA Promotes Rodent Motor Neuron Survival In Vitro, while 3β,7β-diHCA and 3β-HCA are Toxic In order to determine the functional relevance of our findings in mammalian cells, it was examined first whether any of the cholestenoic acids present in human CSF and implicated in motor neuron disease were also capable of regulating Islet-1 expression in mouse primary brain progenitor cultures. The applicants first performed dose response analysis of the cholestenoic acids of interest, using a wide range of concentrations; while, 3β,7β-diHCA and 3β-HCA caused the loss of Islet1+ cells in the cultures, 3β,7α-diHCA and 3βH,7O-CA increased the number of Islet1+ oculomotor cells in the cultures (FIG. 4, panels A & 4H). The Islet1+ cells co-expressed the transcription factor Nkx6.1 (FIG. 4, panel B) and choline acetyltransferase (ChAT) (data not shown), therefore were true (bona fide) oculomotor neurons. Time course analysis confirmed the stimulatory effect of 3β,7α-diHCA and 3βH,7O-CA, as well as the toxic effects of 3β,7β-diHCA and 3β-HCA over a range of incubation times (FIG. 13, panel A). Our analysis shows that the peak of motor neuron production occurred after 2 days in culture and leveled thereafter. These results thus confirmed the dual effects of cholestenoic acids in zebrafish, where 3β,7β-diHCA and 3β-HCA caused the death of the fish while 3β,7α-diHCA and 3βH,7O-CA regulated Islet-1 expression, providing further evidence of the differential effect of cholestenoic acids on Islet1+ oculomotor neurons. Interestingly, the effects of 3β,7α-diHCA and 3βH,7O-CA were specific to motor neurons as they did not affect the number of other midbrain neurons such as TH+ dopamine neurons, GABAergic or red nucleus neurons in the cultures (data not shown). Furthermore, neither 3β,7α-diHCA nor 3β-HCA altered the total number of Nkx6.1+ cells in the cultures (FIG. 13, panel C), which shows that the cholestenoic acids studied did not affect the number of Nkx6.1+ progenitor cells, but only mature double positive Islet1+; Nkx6.1+ oculomotor neurons. In order to examine whether the effects of 3β,7α-diHCA and 3βH,7O-CA were specifically mediated by Lxr receptors in the rodent brain, the applicants performed progenitor brain cultures from Lxrα–/–β–/– mice. Remarkably, the effects of the two cholestenoic acids (at their most potent concentration) on Islet1+ neurons were eliminated, confirming that 3β,7α-diHCA and 3βH,7O-CA regulate the number of Islet1+ cells in the rodent brain through Lxrs (FIG. 4, panel C). Moreover, the effects of these two acids were blocked by the Lxr antagonist GGPP, indicating that the observed effects are mediated by Lxr receptors (FIG. 4, panel D).

In order to unequivocally examine whether the effects of 3β,7α-diHCA and 3βH,7O-CA are indeed specifically mediated by Lxr receptors in the rodent brain, primary ventral midbrain cultures from Lxrα-/-β-/- mice were performed. Remarkably, the effects of the two cholestenoic acids on Islet1+ neurons were eliminated, confirming that 3β,7α-diHCA and 3βH,7O-CA regulate the number of Islet-1+ cells in the rodent brain through Lxrs (FIG. 4, panel A). Interestingly, 26-HC, a precursor of cholestenoic acids in the acidic pathway of bile acid biosynthesis, which had no Lxr activational effect in luciferase assays in neural cells (FIG. 2), was also shown to have no effect on the number of Islet1+ cells (data not shown). Furthermore, the effects of 3β,7α-diHCA, 3β,7β-diHCA or 3β-HCA on Islet1+ cells, were not altered by the known Lxr ligand 22R-HC (FIG. 9, panel C), which does not show an effect towards Islet1+ cells. These findings are very exciting as the applicants recently reported that brain endogenous Lxr ligands regulate neurogenesis and/or survival in the developing midbrain. However, none of the known endogenous brain Lxr ligands regulated the function of oculomotor neurons. The applicants thus decided to examine the mechanism by which 3β,7α-diHCA and 3βH,7O-CA increased the number of Islet1+ cells and studied their role in neurogenesis, proliferation and motor neuron survival in the developing brain.

Neurogenesis was examined in bromodeoxyuridine (BrdU) pulse-chase experiments, where neuronal progenitors in primary cultures are labeled with a pulse of BrdU at the beginning of the experiment and then are examined for their differentiation into motor neurons, as assessed by the acquisition of Islet-1 expression, a marker for motor neuron fate. Surprisingly, none of the cholestenoic acids studied affected the number of double BrdU+; Islet+ cells, indicating that they do not promote motor neuron neurogenesis. Similarly, none of the cholestenoic acids affected the total number of BrdU+ cells in the cultures, indicating that they do not modulate proliferation. Finally, it was tested whether cholestenoic acids regulate neuronal survival as assessed by active caspase-3 staining to detect the number of cells undergoing apoptosis in the cultures. Interestingly, treatment with 10 μM 3β,7α-diHCA decreased the number of active caspase-3+ cells (FIG. 4, panel E with representative pictures shown in FIG. 4, panel F). In contrast, 3βH,7O-CA did not affect the number of active caspase-3+ cells (FIG. 4, panels E and F), indicating that the increase in Islet1+ cells by this molecule is not due to increased survival, but rather neuronal differentiation. Cholestenoic acids that reduced the number of Islet1+ cells were also examined for their capacity to induce cell death in motor neuron cultures. Interestingly, the applicants found that low concentrations of either 3β,7β-diHCA or 3β-HCA increased the number of active caspase-3+ cells (FIG. 4, panels E and F) with toxicity being initiated at 1 μM. No surviving cells were detected when cultures were treated with concentrations of 3β,7β-diHCA or 3β-HCA higher than 5 μM. Time course experiments showed that toxicity was evident after two days of incubation.

The survival promoting effect of 3β,7α-diHCA was completely blocked by co-incubation with the Lxr inhibitor GGPP, indicating that the survival effect of this acid is mediated by Lxr (FIG. 4, panel G). On the contrary, the cell death effects of 3β,7β-diHCA or 3β-HCA (at 2 μM) were not blocked by GGPP (FIG. 4, panel G), indicating that the survival-promoting effects of 3β,7α-diHCA, but not the toxic effects of 3β,7β-diHCA or 3β-HCA, were mediated by Lxr.

In contrast, 10 μM 3βH,7O-CA did not affect the number of active caspase-3+ cells, indicating that the increase in Islet1+ cells is not due to increased survival, but rather neuronal differentiation. Cholestenoic acids that reduced the number of Islet1+ cells were also examined for their capacity to induce cell death in motor neuron cultures. Interestingly, the applicants found that lower concentrations, 2 μM, of either 3β,7β-diHCA or 3β-HCA increased the number of active caspase-3+ cells. Moreover, no surviving cells were detected when cultures were treated with 10 μM 3β,7β-diHCA or 3β-HCA. The cell death effects of these two acids (at 2 μM), unlike the survival-promoting effects of 3β,7α-diHCA, were not blocked by GGPP, indicating that the survival-promoting effects of 3β,7α-diHCA, but not the toxic effects of 3β,7O-diHCA or 3β-HCA, are mediated by Lxr. As a final experiment the applicants tested whether 3β,7α-diHCA could reduce the toxic effect of 3β,7β-diHCA or 3β-HCA. The applicants found that addition of 10 μM 3β,7α-diHCA reversed the loss of Islet1+ cells in the cultures treated with either 2 μM 3β,7β-diHCA or 3β-HCA (FIG. 4, panel 4J). This is an important finding as it offers an avenue for therapeutic intervention.

In order to examine whether there is competition between the effects of the cholestenoic acids studied the applicants performed several studies. In a binding and activation FRET assay, when 3β,7α-diHCA at its most potent concentration, was used together with increasing concentrations of 3β,7β-diHCA or 3β-HCA, the effect of 3β,7α-diHCA was reduced to that of the latter acids, indicating that there was competition between the various cholestenoic acids for binding to the LBD of Lxrβ (FIG. 6, panel A). Additionally, when the applicants tested whether 3β,7α-diHCA could reduce the toxic effect of 3β,7β-diHCA or 3β-HCA, the applicants found that treatment with 10 μM 3β,7α-diHCA reversed the loss of Islet1+ cells induced by either 2 μM 3β,7β-diHCA or 3β-HCA (FIG. 6, panel B). Finally, treatment with 10 μM 3β,7α-diHCA reduced the neuronal cell death (indicated by activated caspase 3) induced by either 2 μM 3β,7β-diHCA or 3β-HCA (FIG. 6, panel C). This is an important finding as it reinforces the notion of balance between the survival- and death-inducing effects of cholestenoic acids and offers a new avenue for therapeutic intervention.

Thus, combined, our results indicate that cholestenoic acids regulate the number of Islet+ motor neurons by controlling the expression of Islet-1 (3βH,7O-CA), and regulating neuronal survival in a positive (3β,7α-diHCA) or a negative (3β,7β-diHCA and 3β-HCA) manner.

Cyp7b1 Knockout Mice Exhibit Elevated Levels of 25-HC and do not Suffer from Motor Neuron or Liver Disease In light of the human diseases associated with mutations in the CYP7B1 and 27A1 genes the applicants decided to examine the sterol profiles of Cyp7b1 and Cyp27a1 knockout mice (Cyp7b1-/- and Cyp27a1-/-, respectively). As neither Cyp7b1-/- nor Cyp27a1-/- mice suffer from motor neuron dysfunction. The plasma and brain tissue samples from adult male knockout animals were analysed to search for the presence of the survival-promoting acid. LC-ESI-MS spectra of the Cyp7b1-/- mouse revealed an absence of 3β,7α-diHCA, its 7β-isomer and also 3βH,7O-CA both in plasma (n=9) and in whole brain tissue (n=7). An active bile acid biosynthesis pathway was maintained in these animals as indicated by the presence of 7αH,3O-CA in plasma (FIG. 9), formed via the neutral pathway of bile acid biosynthesis initiated via Cyp7a1 catalysed 7α-hydroxylation of cholesterol. Elevated levels of Cyp7b1 substrates 25-HC, 26-HC and 3β-HCA were found in both plasma and brain tissue of the knockout animals, compared to wild-type control animals (FIG. 5, panel 5A & FIG. 9). Thus, the analysis of the levels of sterols in plasma of Cyp7b1−/− mice show that these mice phenocopy to a large extent SPG5 patients (Table 2). However, the Cyp7b1−/− mouse does not show a motor neuron disease phenotype. This is in contrast to the adult male Lxrβ−/− animal, so the possibility exists that some other Lxr ligands in mouse may be responsible for providing a pro-survival effect towards motor neurons. Of the Lxr ligands identified in Cyp7b1−/− mouse brain 25-HC shows the greatest elevation in abundance in Cyp7b1−/− mouse, from undetectable levels in wild type mice to >2 ng/mg in 23 month old male mice. Significantly, this oxysterol is barely detectable in human brain and CSF (Table 1), and its level is not elevated in the CSF of SPG5 patients. Since 25-HC induced a modest increase in the levels of Islet-1 in Islet1-GFP transgenic fish in vivo (FIG. 3, panel 3B), the applicants investigated whether 25-HC could also promote motor neuron survival. The applicants found that 25-HC, shared with 3β,7α-diHCA its capacity to increase the number of Islet1+ oculomotor cells in E11.5 mice brain cultures (FIG. 5, panels 5B & 5C). Moreover this effect was inhibited by the Lxr antagonist GGPP (FIG. 5, panel 5D), and was blocked in cultures from Lxrα−/−β−/− animals (FIG. 5, panel 5B), indicating that the effect of 25-HC on motor neuron cell numbers is mediated by Lxrs. Finally, the applicants examined whether 25-HC was also capable of decreasing the number of apoptotic cells in motor neuron cultures. The applicants found that 25-HC reduced the number of active caspase-3+ cells in a GGPP sensitive manner (FIG. 5, panel 5E), indicating that the survival-promoting effects of 25-HC are specific and mediated by Lxr.

The applicants next analysed the oxysterol and cholestenoic acid profile of whole brain tissue of Cyp27a1−/− adult male mice and found an absence of 3β,7α-diHCA, 3βH,7O-CA and also 25-HC. The levels of 7α-HC and 7α-HCO; 7α,12α-diHC and 7α,12α-diHCO; 7α,25-diHC and 7α,25-diHCO; and also of a trihydroxycholesterol and a trihydroxycholest-4-en-3-one, probably 7α,12α,25-trihydroxycholesterol (cholest-5-ene-3β,7α,12α,25-tetrol, 7α,12α,25-triHC) and 7α,12α,25-trihydroxycholest-4-en-3-one (7α,12α,25-triHCO), were elevated in the brain of the knockout mouse (FIG. 5, panel 5F & FIG. 12).

3β,7α-diHCA Promotes Rodent Motor Neuron Survival In Vivo

In order to demonstrate motor neuron survival in vivo in a mammalian system, 3β,7α-diHCA was injected into the cerebral aqueduct of E11.5 mice in utero and brain sections were analyzed at E13.5 for Islet1−, TH- and ac3-positive cells. The applicants observed an increase in the number of Islet+ oculomotor neurons but not of TH+ neurons (FIG. 6, panels D and E). Upon injection of 3β-HCA the number of Islet+ oculomotor neurons was reduced, however, this effect was eliminated by co-injection of 3β,7α-diHCA. This data provide further support to the specificity of the neuronal survival and toxic effects of these cholestenoic acids on Islet1+, but not TH+, neurons reported in primary culture experiments above.

In addition the applicants occasionally observed double-positive Islet1+; ac3+ cells (FIG. 14), which suggested that there was a very limited number of oculomotor neurons undergoing apoptosis in vivo. This has not to our knowledge been shown before, therefore proving the strength of our injection technique.

Thus, our results show that specific cholestenoic acids have similar positive or negative effects on Islet1+ motor neurons both in vivo and in vitro.

The studies reported here show that cholestenoic acids are not mere intermediate metabolites of bile acid biosynthesis, but are rather a diverse family of bioactive compounds, capable of regulating nuclear receptor function. As such, cholestenoic acids were found to specifically activate Lxr and elicit an exquisite array of functions ranging from the regulation of Islet-1 expression, to the positive and negative regulation of motor neuron survival both in vitro and in vivo. Moreover, our study identifies cholestenoic acids in human CSF to be deregulated in plasma of patients with monogenetic motor neuron dysfunction, specifically CTX and SPG5 patients. Importantly, an absence of neuroprotective cholestenoic acids was found in CTX, while a combination of decreased neuroprotective and increased toxic cholestenoic acids was detected in SPG5. These results thus identify cholestenoic acids as key regulators of motor neuron function in development and disease.

Cholesterol is present at high levels in the CNS of vertebrates and is metabolized in brain predominantly to 24S-HC which accounts for about two thirds of brain cholesterol metabolism. Low levels of 26-HC have been found in human and mouse brain and in human CSF where it may be imported from the blood. Conversely, 7αH,30-CA, a metabolic product of 26-HC, is exported from brain to blood in human. Four intermediates in the biosynthesis of 7αH,30-CA from 26-HC via CYP27A1 and CYP7B1 to be present in CSF i.e. 3β,7α-diHCA, 3β-HCA, 7α,26-diHCO and 7α,26-diHC (FIG. 1, panel A) have been found by the applicants. While 3β-HCA and 7α,26-diHC were previously found in human neural tissue, 3β,7α-diHCA and 7α,26-diHCO have not been previously found in neural tissue or CSF. Importantly, the identification of these intermediates in the biosynthesis of 7αH,30-CA lends further support to the hypothesis that 7αH,30-CA is biosynthesised in the human brain. This pathway is also conserved in rodents where 26-HC is the precursor for the synthesis of 3β-HCA in fetal neurons and of 3β,7α-diHCA and 7αH,30-CA in fetal astrocytes (FIG. 1, panel A).

In human CSF and plasma the applicants also identified 3β,7β-diHCA but not its 3-oxo-4-ene metabolite. This result is in agreement with the earlier finding that hydroxysteroid dehydrogenase (HSD) 3B7, which acts on 7α-hydroxylated $C_{27}$ sterols converting them to their 3-oxo-4-ene analogs, is expressed in brain but does not metabolize 7β-hydroxylated sterols. The absence of such a metabolic sink may thus account for the comparatively high level of 3β,7β-diHCA in human CSF (Table 1). Importantly, here the applicants show that 3β,7β-diHCA and 3βH,7O-CA, the necessary intermediate in the epimerization reaction from the 3β,7α-isomer, also work as Lxr ligands (FIG. 2, panel A and FIG. 7, panel 7A).

Classical studies by Lehmann et al and Janowski et al defined the general structural requirements of steroidal Lxr ligands to be a 3β-hydroxy-5-ene function in the ring system and a hydroxy, oxo or epoxide function on the C-17 side-chain. The side-chain functions have more recently been extended to include a carboxylic acid group, a functional group which is also present in the synthetic non-steroidal Lxr ligand GW3965. In the current study, the applicants confirm the Lxr-activational capacity of cholestenoic acids with a 3β-hydroxy-5-ene structure in neural cells, and show that despite the introduction of either a 7α- or 7β-hydroxy or a 7-oxo group, Lxr activity is maintained. On the contrary, the 3-oxo-4-ene equivalents of these acids are not Lxr ligands. Thus, 3β-HCA, 3β,7α-diHCA, its 7β-isomer, and the necessary 7-oxo intermediate in the epimerization reaction, are all Lxr ligands. Moreover, none of these acids were found to activate Fxr, Vdr or Nurr1 in neural cells, thereby confirming the specificity of their effect on Lxr.

A number of studies in recent years have linked Lxr to neuronal degeneration. These studies have utilized Lxrβ−/− and Lxrα−/−β−/− mice. Indeed, both Lxr isoforms are expressed in brain and the knock-out mice show progressive accumulation of lipids in brain, abnormal blood brain barrier, increased reactive microglia, astrogliosis and degeneration of adult spinal cord motor neurons. Interestingly, a decrease in the number of oculomotor neurons was also detected during development in the Lxrα−/−β−/− mice at E11.5. However, it was not known whether Lxr ligands regulate the development of motor neurons in vivo. Moreover, the identity of endogenous brain Lxr ligands that regulate motor neuron function was unknown. Here the applicants used zebrafish to study the in vivo function of acid Lxr ligands newly identified in human CSF, 3β,7α-diHCA and 3β,7β-diHCA, and the 7-oxo intermediate in their epimerization, on Islet1+ cranial motor neurons. While metabolites that did not activate Lxr, such as 7αH,3O-CA, did not regulate the expression of Islet-1, the applicants found that two Lxr ligands 3β,7α-diHCA and 3βH,7O-CA enhance the expression of Islet-1 transcript and protein in zebrafish embryos (FIG. 3), effects that were abolished by injection of lxr MO (FIG. 10). These effects were confirmed in rodent primary oculomotor neuron cultures, which showed that only 3β,7α-diHCA and 3βH,7O-CA acids increased the number of Islet1+ neurons (FIG. 4, panels A-D). Importantly their activity was specific to and mediated by Lxr, as their biological activities were eliminated in cultures from Lxrα−/−β−/− mice. The effect of 3β,7α-diHCA on wild type cultures was accompanied by a decrease in the number of active caspase 3+ cells (FIG. 4, panel E), but no change in neurogenesis or proliferation was detected, indicating that the mechanism by which it increased the number of motor neurons was by promoting neuronal survival. In vivo experiments performed on embryonic brain in utero confirmed this neuroprotective effect of 3β,7α-diHCA on oculomotor neurons (FIG. 5, panels 5D-5E). In vivo experiments performed on embryonic brain in utero confirmed this neuroprotective effect of 3β,7α-diHCA on oculomotor neurons (FIG. 5, panels 5D-5E). In contrast, 3βH,7O-CA had no effect on cell death, neurogenesis or survival, but increased the expression of Islet-1, suggesting that it promoted the maturation of precursor cells into Islet1+ cells. Analysis of the function of 3β,7β-diHCA revealed a toxic effect which was manifested by an increase in the number of caspase3+ cells at low doses of this Lxr ligand (FIG. 4, panel E). Thus, our results indicate that only some of the cholestenoic acids capable of activating Lxr regulate motor neuron development. Our findings indicate that cholestenoic acids regulate motor neuron number by distinct mechanisms involving the regulation of differentiation and survival. Moreover, the applicants found that the regulation of motor neuron survival could be either positive, as shown by the neuroprotective effect of 3β,7α-diHCA, or negative, as shown by the toxic effect 3β,7β-diHCA and 3β-HCA (FIGS. 4 and 5). These results were quite unexpected but correlated very well with the cholestenoic acid profiles in patients with CTX and SPG5, two human diseases characterized by mutations in CYP27A1 and 7B1 genes, respectively, and which may present with signs of upper motor neuron loss or dysfunction. Indeed, the applicants found that 3β-HCA one of the Lxr ligands identified to have a toxic effect, was present at higher levels in SPG5 patients in both plasma and CSF (Tables 1 and 2). At the same time, the Lxr ligand found to be neuroprotective, 3β,7α-diHCA, was present at lower levels in SPG5 and absent in CTX (FIG. 1, panel C). Thus, our results suggest a double hit model for SPG5, in which the loss of motor neurons is contributed by both mechanisms, while in CTX, the predominant mechanism would be by the loss of neuroprotection.

The fact that the upper motor neuron phenotype of SPG5 and CTX often presents in the adolescent or adult argues against the Lxr ligands presented here being exclusively essential for motor neuron development. However, the applicants know that deletion of Lxrs results in motor neuron loss (1). Thus, the lack of an early phenotype in human patients with SPG5 or CTX indicates that other endogenous Lxr ligands are present in the brain and contribute to motor neuron development. Indeed the Cyp7b1−/− and Cyp27a1−/− mice, do not suffer from motor neuron disease despite an absence of 3β,7α-diHCA in brain and plasma (Table 4). This finding suggest that while the developmental function of the cholestenoic acids identified here is redundant with that of other Lxr ligands, the accumulative effect of altered levels of cholestenoic acids over extended periods of time, as in SPG5 and CTX, may play a decisive role in motor neuron disease.

To summarize, in this study the applicants identified 3β,7α-diHCA and 3β,7β-diHCA as Lxr ligands present in human CSF. Of these, 3β,7β-diHCA, and the previously identified Lxr ligand, 3β-HCA, were found to cause cell death, and the latter was present at high levels in patients with SPG5. Instead, 3β,7α-diHCA, which was found at low levels in SPG5 and was absent from CTX patients, promoted motor neuron survival, while 3βH,7O-CA regulated Islet-1 expression levels. Thus, our results uncover several novel functions of cholestenoic acids and identify them as Lxr ligands and as key regulators of motor neuron function in development and disease. Moreover, our study reveals that an orchestra of Lxr ligands regulates the development and survival of motor neurons. The results show that some specific cholestenoic acids selectively work on motor neurons, via Lxr, to regulate the balance between survival and death. These findings provide a mechanism for motor neuron dysfunction, for example in CTX and SPG5 and suggest that efforts aimed at restoring the balance between toxic and pro-survival Lxr ligands, such as administration of 3β,7α-diHCA or, in some cases, 25-HC may thus find a therapeutic application to prevent motor neuron loss and the treatment of motor neuron disease.

It is to be understood that the above embodiments have been provided only by way of exemplification of this invention, such as those detailed below, and that further modifications and improvements thereto, as would be apparent to persons skilled in the relevant art, are deemed to fall within the broad scope and ambit of the present invention described. Furthermore where individual embodiments are discussed, the invention is intended to cover combinations of those embodiments as well. The systems shown and described are not limited to the precise details and conditions disclosed. Method steps provided may not be limited to the order in which they are listed but may be ordered any way as to carry out the inventive process without departing from the scope of the invention. Furthermore, other substitutions, modifications, changes and omissions may be made in the design, operating conditions and arrangements of the exemplary embodiments without departing from the scope of the invention as expressed in the appended claims.

TABLE 1

Oxysterols and Cholestenoic Acids in Human CSF Oxysterols and cholestenoic acids identified by LC-ESI-MS$^n$ in CSF following SPE and charge-tagging with GP-hydrazine. In the absence of authentic standards presumptive identifications based on exact mass, MS$^n$ spectra and retention time are given.

| After cholesterol oxidase and GP-tagging | | | Originating structure Sterol Systematic name | | | | | |
|---|---|---|---|---|---|---|---|---|
| Mass | Formula | Sterol Systematic name | (Common name, abbreviation) | RT | RRT | AS | Mean concentration ng/mL ± SE | Note |
| 522.3326 | $C_{31}H_{44}N_3O_4^+$ | 7α-Hydroxy-3-oxochol-4-en-24-oic acid 3-GP | 7α-Hydroxy-3-oxochol-4-en-24-oic acid (7αH,3O-Δ$^4$-BA) | 2.06 | 0.34 | Yes | 0.230 ± 0.030† 0.507 ± 0.088‡ 0.423 ± 0.128• 0.058 ± 0.026* | 1, 2, 3 |
| 534.3690 | $C_{33}H_{48}N_3O_3^+$ | 7α-Hydroxy-26-nor-cholest-4-ene-3,24-dione 3-GP | 7α-Hydroxy-26-nor-cholest-4-ene-3,24-dione | 4.86 | 0.82 | No | 0.339 ± 0.056† 0.712 ± 0.093‡ 0.140 ± 0.038• 0.022 ± 0.022* | 1, 2, 3, 4 |
| 534.4054 | $C_{34}H_{52}N_3O_2^+$ | 24S-Hydroxycholest-4-en-3-one 3-GP | Cholest-5-ene-3β,24S-diol (24S-Hydroxycholesterol, 24S-HC) | 7.43 | 1.26 | Yes | 0.024 ± 0.003† 0.075 ± 0.003‡ 0.032 ± 0.010• 0.018 ± 0.006* | 5, 6 |
| 534.4054 | $C_{34}H_{52}N_3O_2^+$ | 25-Hydroxycholest-4-en-3-one 3-GP | Cholest-5-ene-3β,25-diol (25-Hydroxycholesterol, 25-HC) | 7.64 | 1.30 | Yes | 0.041 ± 0.004† 0.026 ± 0.003‡ 0.041 ± 0.018• 0.166 ± 0.048* | 3, 5, 6 |
| 534.4054 | $C_{34}H_{52}N_3O_2^+$ | 26-Hydroxycholest-4-en-3-one 3-GP | Cholest-5-ene-3β,26-diol (26-Hydroxycholesterol, 26-HC) | 7.99 | 1.36 | Yes | 0.042 ± 0.006† 0.146 ± 0.003‡ 0.215 ± 0.032• 0.915 ± 0.224* | 3, 5, 6 |
| 534.4054 | $C_{34}H_{52}N_3O_2^+$ | 7β-Hydroxycholest-4-en-3-one 3-GP | Cholest-5-ene-3β,7β-diol (7β-Hydroxycholesterol, 7β-HC) | 9.68 | 1.62 | Yes | 0.010 ± 0.002† 0.032 ± 0.027‡ 0.138 ± 0.060• 0.079 ± 0.022* | 3, 5, 6 |
| 534.4054 | $C_{34}H_{52}N_3O_2^+$ | 3β-Hydroxycholest-5-en-7-one 7-GP | 3β-Hydroxycholest-5-en-7-one (7-Oxocholesterol, 7O-C) | 9.78 | 1.66 | Yes | 0.069 ± 0.015† NM‡ NM• NM* | 5, 6, 7 |
| 534.4054 | $C_{34}H_{52}N_3O_2^+$ | 7α-Hydroxycholest-4-en-3-one 3-GP | Cholest-5-ene-3β,7α-diol (7α-Hydroxycholesterol, 7α-HC) | 10.20 | 1.72 | Yes | 0.023 ± 0.004† 0.026 ± 0.017‡ 0.190 ± 0.091• 0.122 ± 0.034* | 3, 5, 6 |
| 534.4054 | $C_{34}H_{52}N_3O_2^+$ | 6-Hydroxycholest-4-en-3-one 3-GP | Cholest-4-ene-3β,6-diol or Cholest-5-ene-3β,6-diol (6-Hydroxycholesterol, 6-HC) | 10.52 | 1.77 | Yes | 0.036 ± 0.006† 0.149 ± 00.042‡ 1.419 ± 1.174• 0.235 ± 0.138* | 3, 5, 6,8 |
| 546.3690 | $C_{34}H_{48}N_3O_3^+$ | 3-Oxocholesta-4,6-dien-26-oic acid 3-GP | 3-Oxocholesta-4,6-dien-26-oic acid | 7.28 | 1.23 | Yes | 1.110 ± 0.137† 2.047 ± 0.312‡ 1.182 ± 0.319• 0.159 ± 0.111* | 1, 3, 5,9 |
| 546.3690 | $C_{34}H_{48}N_3O_3^+$ | 3-Oxocholesta-4,6-dien-26-oic acid 3-GP | 3β-Hydroxycholesta-5,7-dien-26-oic acid | 7.28 | 1.23 | No | 0.400 ± 0.049† 0.467 ± 0.015‡ 0.213 ± 0.092• 0.079 ± 0.045* | 1, 2, 3, 10 |
| 548.3847 | $C_{34}H_{50}N_3O_3^+$ | 3-Oxocholest-4-en-26-oic acid 3-GP | 3β-Hydroxycholest-5-en-26-oic acid (3β-HCA) | 7.63 | 1.30 | Yes | 0.534 ± 0.061† 1.458 ± 0.095‡ 2.749 ± 0.098• 20.145 ± 2.756* | 1, 3, 5 |
| 550.4003 | $C_{34}H_{52}N_3O_3^+$ | 7α,25-Dihydroxycholest-4-en-3-one 3-GP | 7α,25-Dihydroxycholest-4-en-3-one (7α,25-diHCO) | 5.71 | 0.96 | Yes | 0.014 ± 0.001† 0.039 ± 0.001‡ 0.039 ± 0.002• ND* | 1, 3, 5, 11 |
| 550.4003 | $C_{34}H_{52}N_3O_3^+$ | 7α,25-Dihydroxycholest-4-en-3-one 3-GP | Cholest-5-ene-3β,7α,25-triol (7α,25-Dihydroxycholesterol, 7α,25-diHC) | 5.71 | 0.96 | Yes | ND† 0.028 ± 0.003‡ 0.045 ± 0.034• 0.015 ± 0.015* | 1, 3, 5, 11 |
| 550.4003 | $C_{34}H_{52}N_3O_3^+$ | 7α,26-Dihydroxycholest-4-en-3-one 3-GP | 7α,26-Dihydroxycholest-4-en-3-one (7α,26-diHCO) | 6.23 | 1.05 | Yes | 0.024 ± 0.004† 0.045 ± 0.002‡ 0.055 ± 0.018• ND* | 1, 3, 5 |

TABLE 1-continued

Oxysterols and Cholestenoic Acids in Human CSF Oxysterols and cholestenoic acids identified by LC-ESI-MS$^n$ in CSF following SPE and charge-tagging with GP-hydrazine. In the absence of authentic standards presumptive identifications based on exact mass, MS$^n$ spectra and retention time are given.

| After cholesterol oxidase and GP-tagging | | | Originating structure Sterol Systematic name | | | | Mean | |
|---|---|---|---|---|---|---|---|---|
| Mass | Formula | Sterol Systematic name | (Common name, abbreviation) | RT | RRT | AS | concentration ng/mL ± SE | Note |
| 550.4003 | $C_{34}H_{52}N_3O_3^+$ | 7α,26-Dihydroxycholest-4-en-3-one 3-GP | Cholest-5-ene-3β,7α,26-triol (7α,26-Dihydroxycholesterol, 7α,26-diHC) | 6.23 | 1.05 | Yes | ND† 0.028 ± 0.003‡ 0.043 ± 0.010• 0.005 ± 0.003* | 1, 3, 5 |
| 562.3639 | $C_{34}H_{48}N_3O_4^+$ | 24-Hydroxy-3-oxocholesta-4,6-dien-26-oic acid 3-GP | 24-Hydroxy-3-oxocholesta-4,6-dien-26-oic acid | 4.05 | 0.68 | No | 0.395 ± 0.051† 0.160 ± 0.035‡ 0.313 ± 0.067• 0.031 ± 0.031* | 1, 2, 3, 12 |
| 562.3639 | $C_{34}H_{48}N_3O_4^+$ | 25-Hydroxy-3-oxocholesta-4,6-dien-26-oic acid 3-GP | 25-Hydroxy-3-oxocholesta-4,6-dien-26-oic acid | 5.18 | 0.86 | No | 0.054 ± 0.002† 0.054 ± 0.013‡ ND• ND* | 1, 2, 3, 13 |
| 564.3796 | $C_{34}H_{50}N_3O_4^+$ | 7β-Hydroxy-3-oxocholest-4-en-26-oic acid 3-GP | 3β,7β-Dihydroxycholest-5-en-26-oic acid (3β,7β-diHCA) | 4.18 | 0.71 | Yes | 0.253 ± 0.051† 0.555 ± 0.027‡ 0.402 ± 0.100• 0.054 ± 0.043* | 1, 3, 5 |
| 564.3796 | $C_{34}H_{50}N_3O_4^+$ | 22,25-Dihydroxycholest-4-en-3,24-dione 3-GP | 3β,22,25-Trihydroxycholest-5-en-24-one | 5.12 | 0.87 | No | 0.074 ± 0.008† 0.269 ± 0.033‡ 0.211 ± 0.053• 0.223 ± 0.044* | 1, 2, 3, 14 |
| 564.3796 | $C_{34}H_{50}N_3O_4^+$ | 7α-Hydroxy-3-oxocholest-4-en-26-oic acid 3-GP | 7α-Hydroxy-3-oxocholest-4-en-26-oic acid (7αH,3O-CA) | 5.91 | 1.00 | Yes | 11.818 ± 1.626† 19.476 ± 2.490‡ 20.156 ± 7.774• 2.492 ± 1.316* | 1, 3, 5, 9 |
| 564.3796 | $C_{34}H_{50}N_3O_4^+$ | 7α-Hydroxy-3-oxocholest-4-en-26-oic acid 3-GP | 3β,7α-Dihydroxycholest-5-en-26-oic acid (3β,7α-diHCA) | 5.91 | 1.00 | Yes | 0.773 ± 0.103† 5.884 ± 0.460‡ 4.547 ± 1.941• 0.472 ± 0.438* | 1, 3, 5, 10 |
| 566.3952 | $C_{34}H_{52}N_3O_4^+$ | 7α,24(or26),25-Trihydroxycholest-4-en-3-one 3-GP | 7α,24(or26),25-Trihydroxycholest-4-en-3-one | 2.63 | 0.45 | No | 0.092 ± 0.006† 0.261 ± 0.010‡ 0.089 ± 0.089• ND* | 1, 2, 3, 15 |
| 578.3589 | $C_{34}H_{48}N_3O_5^+$ | 7α-Hydroxy-3,24-bisoxocholest-4-en-26-oic acid 3-GP | 7α-Hydroxy-3,24-bisoxocholest-4-en-26-oic acid | 2.34 | 0.39 | No | 0.068 ± 0.005† 0.200 ± 0.029‡ 0.233 ± 0.054• ND* | 1, 2, 3, 16 |
| 580.3745 | $C_{34}H_{50}N_3O_5^+$ | 7α,24-Dihydroxy-3-oxocholest-4-en-26-oic acid 3-GP | 7α,24-Dihydroxy-3-oxocholest-4-en-26-oic acid | 2.66 | 0.44 | No | 2.092 ± 0.314† 3.506 ± 0.540‡ 4.514 ± 1.126• 0.603 ± 0.380* | 1, 2, 3, 17 |
| 580.3745 | $C_{34}H_{50}N_3O_5^+$ | 7α,25-Dihydroxy-3-oxocholest-4-en-26-oic acid 3-GP | 7α,25-Dihydroxy-3-oxocholest-4-en-26-oic acid | 3.64 | 0.61 | No | 0.401 ± 0.068† 1.071 ± 0.270‡ 1.204 ± 0.665• 0.191 ± 0.157* | 1, 2, 3, 18 |

TABLE 1-continued

Oxysterols and Cholestenoic Acids in Human CSF Oxysterols and cholestenoic acids identified by LC-ESI-MS$^n$ in CSF following SPE and charge-tagging with GP-hydrazine. In the absence of authentic standards presumptive identifications based on exact mass, MS$^n$ spectra and retention time are given.

| After cholesterol oxidase and GP-tagging | | | Originating structure Sterol Systematic name | | | | Mean | |
|---|---|---|---|---|---|---|---|---|
| Mass | Formula | Sterol Systematic name | (Common name, abbreviation) | RT | RRT | AS | concentration ng/mL ± SE | Note |
| 596.3694 | $C_{34}H_{50}N_3O_6^+$ | Trihydroxy-3-oxocholest-4-en-26-oic acid 3-GP | Trihydroxy-3-oxocholest-4-en-26-oic acid | 2.15 | 0.27 | No | 0.063 ± 0.008† 0.108 ± 0.019‡ 0.036 ± 0.007• 0.059 ± 0.023* | 1, 2, 3, 19 |

Samples from 12 individual control subjects (†) and a pool of fifteen different control subjects (‡) were analysed. CSF from three SPG5 patients (*), and two health carriers, heterozygotes, with a single mutation in CYP7B1, (•) were also analysed.
RT = Retention time/min, RRT = Retention time relative to 7α-hydroxy-3-oxocholest-4-en-26-oic acid, AS = Authentic standard, SE = Standard error of 12 patient samples or of three technical replicates of the pooled sample, NM = not measured, ND = not detected. In some cases the exact location of side-chain oxo and hydroxy groups is equivocal in which case the most likely location is shown in bold. The SPG5 patients were: Patient 2, GAG and 22332 in Table S3. Control heterozygotes were GNI and GAN, mother and father of GAG, in Table S3.
1. Quantitative estimate based on [$^2H_6$]cholest-5-ene-3β,24(R/S)-diol internal standard.
2. Identification based on exact mass and MS$^n$ spectra.
3. Quantitative measurements based on GP-tagged 3-oxo-4-ene compounds giving similar ESI-MS response (9).
4. 26-Nor-sterol is a likely decomposition product of a 24-oxo-26-acid (see note 16). Possible alternatives to the 24-oxo group are an enol or epoxy group, all add 14 Da to the sterol structure.
5. Identification based on comparison with authentic standard.
6. Quantification based on [$^2H_6$]cholest-5-ene-3β,24(R/S)-diol internal standard.
7. Under the conditions employed 3β-hydroxy-7-oxo-5-ene sterols are not oxidised to their 3,7-bisoxo-4-ene equivalents.
8. Cholest-4-ene-3β,6-diol and/or cholesta-3β,6-diol are decomposition products of 3β-hydroxycholestan-5,6-epoxide and cholestane-3β,5α,6β-triol. Identification based on comparison with 6β-hydroxycholest-4-en-3-one reference standard.
9. 7α-Hydroxy-3-oxocholest-4-en-26-oic acid dehydrates to a minor degree to 3-oxocholesta-4,6-dien-26-oic acid. Thus, the total 7α-hydroxy-3-oxocholest-4-en-26-oic acid corresponds to the sum of the two acids.
10. 3β,7α-Dihydroxychoest-5-en-26-oic acid dehydrates to a minor degree to 3β-hydroxychoesta-5,7-dien-26-oic acid. Thus, the total 3β,7α-dihydroxychoest-5-en-26-oic acid corresponds to the sum of the two acids.
11. Identification based on comparison with cholest-5-ene-3β,7α,25-triol and cholest-5-ene-3β,7β,25-triol reference standards.
12. The MS$^n$ spectra suggest hydroxylation of the $C_{17}$ side-chain. 24-Hydroxy-3-oxocholesta-4,6-dien-26-oic acid is a likely dehydration product of 7α,24-dihydroxy-3-oxocholest-4-en-26-oic acid (see note 17).
13. The MS$^n$ spectra suggest hydroxylation of the $C_{17}$ side-chain. 25-Hydroxy-3-oxocholesta-4,6-dien-26-oic acid is a likely dehydration product of 7α,25-dihydroxy-3-oxocholest-4-en-26-oic acid (see note 18).
14. The MS$^n$ spectra suggest a 3β,22,25-trihydroxycholest-5-en-24-one or 3β,z-dihydroxycholest-5-en-26-oic acid structure, where z is a side-chain hydroxylation.
15. The MS$^n$ spectra suggest dihydroxylation of the $C_{17}$ side-chain, possibly at C-24 or C-26 and C-25.
16. The MS$^n$ spectra suggest a 24-oxo group. An alternative explanation is an enol or epoxy group, all add 14 Da to the sterol structure.
17. The MS$^n$ spectra suggest a hydroxyl group on the Cn side-chain, probably at C-24.
18. The MS$^n$ spectra suggest a hydroxyl group on the Cn side-chain, probably at C-25.
19. MS$^n$ spectra of insufficient quality to define location of substituents.

TABLE 2

Oxysterols and Cholestenoic Acids in Human Plasma (Serum) Oxysterols and cholestenoic acids identified by LC-ESI-MS$^n$ in plasma (serum) following SPE and charge-tagging with GP-hydrazine. In the absence of authentic standards presumptive identifications based on exact mass, MS$^n$ spectra and retention time are given.

| After cholesterol oxidase and GP-tagging | | | Originating structure Sterol | | | | Mean | |
|---|---|---|---|---|---|---|---|---|
| Mass | Formula | Sterol Systematic name | Systematic name (common name, abbreviation) | RT | RRT | AS | concentration ng/mL ± SE | |
| 506.3377 | $C_{31}H_{44}N_3O_3^+$ | 3-Oxochol-4-en-24-oic acid 3-GP | droxychol-5-en-24-oic acid $\Delta^5$-BA) | 4.57 | 0.75 | Y | 0.83 ± 0.14† 1.55 ± 0.38‡ 5.73 ± 0.24• 22.28 ± 4.53* 178.85 ± 88.40§ ND¶ | 1, 2, 3 |
| 522.3326 | $C_{31}H_{44}N_3O_4^+$ | 7α-Hydroxy-3-oxochol-4-en-24-oic acid 3-GP | 7α-Hydroxy-3-oxochol-4-en-24-oic acid (7αH,3O-$\Delta^4$-BA) | 2.18 | 0.36 | Y | 1.17 ± 0.23† 1.51 ± 0.67‡ 1.27 ± 0.29• 1.24 ± 0.32* 11.38 ± 7.33§ ND¶ | 1, 2, 3 |
| 522.3326 | $C_{31}H_{44}N_3O_4^+$ | 7α-Hydroxy-3-oxochol-4-en-24-oic acid 3-GP | 3β,7α-Dihydroxychol-5-en-24-oic acid (3β,7α-diH-$\Delta^5$-BA) | 2.18 | 0.36 | Y | 1.52 ± 0.34† 1.53 ± 0.63‡ 1.25 ± 0.02• 0.75 ± 0.42* 2.91 ± 2.38§ ND¶ | 1, 2, 3 |

TABLE 2-continued

Oxysterols and Cholestenoic Acids in Human Plasma (Serum) Oxysterols and cholestenoic acids identified by LC-ESI-MS$^n$ in plasma (serum) following SPE and charge-tagging with GP-hydrazine. In the absence of authentic standards presumptive identifications based on exact mass, MS$^n$ spectra and retention time are given.

| After cholesterol oxidase and GP-tagging | | | Originating structure Sterol | | | | Mean | |
|---|---|---|---|---|---|---|---|---|
| Mass | Formula | Sterol Systematic name | Systematic name (common name, abbreviation) | RT | RRT | AS | concentration ng/mL ± SE | |
| 532.3898 | $C_{34}H_{50}N_3O_2^+$ | Cholest-4-ene-3,24-dione 3-GP | Cholest-4-ene-3,24-dione | 7.91 | 1.27 | Y | 0.36 ± 0.03† ND‡ ND• ND* ND§ ND¶ | 1, 2, 3, 4 |
| 532.3898 | $C_{34}H_{50}N_3O_2^+$ | Cholest-4-ene-3,24-dione 3-GP | 3β-Hydroxycholest-5-en-24-one (24-Oxocholesterol, 24O-C) | 7.91 | 1.27 | Y | 0.24 ± 0.06† ND‡ 0.62 ± 0.10• 0.37 ± 0.10* 38.74 ± 4.03§ 0.29 ± 0.23¶ | 1, 2, 3, 4 |
| 534.3690 | $C_{33}H_{48}N_3O_3^+$ | 7α-Hydroxy-26-nor-cholest-4-ene-3,24-dione 3-GP | 7α-Hydroxy-26-nor-cholest-4-ene-3,24-dione | 5.16 | 0.83 | N | 0.2 ± 0.2† ND‡ 0.10 ± 0.10• 0.03 ± 0.02* 5.10 ± 4.27§ ND/ND/ND/ND¶ | 1, 2, 5, 6 |
| 534.4054 | $C_{34}H_{52}N_3O_2^+$ | 24S-Hydroxycholest-4-en-3-one 3-GP | Cholest-5-ene-3β,24S-diol (24S-Hydroxycholesterol, 24S-HC) | 7.60 | 1.24 | Y | 7.11 ± 0.40† 12.67 ± 0.26‡ 8.30 ± 0.07• 9.13 ± 1.94* 136.18 ± 43.06§ 10.11 ± 3.77¶ | 3, 7 |
| 534.4054 | $C_{34}H_{52}N_3O_2^+$ | 25-Hydroxycholest-4-en-3-one 3-GP | Cholest-5-ene-3β,25-diol (25-Hydroxycholesterol, 25-HC) | 7.91 | 1.29 | Y | 3.96 ± 0.27† 6.04 ± 0.97‡ 1.28 ± 0.06• 49.40 ± 11.38* 336.97 ± 86.56§ 3.60 ± 1.231¶ | 2, 3, 7, 8 |
| 534.4054 | $C_{34}H_{52}N_3O_2^+$ | 26-Hydroxycholest-4-en-3-one 3-GP | Cholest-5-ene-3β,26-diol (26-Hydroxycholesterol, 26-HC) | 8.14 | 1.33 | Y | 18.99 ± 0.85† 10.22 ± 2.65‡ 38.98 ± 1.39• 97.75 ± 7.28* 1320.94 ± 212.61§ ND¶ | 2, 3, 7 |
| 534.4054 | $C_{34}H_{52}N_3O_2^+$ | 7β-Hydroxycholest-4-en-3-one 3-GP | 7β-Hydroxycholest-4-en-3-one (7β-HCO) | 9.84 | 1.60 | Y | 2.62 ± 0.75† ND‡ ND• ND* ND/ND/ND§ ND¶ | 2, 3, 7, 9 |
| 534.4054 | $C_{34}H_{52}N_3O_2^+$ | 7β-Hydroxycholest-4-en-3-one 3-GP | Cholest-5-ene-3β,7β-diol (7β-Hydroxycholesterol, 7β-HC) | 9.84 | 1.60 | Y | 1.02 ± 0.58† ND‡ 0.70 ± 0.03 12.77 ± 12.52* 58.26 ± 45.96§ 24.01 ± 7.52¶ | 2, 3, 7, 9 |
| 534.4054 | $C_{34}H_{52}N_3O_2^+$ | 3β-Hydroxycholest-5-en-7-one 7-GP | 3β-Hydroxycholest-5-en-7-one (7-Oxocholesterol, 7O-C) | 9.93 | 1.62 | Y | 4.98 ± 2.25† ND‡ 2.78 ± 0.43 0.77 ± 0.29* 25.00 ± 19.60§ 34.35 ± 24.15¶ | 1, 3, 9 |
| 534.4054 | $C_{34}H_{52}N_3O_2^+$ | 7α-Hydroxycholest-4-en-3-one 3-GP | 7α-Hydroxycholest-4-en-3-one (7α-HCO) | 10.39 | 1.69 | Y | 2.43 ± 0.37† ND‡ 4.23 ± 4.23• 3.19 ± 0.79* 0.09 ± 0.09§ 70.77 ± 39.58¶ | 2, 3, 7, 9 |
| 534.4054 | $C_{34}H_{52}N_3O_2^+$ | 7α-Hydroxycholest-4-en-3-one 3-GP | Cholest-5-ene-3β,7α-diol (7α-Hydroxycholesterol, 7α-HC) | 10.39 | 1.69 | Y | 1.30 ± 0.39† ND‡ 1.48 ± 0.53• 6.75 ± 6.21* 36.39 ± 30.67§ 78.25 ± 51.06¶ | 2, 3, 7, 9 |

TABLE 2-continued

Oxysterols and Cholestenoic Acids in Human Plasma (Serum) Oxysterols and cholestenoic acids identified by LC-ESI-MS$^n$ in plasma (serum) following SPE and charge-tagging with GP-hydrazine. In the absence of authentic standards presumptive identifications based on exact mass, MS$^n$ spectra and retention time are given.

| After cholesterol oxidase and GP-tagging | | Originating structure Sterol | | | | | Mean concentration ng/mL ± SE | |
|---|---|---|---|---|---|---|---|---|
| Mass | Formula | Sterol Systematic name | Systematic name (common name, abbreviation) | RT | RRT | AS | | |
| 534.4054 | $C_{34}H_{52}N_3O_2^+$ | 6-Hydroxycholest-4-en-3-one 3-GP | Cholest-4-ene-3β,6-diol or Cholest-5-ene-3β,6-diol (6-Hydroxycholesterol, 6-HC) | 10.79 | 1.75 | Y | 1.96 ± 0.50† ND‡ 0.31 ± 0.31• 0.22 ± 0.19* ND§ 3.83 ± 2.52¶ | 2, 3, 7, 9, 10 |
| 546.3690 | $C_{34}H_{48}N_3O_3^+$ | 3-Oxocholesta-4,6-dien-26-oic acid 3-GP | 3-Oxocholesta-4,6-dien-26-oic acid | | | Y | 8.10 ± 0.74† 2.57 ± 1.56‡ 7.55 ± 1.60• 7.58 ± 1.96* 16.56 ± 9.53§ ND¶ | 1, 2, 3, 11 |
| 546.3690 | $C_{34}H_{48}N_3O_3^+$ | 3-Oxocholesta-4,6-dien-26-oic acid 3-GP | 3β-Hydroxycholesta-5,7-dien-26-oic acid | | | N | 6.20 ± 0.59† 2.56 ± 0.60‡ 1.54 ± 0.75• 1.73 ± 1.03* ND§ ND¶ | 1, 2, 5, 12 |
| 548.3847 | $C_{34}H_{50}N_3O_3^+$ | 3-Oxocholest-4-en-26-oic acid 3-GP | 3β-Hydroxycholest-5-en-26-oic acid (3β-HCA) | 7.84 | 1.28 | Y | 81.12 ± 4.31† 37.21 ± 7.77‡ 144.45 ± 38.53• 368.40 ± 65.27* 2909.35 ± 675.10§ ND¶ | 1, 2, 3 |
| 550.4003 | $C_{34}H_{52}N_3O_3^+$ | 7α,25-Dihydroxycholest-4-en-3-one 3-GP | 7α,25-Dihydroxycholest-4-en-3-one (7α,25-diHCO) | 5.87 | 0.96 | Y | 1.10 ± 0.32† 2.51 ± 1.83‡ 0.98 ± 0.18• ND* ND§ 4.64 ± 2.89¶ | 1, 2, 3 |
| 550.4003 | $C_{34}H_{52}N_3O_3^+$ | 7α,26-Dihydroxycholest-4-en-3-one 3-GP | 7α,26-Dihydroxycholest-4-en-3-one (7α,26-diHCO) | 6.38 | 1.04 | Y | 5.10 ± 0.56† 5.02 ± 2.52‡ 3.95 ± 2.06• 1.32 ± 0.26* 0.13 ± 0.13§ ND¶ | 1, 2, 3 |
| 550.4003 | $C_{34}H_{52}N_3O_3^+$ | 7α,26-Dihydroxycholest-4-en-3-one 3-GP | Cholest-5-ene-3β,7α,26-triol (7α,26-Dihydroxycholesterol, 7α,26-diHC) | 6.38 | 1.04 | Y | 0.92 ± 0.49† 1.27 ± 0.26‡ 0.49 ± 0.04• 0.20 ± 0.10* 0.57 ± 0.57§ ND¶ | 1, 2, 3 |
| 550.4003 | $C_{34}H_{52}N_3O_3^+$ | 7α,12α-Dihydroxycholest-4-en-3-one 3-GP | 7α,12α-Dihydroxycholest-4-en-3-one (7α,12α-diHCO) | 9.23 | 1.51 | Y | ND† ND‡ 0.08 ± 0.08• ND* ND§ 381.62 ± 250.33¶ | 1, 2, 3, |
| 550.4003 | $C_{34}H_{52}N_3O_3^+$ | 7α,12α-Dihydroxycholest-4-en-3-one 3-GP | Cholest-5-ene-3β,7α,12α-triol (7α,12α-Dihydroxycholesterol, 7α,12α-diHC) | 9.23 | 1.51 | Y | ND† ND‡ 0.03 ± 0.03• ND* ND§ 95.60 ± 76.01¶ | 1, 2, 3, |
| 562.3639 | $C_{34}H_{48}N_3O_4^+$ | 24-Hydroxy-3-oxocholesta-4,6-dien-26-oic acid 3-GP | 24-Hydroxy-3-oxocholesta-4,6-dien-26-oic acid | 4.39 | 0.71 | N | 0.2 ± 0.2† 0.2 ± 0.2‡ ND• 0.29 ± 0.17* ND§ ND¶ | 1, 2, 5, 13 |
| 564.3796 | $C_{34}H_{50}N_3O_4^+$ | 7β-Hydroxy-3-oxocholest-4-en-26-oic acid 3-GP | 3β,7β-Dihydroxycholest-5-en-26-oic acid (3β,7β-diHCA) | 4.45 | 0.73 | Y | 1.67 ± 0.32† 3.11 ± 1.00‡ 3.76 ± 2.02• 2.74 ± 0.58* 8.83 ± 4.42§ ND¶ | 1, 2, 3 |

TABLE 2-continued

Oxysterols and Cholestenoic Acids in Human Plasma (Serum) Oxysterols and cholestenoic acids identified by LC-ESI-MS$^n$ in plasma (serum) following SPE and charge-tagging with GP-hydrazine. In the absence of authentic standards presumptive identifications based on exact mass, MS$^n$ spectra and retention time are given.

| After cholesterol oxidase and GP-tagging | | Originating structure Sterol | | | | Mean | |
|---|---|---|---|---|---|---|---|
| Mass | Formula | Sterol Systematic name | Systematic name (common name, abbreviation) | RT | RRT | AS | concentration ng/mL ± SE |
| 564.3796 | $C_{34}H_{50}N_3O_4^+$ | 22,25-Dihydroxycholest-4-en-3,24-dione 3-GP | 3β,22,25-Trihydroxycholest-5-en-24-one | 5.44 | 0.88 | N | 5.37 ± 0.64† 4.74 ± 1.59‡ 4.78 ± 0.05• 15.70 ± 3.30* 29.77 ± 4.06§ 7.10 ± 1.29¶ | 1, 2, 5, 14 |
| 564.3796 | $C_{34}H_{50}N_3O_4^+$ | 7α-Hydroxy-3-oxocholest-4-en-26-oic acid 3-GP | 7α-Hydroxy-3-oxocholest-4-en-26-oic acid (7αH,3O-CA) | 6.11 | 1.00 | Y | 65.27 ± 6.22† 48.32 ± 16.97‡ 56.68 ± 9.94• 33.95 ± 5.81* 29.79 ± 14.82§ ND¶ | 1, 2, 3, 11 |
| 564.3796 | $C_{34}H_{50}N_3O_4^+$ | 7α-Hydroxy-3-oxocholest-4-en-26-oic acid 3-GP | 3β,7α-Dihydroxycholest-5-en-26-oic acid (3β,7α-diHCA) | 6.11 | 1.00 | Y | 39.40 ± 3.95† 28.83 ± 8.40‡ 19.76 ± 8.73• 5.21 ± 3.09* 1.16 ± 1.16§ ND¶ | 1, 2, 3, 12 |
| 566.3952 | $C_{34}H_{52}N_3O_4^+$ | 7α,24(or26),25-Trihydroxycholest-4-en-3-one 3-GP | 7α,24(or26),25-Trihydroxycholest-4-en-3-one | 2.84 | 0.46 | N | 0.65 ± 0.11† 3.38 ± 2.36‡ NM• ND* 1.60 ± 0.80§ ND¶ | 1, 2, 5, 15 |
| 580.3745 | $C_{34}H_{50}N_3O_5^+$ | 7α,24-Dihydroxy-3-oxocholest-4-en-26-oic acid 3-GP | 7α,24-Dihydroxy-3-oxocholest-4-en-26-oic acid | 2.89 | 0.47 | N | 0.2 ± 0.2† 0.56 ± 0.44‡ 0.95 ± 0.13• ND* ND§ ND¶ | 1, 2, 5, 16 |

Control samples from 56 adults (†) and 3 children (‡) were analysed. Data is also given for two health carriers, heterozygotes, with single mutations in CYP7B1 (•).
Data is given for seven adults showing clinically pure HSP SPG5 plus two adults with complicated HSP SPG5 (*) and three infants suffering from O7AHD (§). Data is also given four patients suffering from CTX (¶). Clinical data is given in Table S3.
RT = Retention time/min; RRT = Retention time relative to 7α-hydroxy-3-oxocholest-4-en-26-oic acid; AS = Authentic standard, Y = Yes, N = No; SE = Standard error of the mean; ND = Not detected; NM = Not measured. In some cases the exact location of the side-chain oxo or hydroxy groups is equivocal in which case the most likely location is shown in bold.
1. Quantitative estimate based on [$^2H_6$]cholest-5-ene-3β,24(R/S)-diol internal standard.
2. Quantitative measurements based on GP-tagged 3-oxo-4-ene compounds giving similar ESI-MS response (9).
3. Identification based on comparison with authentic standard.
4. 24S,25-Epoxycholesterol can isomerise to 3β-hydroxycholest-5-en-24-one during sample preparation.
5. Identification based on exact mass and MS$^n$ spectra.
6. 26-Nor-sterol is a likely decomposition product of a 24-oxo-26-acid. Alternatives to the oxo group are an enol or epoxy group, all add 14 Da to the sterol structure.
7. Quantification based on [$^2H_6$]cholest-5-ene-3β,24(R/S)-diol internal standard.
8. There is some tailing of the 24S-hydroxycholesterol peak into the 25-hydroxycholesterol peak, thus, values for 25- hydroxycholesterol are likely to be overestimated particularly when concentrations of 24S-hydroxycholesterol greatly exceed those of 25-hydroxycholesterol.
9. May be underestimation of levels of late eluting oxysterols.
10. Cholest-4-ene-3β,6-diol and/or cholest-5-ene-3β,6-diol are decomposition products of 3β-hydroxycholestan-5,6-epoxide and cholestane-3β,5α,6β-triol. Identification based on comparison with 6β-hydroxycholest-4-en-3-one reference standard.
11. 7α-Hydroxy-3-oxocholest-4-en-26-oic acid dehydrates to a minor degree to 3-oxocholesta-4,6-dien-26-oic acid. Thus, the total 7α-hydroxy-3-oxocholest-4-en-26-oic acid corresponds to the sum of the two acids.
12. 3β,7α-Dihydroxychoest-5-en-26-oic acid dehydrates to a minor degree to 3β-hydroxychoesta-5,7-dien-26-oic acid. Thus, the total 3α,7α-dihydroxychoest-5-en-26-oic acid corresponds to the sum of the two acids.
13. The MS$^n$ spectra suggest hydroxylation of the $C_{17}$ side-chain. 24-Hydroxy-3-oxocholesta-4,6-dien-26-oic acid is a likely dehydration product of 7α,24-dihydroxy-3-oxocholest-4-en-26-oic acid (see note 16).
14. The MS$^n$ spectra suggest a 3β,22,25-trihydroxycholest-5-en-24-one or 3β,z-dihydroxycholest-5-en-26-oic acid structure, where z is a side-chain hydroxylation.
15. The MS$^n$ spectra suggest dihydroxylation of the $C_{17}$ side-chain, possibly at C-24 or C-26 and C-25.
16. The MS$^n$ spectra suggest a hydroxy group on the $C_{17}$ side-chain, probably at C-24.

TABLE 3

Mutations in SPG5, O7AHD and CTX Patients Studied

| Sample code | Mutation | Reference | Family | Comment |
|---|---|---|---|---|
| | | | | HSP |
| P4505 II-1 (sister) | Compound heterozygous CYP7B1 c.260G > T/p.G87V c.889A > G/p.T297A | Arnoldi et al (*Clin Genet* 2012; 81(2): 150-7) | P4505 | Pure HSP (serum analysed) |

TABLE 3-continued

Mutations in SPG5, O7AHD and CTX Patients Studied

| Sample code | Mutation | Reference | Family | Comment |
| --- | --- | --- | --- | --- |
| P4505 II-2 (sister) | Compound heterozygous CYP7B1 c.260G > T/p.G87V c.889A > G/p.T297A | Arnoldi et al (supra) | P4505 | Pure HSP (serum analysed) |
| P52405 | Homozygous CYP7B1 c.1328G > C/p.G443A | Arnoldi et al (supra.) | P52405 | Complicated HSP (serum analysed) |
| Patient 2 (female) | Homozygous CYP7B1 c.825T > A/p.Y275X | Schüle et al (*J Lipid Res* 2010; 51(4): 819-23.) | | Complicated HSP (serum and CSF analysed) |
| AC (male) | Homozygous CYP7B1 c.889A > G/p.T297A | Present work | | Pure HSP (plasma analysed) |
| P II-1 (male) | Homozygous CYP7B1 c.806delA/p.D269VfsX282 | Criscuolo et al (*J Neurol* 2009; 256(8): 1252-7) | Family P | Pure HSP (plasma analysed) |
| S II-3 (female) | Homozygous CYP7B1 c.806delA/p.D269VfsX282 | Criscuolo et al (supra) | Family S | Pure HSP (plasma analysed) |
| Si II-1 (male) | Homozygous CYP7B1 c.1362insT/p.A453CfsX470 | Criscuolo et al (supra.) | Family Si | Pure HSP (plasma analysed) |
| GAG (male) | Compound heterozygous CYP7B1 c.250delC/p.L84FfsX6 c.266A > C/p.Y89S | Present work | Family G | Pure HSP (serum and CSF analysed) |
| | | | | O7AHD |
| JP (Infant male) | Homozygous CYP7B1 c.538C > T/p.R112X | Ueki et al (*J Pediatr Gastroenterol Nutr* 2008; 46(4): 465-9) | | O7AHD on treatment with UDCA (plasma analysed) |
| LT (Infant female) | Compound heterozygous CYP7B1 c.538C > T/p.R112X c.1453C > T/p.R417C | Mizuochi et al (*Liver Transpl* 2011; 17(9): 1059-65) | | O7AHD on treatment with UDCA (plasma analysed) |
| JI (Infant male) | Homozygous CYP7B1 c1249C > T/p.R417C | Chong et al (*J Inherit Metab Dis* 2010; 33(Suppl 1): S-382) | | O7AHD on treatment with UDCA (plasma analysed) |
| | | | | Heterozygote (healthy) Controls |
| GAN (male) | Heterozygous CYP7B1 c.250delC/p.L84FfsX6 | Present work | Family G | Father of GAG, unaffected (serum and CSF analysed) |
| GNI (female) | Heterozygous CYP7B1 c.266A > C/p.Y89S | Present work | Family G | Mother of GAG, unaffected (serum and CSF analysed) |
| GPO (male) | Heterozygous CYP7B1 c.266A > C/p.Y89S | Present work | Family G | Brother of GAG, unaffected (serum analysed) |
| | | | | CTX |
| 8876 Adult (female) | Homozygous CYP27A1 c.526delG | Present work | Family 887 | CTX On treatment with CDCA and simvastatin (plasma analysed) |
| 8875 Adult (male) | Homozygous CYP27A1 c.526delG | Present work | Family 887 | CTX On treatment with CDCA and simvastatin (plasma analysed) |
| 8577 Child (male) | Homozygous CYP27A1 c.1184 + 1G > A | Bourkiza et al (16) | | CTX Not on treatment (plasma analysed) |
| S2 Child (male) | Homozygous CYP27A1 IVS 6 + 1G > A | Present work | | CTX Not on treatment. Diagnosis based on clinical and biochemical grounds. Mutation analysis performed on affected brother (plasma analysed) |

TABLE 4

Cholestenoic Acids in Cyp7b1−/− and Cyp27a1−/− Mouse Brain and Plasmal
Cholestenoic acids identified by LC-ESI-MS following SPE and charge-tagging with GP-hydrazine.

| Sterol Systematic name (abbreviation) | Mouse age (months) | Mean concentration in brain (ng/mg ± SD) | | Mean concentration in plasma (ng/mL ± SD) | | Note |
|---|---|---|---|---|---|---|
| | | WT | Cyp7b1−/− | WT | Cyp7b1−/− | |
| 3β-Hydroxycholest-5-en-26-oic acid (3β-HCA) | 13 | 0.01 ± 0.00 | 0.12 ± 0.02*** | 1.97 ± 0.72 | 7.32 ± 1.50*** | 1, 2, 3 |
| | 23 | 0.01 ± 0.00 | 0.15 ± 0.01*** | 1.75 ± 0.50 | 6.69 ± 2.64** | |
| 7α-Hydroxy-3-oxocholest-4-en-26-oic acid (7αH,3O-CA) | 13 | ND | ND | 25.89 ± 10.91 | 14.21 ± 3.76 | 1, 2, 3 |
| | 23 | ND | ND | 25.19 ± 9.44 | 20.73 ± 1.77 | |
| 3β,7α-Dihydroxycholest-5-en-26-oic acid (3β,7α-diHCA) | 13 | ND | ND | ND | ND | 1, 2, 3 |
| | 23 | ND | ND | ND | ND | |
| | | WT | Cyp27a1−/− | WT | Cyp27a1−/− | |
| 3β-Hydroxycholest-5-en-26-oic acid (3β-HCA) | 3 | ND | ND | 3.56 ± 1.22 | ND** | 2, 3, 4 |
| | | ND | ND | | | |
| 7α-Hydroxy-3-oxocholest-4-en-26-oic acid (7αH,3O-CA) | 3 | ND | ND | 28.96 ± 7.22 | 5.23 ± 1.07** | 2, 3, 4 |
| | | ND | ND | | | |
| 3β,7α-Dihydroxycholest-5-en-26-oic acid (3β,7α-diHCA) | 3 | ND | ND | ND | ND | 2, 3, 4 |
| | | ND | ND | ND | ND | |

1. Wild type (WT) and Cyp 7b1−/− mouse plasma (13 months, n = 5; 23 months, n = 4) and brain (13 months, n = 3; 23 months, n = 4).
2. Data are means ± SD, *, p < 0.05; , p < 0.01; *, p < 0.001 compared to same age WT.
3. Quantification was by stable isotope dilution mass spectrometry using deuterated 24(R/S)-hydroxycholesterol as the internal standard.
4. Samples were from wild type (WT) and Cyp27a1−/− mice at 3 months, n = 3.

The invention claimed is:

1. A method for the treatment of a motor neuron disease, the method comprising administering to a patient in need thereof an effective amount of 3β,7α-dihydroxycholest-5-en-26-oic acid (3β,7α-diHCA) or a pharmaceutically acceptable salt thereof that would produce a suitable therapeutic effect in the patient, wherein the motor neuron disease consists of amyotrophic lateral sclerosis (ALS), primary lateral sclerosis (PLS), progressive bulbar palsy (PBP), or spinal muscular atrophy (SMA), wherein the amount of 3β,7α-dihydroxycholest-5-en-26-oic acid (3β,7α-diHCA) or the pharmaceutically acceptable salt thereof is between 0.01 mg/Kg and 1000 mg/Kg.

2. The method of claim 1 wherein the amount of 3β,7α-dihydroxycholest-5-en-26-oic (3β,7α-diHCA) in the individual is increased.

3. The method of claim 1 wherein the motor neuron disease is ALS.

4. The method of claim 2, further comprising reducing the amount in the individual of one or both of 3β,7β-dihydroxycholest-5-en-26-oic diHCA (3β,7β-diHCA) or 3β-hydroxycholest-5-en-26-oic (3β-HCA).

5. The method of claim 1, wherein the amount of 3β,7α-dihydroxycholest-5-en-26-oic acid (3β,7α-diHCA) or the pharmaceutically acceptable salt thereof is between 0.1 mg/Kg and 10 mg/Kg.

6. The method of claim 1, wherein the amount 3β,7α-dihydroxycholest-5-en-26-oic acid (3β,7α-diHCA) or the pharmaceutically acceptable salt thereof is between 0.1 mg/Kg and 10 mg/Kg.

* * * * *